United States Patent
Fiebich et al.

(10) Patent No.: US 11,485,700 B2
(45) Date of Patent: Nov. 1, 2022

(54) SYNTHESIS OF (+)-CANNABINOIDS AND THEIR THERAPEUTIC EFFECTS

(71) Applicant: SYMRISE AG, Holzminden (DE)

(72) Inventors: Bernd Fiebich, Freiburg (DE);
Matthias Winkler, Höxter (DE);
Marcus Rudolf Götz, Oberweser (DE);
Oskar Koch, Göttingen (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 17/255,590

(22) PCT Filed: Jun. 28, 2018

(86) PCT No.: PCT/EP2018/067366
§ 371 (c)(1),
(2) Date: Dec. 23, 2020

(87) PCT Pub. No.: WO2020/001770
PCT Pub. Date: Jan. 2, 2020

(65) Prior Publication Data
US 2021/0253509 A1    Aug. 19, 2021

(51) Int. Cl.
*C07C 67/02* (2006.01)
*C07C 37/50* (2006.01)
*C07C 67/32* (2006.01)
*C07C 67/03* (2006.01)
*C07C 67/30* (2006.01)

(52) U.S. Cl.
CPC .............. *C07C 67/02* (2013.01); *C07C 37/50* (2013.01); *C07C 67/03* (2013.01); *C07C 67/30* (2013.01); *C07C 67/32* (2013.01); *C07C 2601/16* (2017.05)

(58) Field of Classification Search
None
See application file for complete search history.

(56) References Cited

U.S. PATENT DOCUMENTS

| | | | |
|---|---|---|---|
| 9,670,133 B2* | 6/2017 | Koch | A61P 27/06 |
| 10,647,691 B2* | 5/2020 | Erfurt | C07D 311/80 |
| 2009/0298930 A1* | 12/2009 | Gutman | A61P 1/08 |
| | | | 514/455 |
| 2015/0336874 A1* | 11/2015 | Koch | C07C 67/29 |
| | | | 514/544 |
| 2017/0349517 A1 | 12/2017 | Dickman et al. | |

OTHER PUBLICATIONS

International Search Report and Written Opinion dated Mar. 14, 2019 for corresponding PCT Application No. PCT/EP2018/067366.

* cited by examiner

*Primary Examiner* — Amy C Bonaparte
(74) *Attorney, Agent, or Firm* — Polsinelli PC

(57) ABSTRACT

The present invention relates to a method of producing a compound of formula (I) or a salt of a compound of formula (I). The invention also relates to a compound of formula (I) or a salt of a compound of formula (I) for use in a therapeutic method to achieve one or more therapeutic effects as well as for use in the treatment and/or prevention of certain diseases. Furthermore, the invention provides a pharmaceutical composition comprising one or more compound(s) of formula (I) or salt(s) of compound(s) of formula (I).

7 Claims, 42 Drawing Sheets

SYNTHESIS OF (+)-CANNABINOIDS AND THEIR THERAPEUTIC EFFECTS

CROSS-REFERENCE TO RELATED APPLICATIONS

This application is a national stage application (under 35 U.S.C. § 371) of PCT/EP2018/067366, filed Jun. 28, 2018, which is incorporated herein by reference in its entirety.

The present invention relates to a method of producing a compound of formula (I)

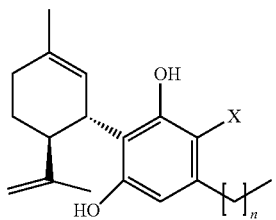

or a salt of a compound of formula (I). The meaning of X and n is explained below and preferred compounds are identified in the following disclosure. The invention also relates to a compound of formula (I) or a salt of a compound of formula (I) for use in a therapeutic method to achieve one or more therapeutic effects as well as for use in the treatment and/or prevention of certain diseases. Furthermore, the invention provides a pharmaceutical composition comprising one or more compound(s) of formula (I) or salt(s) of compound(s) of formula (I).

The most occurring cannabinoid found in *Cannabis Sativa*, cannabidiol (CBD), shows increasing interest for medicinal applications due to its broad biological activity spectrum. CBD is used as an active pharmaceutical ingredient in combination with dronabinol for MS therapy and as a single drug in the therapy of epileptic disorders like the Dravet syndrome.

The structurally related compound cannabidivarin (CBDV) is investigated in various clinical trials for its therapeutic anti-epileptic effect.

Naturally occurring CBD and CBDV have the absolute stereo conformation (−)-trans. Cisisomers or (+)-enantiomers are not produced in plants and have therefore until now no pharmaceutical impact. First biological studies of the enantiomer (+)-trans-CBD show surprising biological effects (Morales et al., "An overview on medicinal chemistry of synthetic and natural derivatives of cannabidiol", *Frontiers in Pharmacology,* 2017, Vol. 8, Article 422, doi: 10.3389/fphar.2017.00422). However, the available biological data is rudimentary.

The increasing demand of CBD in the course of the legalization of cannabinoids as a medicinal product led to the development of alternatives for the cultivation of cannabis plants. Besides the still in development phase situated various biosynthetic routes, the chemical synthesis of cannabinoids is the most promising alternative. Chemical synthesis can lead to a regulatory safe, active pharmaceutical ingredient. However, each synthetic process of a chiral molecule like CBD has to prove that the product is chirally pure. The cis-conformation can be excluded due to the chemical process (e.g. the process of CBD in EP2842933B1). To prove that the product is enantiomerically pure, in the case of CBD this would encompass the (−)-conformation, the process needs either proven enantiomeric pure raw products or definite chiral analytical methods. These methods could be the determination of the optical rotation of the product or chiral chromatographic methods like HPLC or GC. However, to validate these methods, both enantiomers are necessary. (+)-Cannabinoids therefore also have a large analytical potential as reference substances.

WO2017/011210A1 relates a synthesis for (+)-cannabidiol using halogens and halogen-containing compounds (brom, dichloromethane) and requiring large instrumental complexity. US2017/0349517A1 discloses a synthesis for (+)-cannabidivarin, which is performed in a batch process using dichloromethane as solvent and requiring cooling to −10 to −15° C.

There is still a need for efficient methods to produce enantiomerically pure (+)-cannabinoids and identify compounds with biological activity, which allows a therapeutic and/or preventive medical application.

It was therefore an object of the present invention to provide a method for the production of enantiomerically pure (+)-cannabinoids. In particular, the synthesis should be efficient and allow a continuous synthesis process without requiring a large instrumental complexity. Furthermore, it was an object of the present invention, that the purification of the product should be easy and in particular not require a (chiral) chromatography step. Moreover, it should be possible to start with not enantiomerically pure educts.

It was a further object of the present invention to provide enantiomerically pure (+)-cannabinoids, which have a biological activity that can be used to achieve specific therapeutic effects and allow treatment and/or prevention of certain diseases.

The above objectives are met by a method for producing a compound of formula (I)

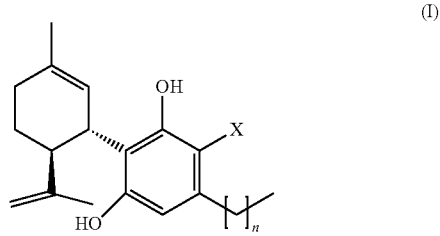

or a salt of a compound of formula (I),
wherein X=H or —COOY,
wherein Y=a saturated or unsaturated, branched or unbranched alkyl group, an aryl group, or a heteroaryl group, having 1 to 12 carbon atoms, respectively, and optionally substituted with one or more amino group(s), hydroxyl group(s) and/or halogen(s), and
wherein n=2 or 4,
comprising the step:
i) Reacting 4S-menthadienol with a compound of formula (II),

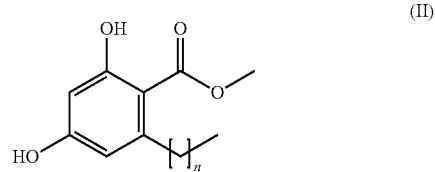

wherein n=2 or 4,
to obtain a compound of formula (III)

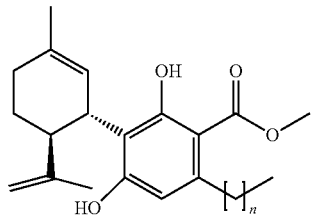
(III)

wherein n=2 or 4.

The first step of the process is the acid catalyst Friedel Craft addition of a 4S-menthadienol with a substituted resorcin derivative (olivetol methylester or divarin methylester). No cooling is required for this step, which is therefore preferably performed between 20° C. and 25° C. To ensure the (+)-configuration of the respective cannabinoid methyl ester, the starting material menthadienol has to have the 4S configuration. It can be either 1S,4S, 1R,4S or a mixture of both menthadienols due to the destruction of the 1S/1R stereo center during the addition. A 4R-menthadienol impurity, on the other hand, would lead to the respective (−)-cannabinoid. To investigate the stability of the process and its purification, a 4S menthadienol starting material can be used which contains 5% of 4R menthadienol as an impurity.

Scheme 1: Friedel Craft addition of a 4S-menthadienol with a substituted resorcin derivative

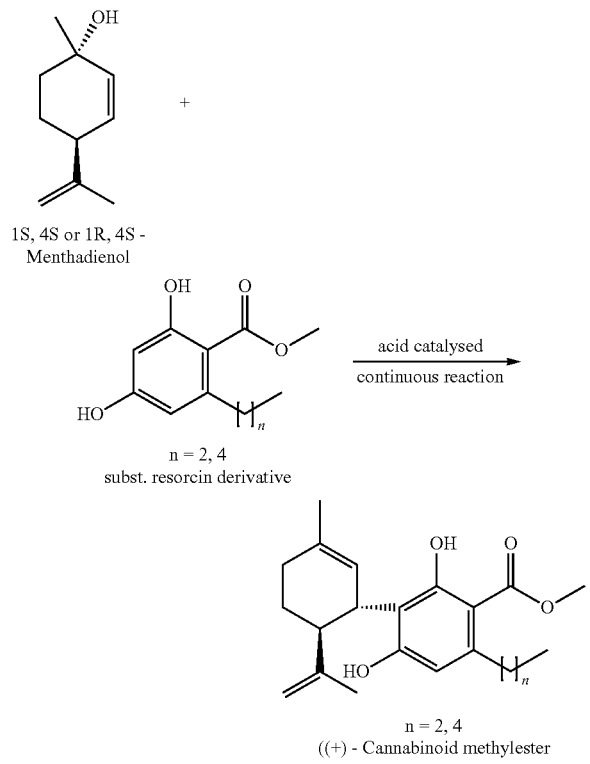

According to one embodiment, the method described above further comprises the step(s):

ii) Transesterification of the compound of formula (III), and/or iii) Decarboxylation of the compound of formula (III).

Before preforming step ii), the raw product, i.e. the compound of formula (III), does not need to be purified. Step ii) of the process contains the transesterification of the (+)-cannabinoid methylester and subsequently the acidic decarboxylation to the desired (+)-cannabinoid. The transesterification is preferably done in vacuum, preferably between 300 and 700 mbar, more preferably between 400 and 600 mbar, particularly preferably at around 500 mbar, to allow forming low boiling alcohol to be distilled off immediately. The intermediate ester formed by the transesterification is typically not isolated. Any alkyl alcohol may be used as a reaction partner in the transesterification. Preferred alcohols are given below. The products do not require purification by chiral chromatography to achieve >99% chiral purity.

According to a preferred embodiment, in the method described above, step i) is conducted as a batch or, preferably as a continuous flow reaction process.

The first step can be done as a batch reaction, but achieves better yields and purities if done as a continuous flow reaction using a flow cell reactor.

TABLE 1

Batch reaction—continuous flow reaction comparison for the synthesis of (+)-trans-Cannabidiol methylester (CBD-ME)

| Reaction type | Batch size | Purity raw CBD-ME | Yield |
|---|---|---|---|
| Batch reaction | 50 g | 57% | 46% |
|  | 100 g | 52% | 46% |
| Continuous flow reaction | 50 g | 78% | 68% |
|  | 100 g | 79% | 71% |

In a further preferred embodiment of the method described above, the compound of formula (I) is selected from the group consisting of the compounds (1) to (51 or a salt thereof

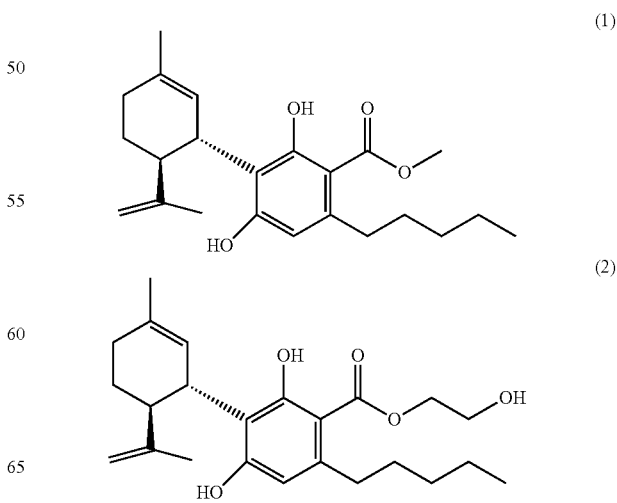

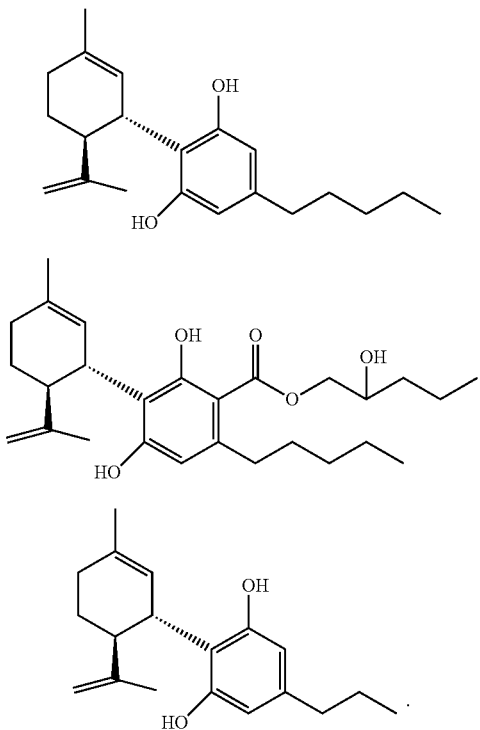

Compound (1): (+)-Cannabidiol methylester ((+)-CBD-ME)

Compound (2): (+)-Cannabidiol glycolester ((+)-CBD-GE)

Compound (3): (+)-Cannabidiol ((+)-CBD)

Compound (4): (+)-Cannabidiol hydroxypentylester ((+)-CBD-HPE)

Compound (5): (+)-Cannabidivarin ((+)-CBDV)

Compounds (1) to (5) have been shown to have biological activities, which allow therapeutic applications as explained in more detail below.

For salts of compounds of formula (I) and compounds (1) to (5) in the context of the present invention the following applies: Where appropriate, one or multiple hydroxyl group(s) of the compound(s) exist in a deprotonated form. In addition to the (deprotonated) compound(s), a corresponding amount of counter cations is present, wherein these are preferably selected from the group consisting of: singly positively charged cations of the first main group and first group of transition elements, ammonium ions, trialkylammonium ions, doubly positively charged cations of the second main group and second group of transition elements as well as triply positively charged cations of the third main group and third group of transition elements, as well as compositions thereof.

The phenolic hydroxyl groups of a compound are regularly more acidic than hydroxyl groups in the aliphatic side chain (if present).

The corresponding amount of counter cations (depending on their charge) results from the number of deprotonated hydroxyl groups. It arises, for example, from a compound of formula (I) with two phenolic hydroxyl groups underlying such a salt, that, in case of full deprotonation of these phenolic hydroxyl groups, a doubly negatively charged anion exists, whereof the number of positive charges (in this case: two) can be derived that have to be provided by the counter cation(s). Most preferably these counter cations are cations selected from the group consisting of $Na^+$, $K^+$, $NH_4^+$, $Ca^{2+}$, $Mg^{2+}$, $Al^{3+}$ and $Zn^{2+}$.

Further preferred is a method as described above, wherein in step i) pure 1S,4S-menthadienol or pure 1S,4R-menthadienol or a mixture of 1S,4S- and 1R,4S-menthadienol is used.

Surprisingly, the method according to the present invention allows the synthesis of enantiomerically pure (+)-cannabinoids and their derivatives from not enantiomerically pure starting material, i.e. a mixture of 1S,4S- and 1R,4S-menthadienol. The final products can be purified without having to perform any time consuming, expensive chiral purification methods and can still be obtained with a purity of >99% and also with enantiomeric purity of >99%.

According to a preferred embodiment of the method described above, step i) is conducted in a halogen-free solvent, preferably in toluene. Further possible solvents are benzene, xylene, cyclohexane or methyl-tert-butyl ester.

Advantageously, the method according to the present invention can be conducted in a halogen-free solvent, which avoids ecological issues. Preferably, step i) is conducted in toluene, which provides the best efficiency and reaction yield.

According to a further preferred embodiment of the method described above, in step i), a solution of a Lewis acid catalyst is provided and brought into contact with a solution of a compound of formula (II) and 4S-menthadienol.

In order to make sure that the catalyst is always present in the reaction chamber, the solution of the catalyst is charged into the reaction chamber prior to the solution of a compound of formula (II) and 4S-menthadienol. In case of a continuous flow reaction process, in which both solutions are pumped thorough a continuous flow reactor, the solution of the catalyst is preferably started before and ended after the solution of a compound of formula (II) and 4S-menthadienol.

In a preferred embodiment, the Lewis catalyst is boron trifluoride diethyl etherate. Using boron trifluoride diethyl etherate as catalyst has been shown to provide an efficient reaction with good yields.

As mentioned above, any allyl alcohol can be used as reaction partner for the transesterification reaction in step ii). Branched and unbranched, saturated or unsaturated alkyl alcohols as well as cyclic alkyl alcohols may be suitable. However, the best yield and selectivity is obtained when unbranched, saturated alkyl alcohols with a primary hydroxyl group are used.

In a further preferred embodiment, in step ii) a transesterification with ethylene glycol and/or 1,2-pentandiol is conducted.

A transesterification of compound (1) with ethylene glycol and/or 1,2-pentandiol in step ii) provides the compounds (2) and/or (4), respectively. Compounds (2) and (4) have been shown to have biological activities, which allow therapeutic applications as explained in more detail below. Furthermore, they can easily be decarboxylated to yield compound (3).

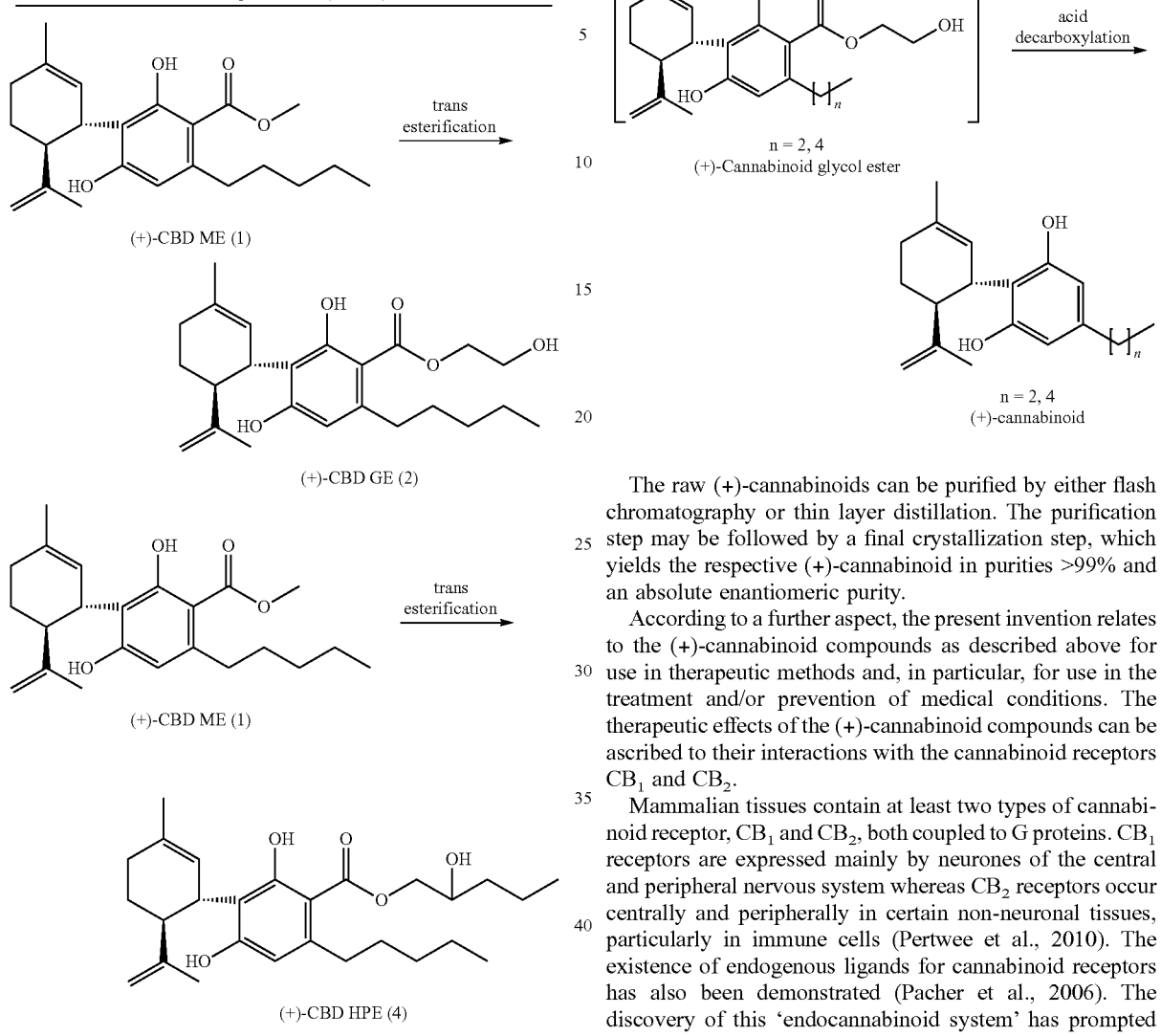

Scheme 2. Transesterification of compound (1) with ethylene glycol (top) and 1,2-pentan-diol (bottom)

(+)-CBD ME (1)
(+)-CBD GE (2)
(+)-CBD ME (1)
(+)-CBD HPE (4)

In a further preferred embodiment, an acid is used in step ii). Decarboxylation can be performed by addition of an acid such as sulfuric acid. Alternatively, hydrochloric acid may be used but preferably sulfuric acid is used.

Scheme 3: Transesterification with ethylene glycol and decarboxylation

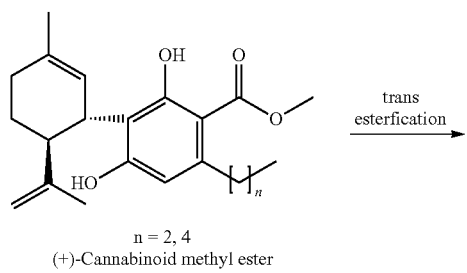

n = 2, 4
(+)-Cannabinoid methyl ester

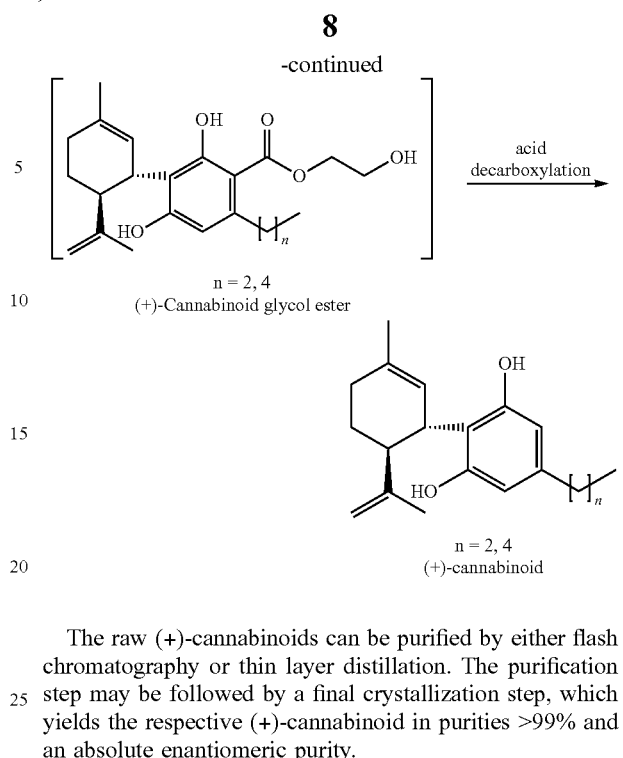

n = 2, 4
(+)-Cannabinoid glycol ester n = 2, 4
(+)-cannabinoid

The raw (+)-cannabinoids can be purified by either flash chromatography or thin layer distillation. The purification step may be followed by a final crystallization step, which yields the respective (+)-cannabinoid in purities >99% and an absolute enantiomeric purity.

According to a further aspect, the present invention relates to the (+)-cannabinoid compounds as described above for use in therapeutic methods and, in particular, for use in the treatment and/or prevention of medical conditions. The therapeutic effects of the (+)-cannabinoid compounds can be ascribed to their interactions with the cannabinoid receptors $CB_1$ and $CB_2$.

Mammalian tissues contain at least two types of cannabinoid receptor, $CB_1$ and $CB_2$, both coupled to G proteins. $CB_1$ receptors are expressed mainly by neurones of the central and peripheral nervous system whereas $CB_2$ receptors occur centrally and peripherally in certain non-neuronal tissues, particularly in immune cells (Pertwee et al., 2010). The existence of endogenous ligands for cannabinoid receptors has also been demonstrated (Pacher et al., 2006). The discovery of this 'endocannabinoid system' has prompted the development of a range of novel cannabinoid receptor agonists and antagonists, including several that show marked selectivity for $CB_1$ or $CB_2$ receptors.

The $CB_1$ receptor is located in the central and peripheral nervous system and inhabits an orthosteric and several allosteric binding sites for potential ligand bindings. (Price et al., 2005; Adam et al., 2007; Horswill et al., 2007; Navarro et al., 2009). Due to its distribution through the nervous system, activation of $CB_1$ receptors influences various cognitive processes (like attention, memory, motoric functions and pain reception) (Pertwee et al., 2008; Elphick et al., 2001). Inhibition of $CB_1$ receptors through $CB_1$ antagonists provides an expanding pharmaceutical applicability to target for example obesity (Dourish et al., 2008), opioid abuse (Sharma et al., 2007) and Parkinson disease (Concannon et al., 2015).

The $CB_2$ receptor is predominantly located in the peripheral tissues of the immune system and the gastrointestinal system, but can also be found in neurons of the brain (Chen et al., 2017). $CB_2$ receptors therefore can promote anti-inflammatory and immune modulatory (immune suppression, induction of apoptosis, and induction of cell migration), therapeutic effects (Basu et al., 2011). Additionally, $CB_2$ receptors have a potential therapeutic role in the treatment of neurodegenerative disorders such as Alzheimer's disease (Benito et al., 2003).

Both the central and peripheral cannabinoid receptors are members of the heptahelical G protein-coupled receptor superfamily. The cannabinoid receptors are known to mediate their effects through the pertussin toxin-sensitive Gi/o inhibition of adenylyl cyclase (Pacher et al., 2006).

For the use in medical/pharmaceutical preparations it is necessary to target distinct effects through selective interaction of the respective substances with the GB receptors. For example, Δ9-THC is a non-selective $CB_1$ and $CB_2$ agonist and has therefore a less defined efficacy profile.

All the tested (+)-cannabinoids showed specific binding activities to $CB_1$ and $CB_2$ in the nanomolar range which facilitates the potential use of the compounds in therapeutic doses.

Surprisingly none of the compounds showed $CB_1$ agonistic activities, but all compounds exhibited $CB_1$ antagonistic activities. (+)-CBD showed $CB_1$ antagonistic activity and in addition $CB_2$ agonistic activity. (+)-CBD-HPE showed an equal affinity for $CB_1$ and $CB_2$ and is a very potent $CB_1$ antagonist with a marginal $CB_2$ agonistic activity.

The tested compounds have a different but defined activity profile, with (+)-CBD being the most active. The selective activity profile enables the titled cannabinoids to be used for different targets dependent on the indications. Especially the surprising $CB_1$ antagonism offers the opportunity to target a variety of indications from obesity, opioid abuse, to neurodegenerative diseases like Parkinson's disease.

Primary human monocytes are a type of leukocytes, or white blood cells (PBMCs: peripheral blood mononuclear cells) present in human blood and representing about 10-30% of the PBMCs. Monocytes and their macrophage and dendritic-cell progeny serve three main and crucial functions in the immune system, phagocytosis, antigen presentation, and cytokine production. As a part of the vertebrate innate immune system monocytes also influence the process of adaptive immunity. It has been shown that human monocytes express $CB_2$ and that these receptors exert important roles in the immune function and immunomodulation (Klein et al., 2003). Studies of the $CB_1$ receptor and its role in primary human monocytes showed that activation of the receptor promotes pro-inflammatory responses of macrophages. Inhibition of $CB_1$ together with selective activation of $CB_2$ may suppress pro-inflammatory responses of macrophages (Han et al., 2009).

Primary human fibroblasts are the primary source of extracellular matrix (ECM) proteins, which, in addition to providing a scaffold for cells, play key roles in determining cell pheno-type and function. Fibroblasts contribute to injury responses in both the initiation and the resolution phases. They also function as accessory cells in many immune and inflammatory responses. Fibroblasts can produce or respond to a wide variety of cytokines, and these mediators allow fibroblasts and leukocytes to cooperate during complex processes such as wound healing. Fibroblasts are capable of modifying their output of extracellular matrix components in response to mediators released from other cell types. Some human chronic inflammatory diseases ultimately develop into disabling fibrotic disorders, demonstrating how persistent activation of the immune system can lead to severe perturbations in fibro-blast function. $CB_2$ receptors have been shown to modulate fibrogenesis in mouse skin wound repair. A previous study showed that $CB_2$ receptors are detected in the skin of mice, and are dynamically expressed in neutrophils, macrophages and myofibroblasts during skin wound healing in mice (Zheng et al., 2012). It has also been shown, that the $CB_2$ agonist JWH-133 prevents the development of skin and lung fibrosis as well as reduces fibroblast proliferation and the development of autoantibodies. Experiments performed in $CB_2$-deficient mice confirmed the influence of $CB_2$ in the development of systemic fibrosis and autoimmunity (Li et al., 2016; Servettaz et al., 2010). In addition to the effect of $CB_2$ modulation on fibroblasts the CB1 receptor showed to be an equally promising target. The $CB_1$ antagonist SR141716A for example inhibited progression of fibrosis in three models of chronic liver injury and showed that CB1 receptor antagonists hold promise for the treatment of liver fibrosis (Teixeira-Clerc et al., 2006; Marquart et al., 2010).

A human HaCAT keratinocyte is the predominant cell type in the epidermis, the outermost layer of the skin, constituting 90% of the cells found there. The primary function of keratinocytes is the formation of a barrier against environmental damage by pathogenic bacteria, fungi, parasites, viruses, heat, UV radiation and water loss. It has been shown that human keratinocytes partake in the peripheral endocannabinoid system and show a signaling mechanism of $CB_1$ receptors, which may have important implications in epidermal differentiation and skin development. Cannabinoids inhibit human keratinocyte proliferation through a non-$CB_1$/$CB_2$ mechanism and have a potential therapeutic value in the treatment of psoriasis (De Petrocellis et al., 2004; Wilkinson et al., 2007).

The tested (+)-cannabinoids showed various biological activities in different cell lines. Interestingly, all cannabinoids presented different effects. This can be affiliated in most cases to their $CB_1$/$CB_2$ activity.

(+)-CBD showed potent anti-inflammatory effects in monocytes (besides IL-1, MMP9, and isoprostane) and fibroblasts. These effects are likely associated with the demonstrated $CB_1$-antagonism/$CB_2$ agonism of the compound.

(+)-CBDV showed potent anti-inflammatory effects in a comparable profile to (+)-CBD, slightly less potent but also weakly inhibiting LPS-induced IL-1. This effect can be partly affiliated to the shown $CB_1$ antagonism of the compound. Since (+)-CBDV does not exhibit $CB_2$ agonism it may be speculated whether the anti-inflammatory effects are strictly due to the $CB_1$ antagonism or if there are additional interactions.

(+)-CBD-ME showed only slight inhibitory effects on LPS-mediated TNF alpha and IL-6, a weak inhibition on IL-1 induced PGE2 in fibroblasts, and inhibition of Poly I:C stimulated TIMP1 in HaCat being the least active compound of the 5 tested. This directly corresponds to its weak effects on $CB_1$/$CB_2$ receptors ((+)-CBD-ME showed the weakest $CB_1$ antagonistic effect of the tested compounds and no effect on the CB2 receptor).

(+)-CBD-GE showed also a potent inhibitory profile in monocytes and fibroblasts preventing most of the inflammation induced parameters besides IL-8 and MMP9, which were even increased by this cannabinoid. This increase could be associated with the cytotoxic effect of the compound at higher doses. A weak inhibition of MMP9 and TIMP1 was observed in Poly I:C-treated HaCat cells.

(+)-CBD-HPE was not as potent as (+)-CBD, (+)-CBDV and (+)-CBD-GE, showing only potent inhibition of LPS-induced PGE2 in monocytes, IL-6 and IL-8 stimulated by IL-1 in fibroblasts and MMP9 and TIMP induced by Poly I:C in HaCat cells. This is surprising since (+)-CBD-HPE showed the highest $CB_1$ antagonism and is besides (+)-CBD the only other cannabinoid which exhibited $CB_2$ agonism. Of all 5 tested cannabinoids, (+)-CBD-HPE exhibits the lowest Ki value regarding binding on both cannabinoid receptors. Additional interactions are likely to contribute to the shown effects.

The present invention therefore relates to a compound of formula (I) or salt of a compound of formula (I), preferably selected from the group consisting of compounds (1) to (5) or salt thereof, for use in a therapeutic method to achieve an effect selected from the group consisting of
anti-inflammatory,
immunomodulatory,
immunosuppressant,
immunostimulant,
analgetic.

All tested (+)-cannabinoid compounds showed anti-inflammatory effects, though (+)-CBD, (+)-CBDV and (+)-CBD-GE were the most potent and are therefore preferred for use in a therapeutic method to achieve an anti-inflammatory effect.

As $CB_2$ receptor agonists promote immune modulatory effect, i.e. immunosuppression or immunostimulation, (+)-CBD and (+)-CBD-HPE are preferred for the use in a therapeutic method to achieve an immunomodulatory effect, in particular an immunosuppressant or immunostimulant effect. Since (+)-CBD shows the strongest $CB_2$ agonism, it is particularly preferred for the use in a therapeutic method to achieve an immunomodulatory effect, in particular an immunosuppressant or immunostimulant effect. $CB_2$ receptor agonists are also useful as analgetic therapeutics. Therefore, (+)-CBD and (+)-CBD-HPE, in particular (+)-CBD, is/are preferred for the use in a therapeutic method to achieve an analgetic effect.

A particularly preferred embodiment of the present invention is therefore a compound of formula (I) for use in a therapeutic method as described above, wherein the compound of formula (I) is compound (3) or a salt of compound (3).

CB2-Agonists are promising analgetic therapeutics for various pain disorders (chronic, neuropatic, inflammatory) (Le Boisselier et al., 2017; Likar et al., 2017). Additionally, CB2-agonists are beneficial in the therapy of neuro inflammatory and neurodegenerative diseases like multiple sclerosis (Pertwee, 2007; Dittel, 2008) Huntington's disease (Sagredo et al., 2012), Alzheimer's disease (Aso et al., 2016) and furthermore in the therapy of cerebral strokes (Zhang et al., 2007).

CB2-Agonists are also promising therapeutics for peripheral inflammatory diseases like arterio sclerosis (Mach et al., 2008) or inflammatory bowel diseases (Izzo et al., 2008; Wright et al., 2008), ischemia (Batkai et al., 2007), diabetic nephropathy (Barutta et al., 2011) and liver cirrhosis (Izzo et al., 2008; Mallat et al., 2007; Lotersztajn et al., 2008).

Epidemiological and pre-clinical data show that activation of CB2 receptors give a beneficial therapeutic effect in osteoporosis (Ofek et al., 2006). Furthermore, there is clinical data that CB2-Agonists are effective against certain cancer typs (Izzo et al., 2008; Wright et al., 2008; Guzman, 2003).

CB1-Antagonists are promising therapeutics for obesity and furthermore diabetes (Dourish et al., 2008; Badal et al., 2017; Wagner et al., 2012) and therefore believed to be important for the weight loss paradigm. Additionally, they show beneficial effects in the therapy of drug cessation and drug withdrawal (alcohol, tobacco, narcotics) (Ravan et al., 2014; Chandler et al., 2009; Koob et al., 2014).

CB1-Antagonists are furthermore used to treat non-alcoholic fatty liver disease (NAFLD) by blocking fatty liver metabolism (Badal et al., 2017). Additionally, CB1-antagonists are promising therapeutics in the treatment of neurodegenerative diseases like Parkinson's disease (Brotchie, 2003; Cerri et al., 2014).

A preferred embodiment of the present invention is therefore a compound of formula (I) or salt of a compound of formula (I), preferably selected from the group consisting of compounds (1) to (5) or salt thereof, for use in the treatment and/or prevention of inflammatory diseases such as neuroinflammatory diseases, arteriosclerosis, inflammatory bowel disease or ischemia and/or pain disorders, such as chronic pain, neuropathic pain or diabetic neuropathy and/or neurodegenerative diseases, such as multiple sclerosis, Huntington's disease, Alzheimer's disease or Parkinson's disease and/or cerebral stroke and/or liver cirrhosis and/or osteoporosis and/or cancer and/or obesity and/or diabetes and/or liver fibrosis and/or non-alcoholic fatty liver disease and/or psoriasis and/or for use in the treatment of symptoms of cessation or withdrawal of narcotics, opioids, tobacco or alcohol.

Preferably, the compound of formula (I) for use in the treatment and/or prevention as described above is compound (3) or a salt of compound (3).

The present invention also relates to a pharmaceutical composition comprising one or more compound(s) of formula (I) or salt(s) of compound(s) of formula (I), preferably selected from the group consisting of compounds (1) to (5) or salt(s) thereof.

The pharmaceutical composition according to the invention is preferably selected from the group consisting of solid galenic forms (e.g. tablets (with coating or without, with modified release or without), dragées (with coating or without, with modified release or without), capsules (soft or hard gelatin capsules with modified release or without), granulates (with modified release or without), powders (with modified release or without, e.g. nose powders, ear powders), suppositories (with coating or without, with modified release or without), lozenges, chewing gums, semi-solid forms (e.g. hydrophobic ointments amongst them e.g. hydrocarbon gels, lipogels, silicon gels, oleo gels as well as water-absorbing ointments amongst them e.g. absorption bases, hydrophilic ointments, hydrophilic gels (hydrogels) or pastes, also nasal ointments), inhalants (e.g. pressure gas metered dose inhalers, powder inhalers, inhalers with nebulizers, inhalation concentrates for inhalation), injectables and implants (e.g. on the basis of liquid or solid forms that are suitable for the preparation of or use as injectable solutions or solid matrices that enable modified release), patches containing active ingredients, ear tampons.

Liquid forms are e.g. solutions, suspensions, emulsions, syrups (colloquially cough syrup), mouthwashes, gargle solutions, throat sprays or nasal sprays, nose drops, nasal rinsing solutions, ear drops, ear sprays and ear rinsing solutions.

Pharmaceutical compositions preferably contain one or multiple component(s) selected from the following group: Filling material (e.g. cellulose, calcium carbonate), flow agents and anti-caking agents (e.g. talcum, magnesium stearate), coatings (e.g. polyvinyl acetate phthalate, hydroxypropyl methylcellulose phthalate), disintegrants (e.g. starch, crosslinked polyvinylpyrrolidone), plasticizers (e.g. triethyl citrate, dibutyl phthalate), substances for granulation (lactose, gelatin), retardation (e.g. poly(meth)acrylic acid-methyl/ethyl/2-trimethyl-aminoethyl ester copolymers in dispersion, vinyl acetate/crotonic acid copolymers), compacting (e.g. microcrystalline cellulose, lactose), solvents, suspension or dispersing agents (e.g. water, ethanol), emulsifying agents (e.g. cetyl alcohol, lecithin), substances for modification of rheological properties (silicon dioxide, sodium alginate), substances for microbial stabilization (e.g. benzalkonium chloride, potassium sorbate), preservatives and antioxidants (e.g. DL-alpha-tocopherol, ascorbic acid), substances for modification of the pH value (lactic acid, citric acid), propellant or inert gas (e.g. fluorinated chlorinated hydrocarbons, carbon dioxide), colorants (iron oxide, titanium oxide), ointment base materials (e.g. paraffin wax, beeswax), inter alia as they can be found in the technical literature (e.g. Schmidt, P. C., Christin, I. "Wirk-und Hilfsstoffe für Rezeptur, Defektur und Großherstel-lung", 1999, Wissenschaftliche Verlagsgesellschaft mbH Stuttgart or Bauer, K. H., Frömming, K-H., Führer, C. "Lehrbuch der Pharmazeutischen Technologie", 8. Auflage, 2006, Wissenschaftliche Verlagsgesellschaft mbH Stuttgart).

The preferably used amounts of one or more compound(s) of formula (I) and/or one or more salt(s) thereof in a pharmaceutical composition, can easily be determined by a person skilled in the art by simple trial and error methods dependent on the kind and purpose of the respective formulation.

SHORT DESCRIPTION OF THE FIGURES

Figure 1:
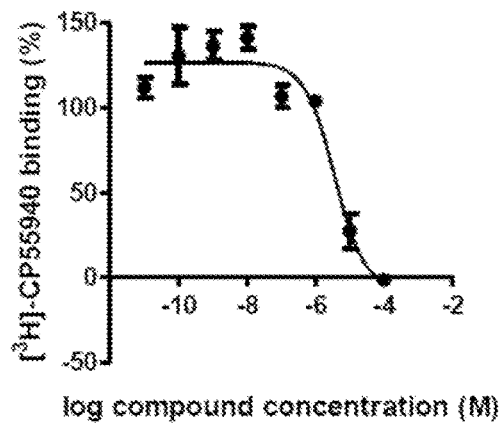
FIG. 1 shows the $CB_1$ (left) and $CB_2$ (right) binding of (+)-CDB as evaluated in example 4.
Figure 1:
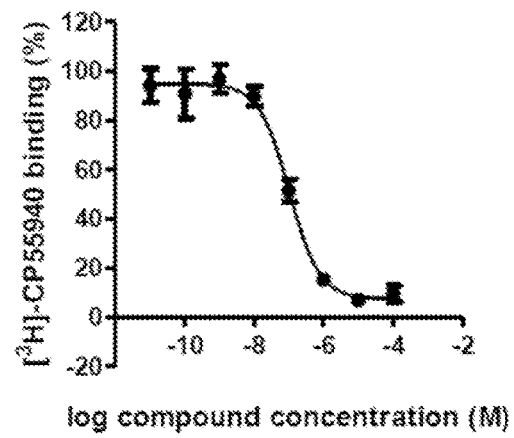
Figure 2:
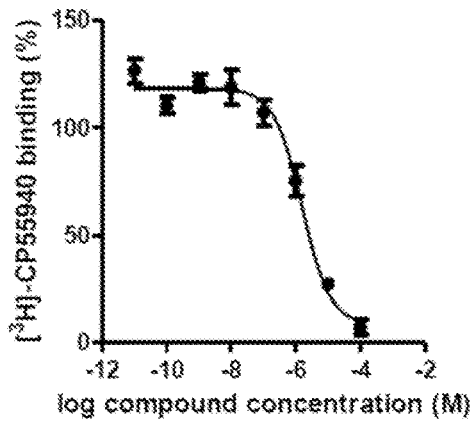
FIG. 2 shows the $CB_1$ (left) and $CB_2$ (right) binding of (+)-CBDV as evaluated in example 4.
Figure 2:
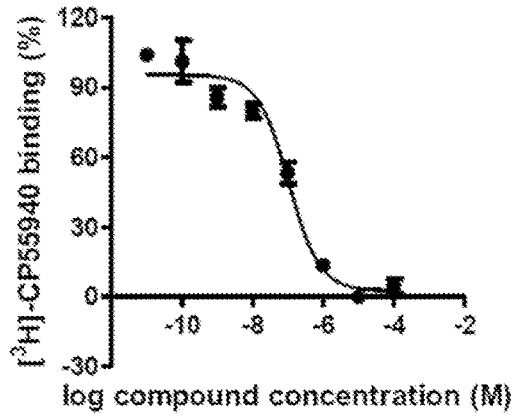
Figure 3:
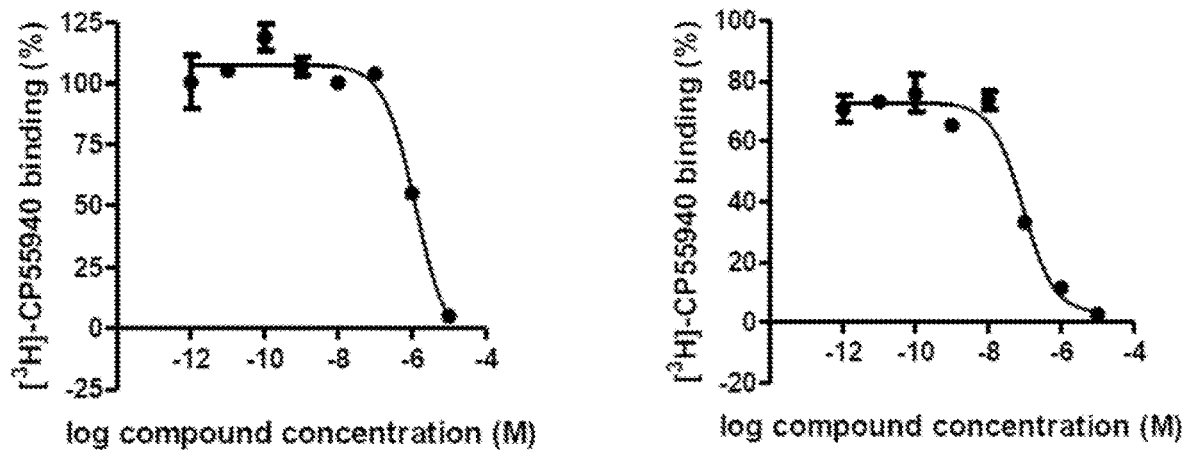
FIG. 3 shows the $CB_1$ (left) and $CB_2$ (right) binding of (+)-CBD-ME as evaluated in example 4.
Figure 4:
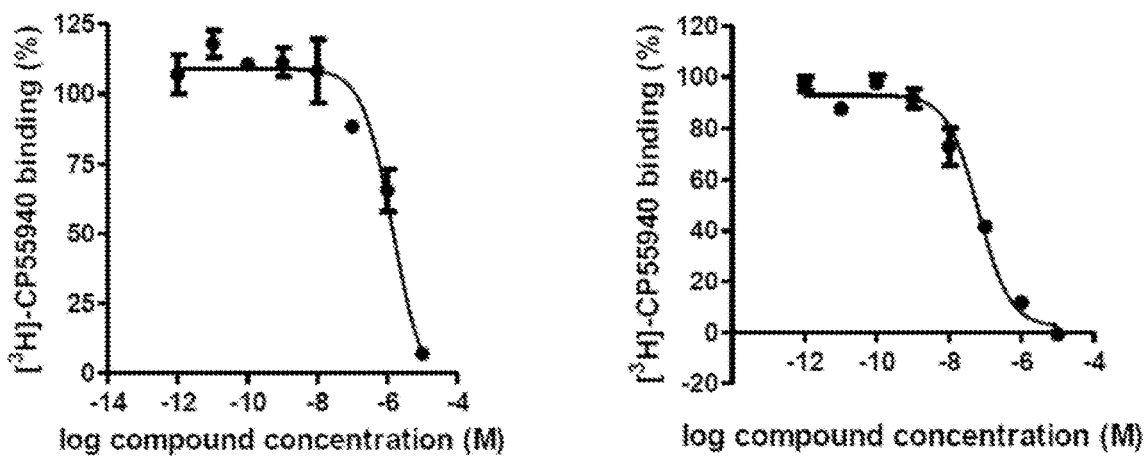
FIG. 4 shows the $CB_1$ (left) and $CB_2$ (right) binding of (+)-CBD-GE as evaluated in example 4.
Figure 5:
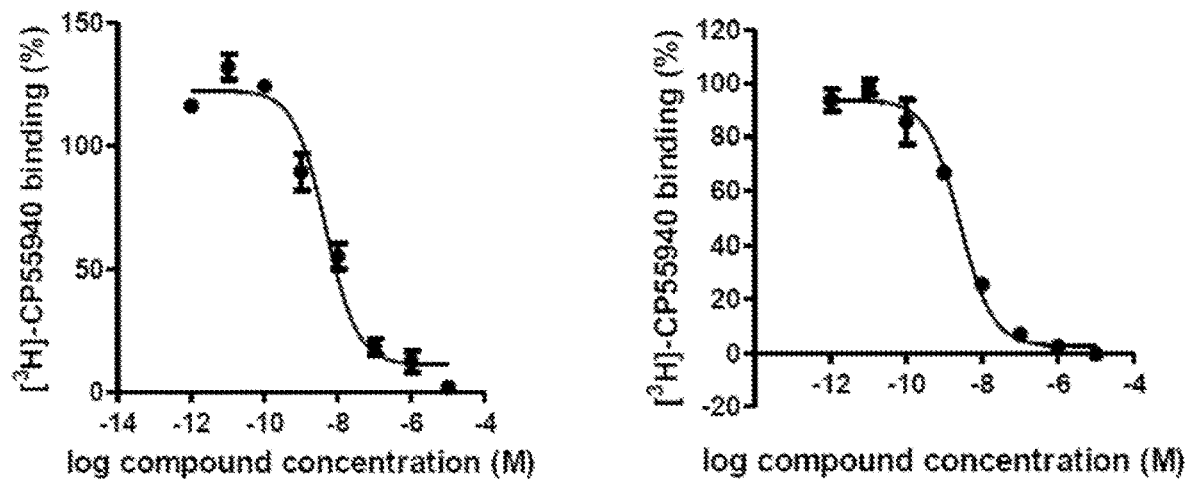
FIG. 5 shows the $CB_1$ (left) and $CB_2$ (right) binding of (+)-CBD-HPE as evaluated in example 4.
Figure 6:
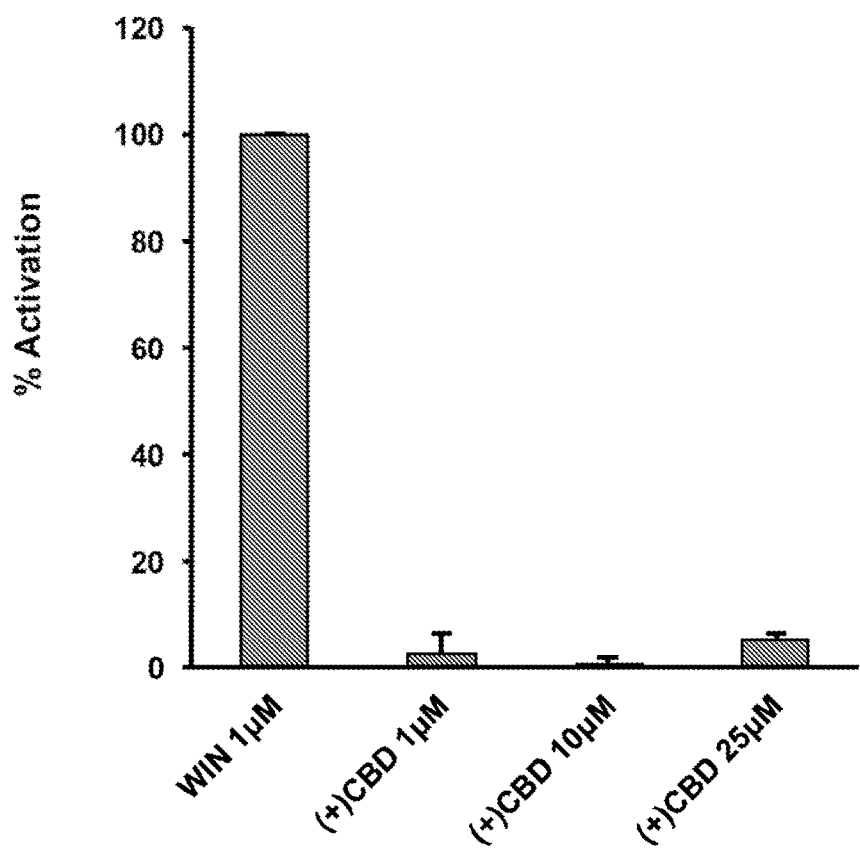
FIG. 6 shows the effect of (+)-CBD on $CB_1$ functional activity (agonistic activity) as evaluated in example 5.
Figure 7:
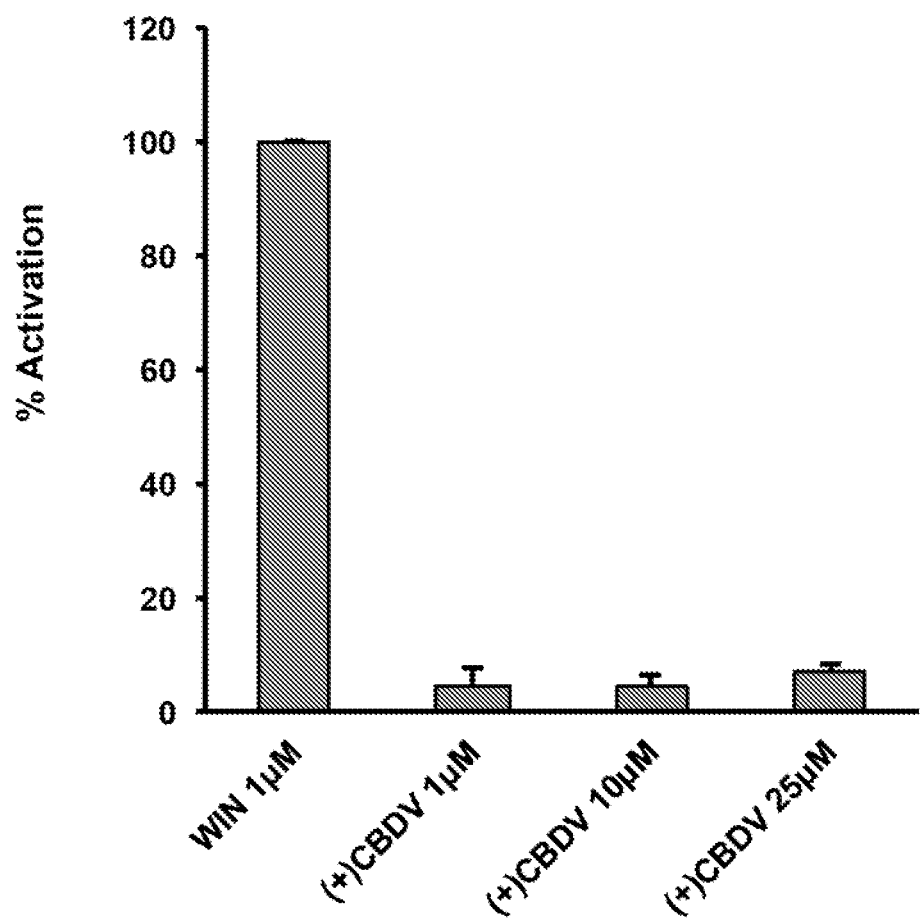
FIG. 7 shows the effect of (+)-CBDV on $CB_1$ functional activity (agonistic activity) as evaluated in example 5.
Figure 8:
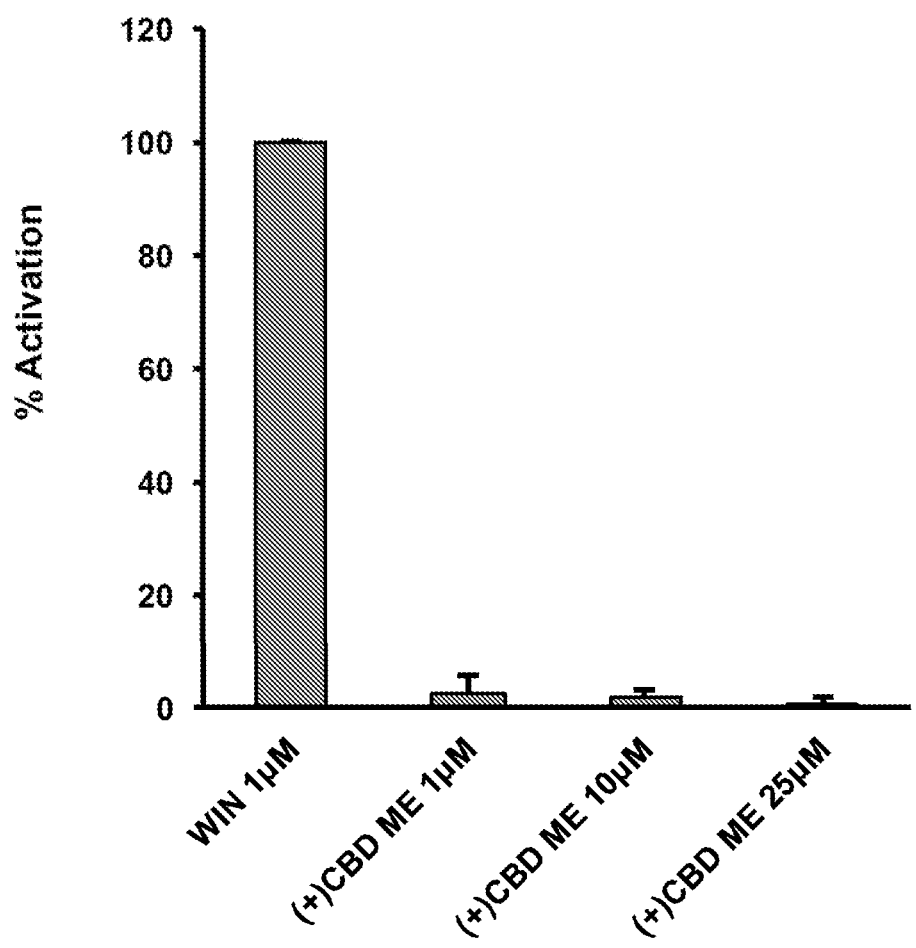
FIG. 8 shows the effect of (+)-CBD-ME on $CB_1$ functional activity (agonistic activity) as evaluated in example 5.
Figure 9:
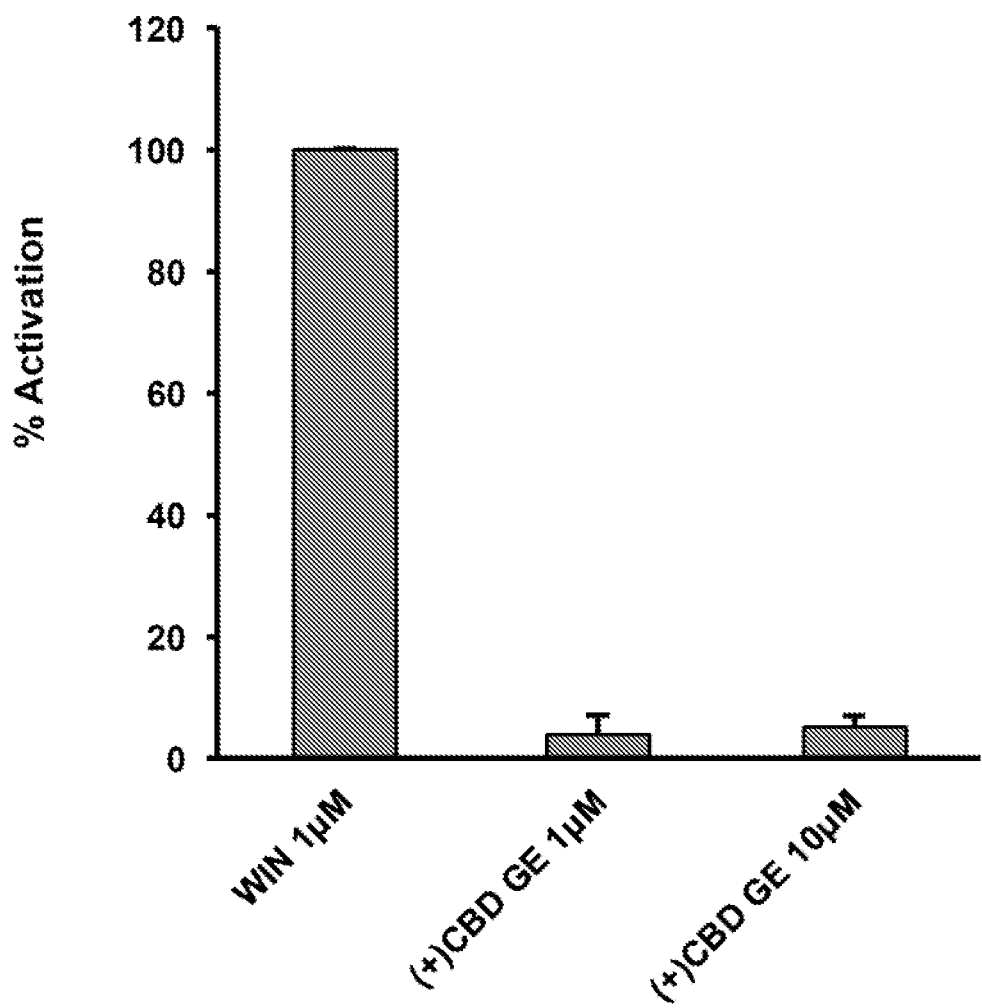
FIG. 9 shows the effect of (+)-CBD-GE on $CB_1$ functional activity (agonistic activity) as evaluated in example 5. (+)-CBD-GE shows cytotoxicity at 25 µM.
Figure 10:
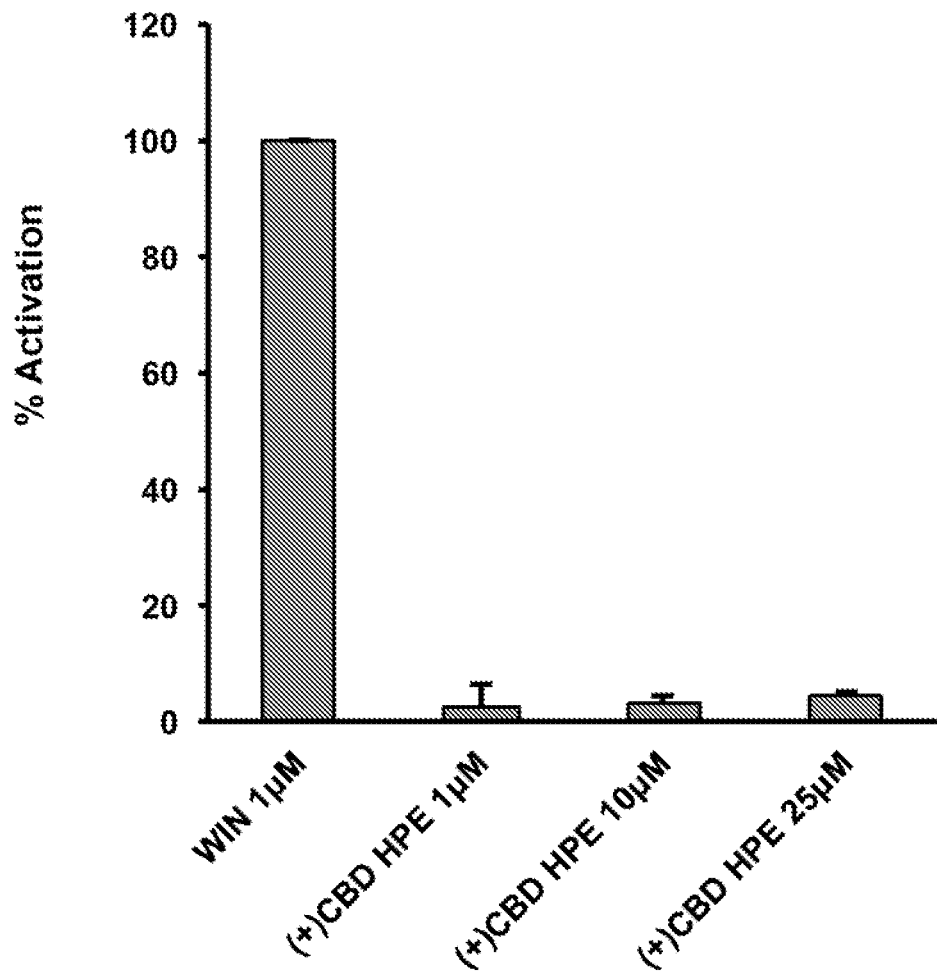
FIG. 10 shows the effect of (+)-CBD-HPE on $CB_1$ functional activity (agonistic activity) as evaluated in example 5.
Figure 11:
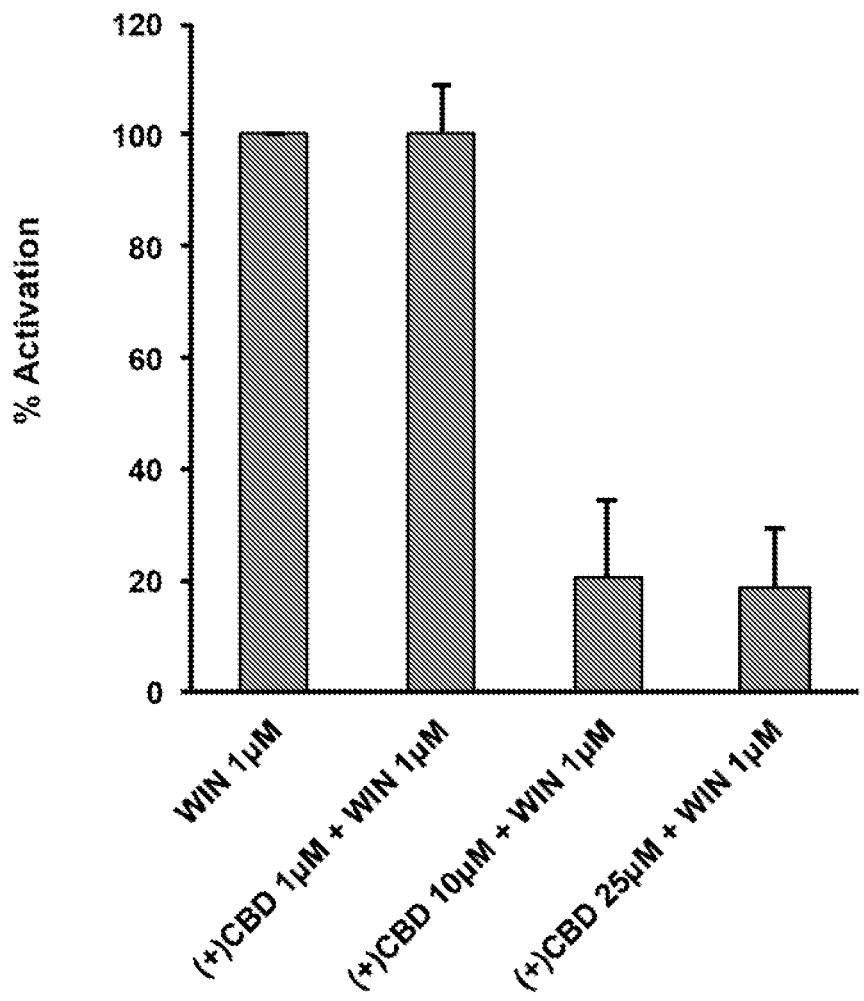
FIG. 11 shows the effect of (+)-CBD on $CB_1$ functional activity (antagonistic activity) as evaluated in example 5.
Figure 12:
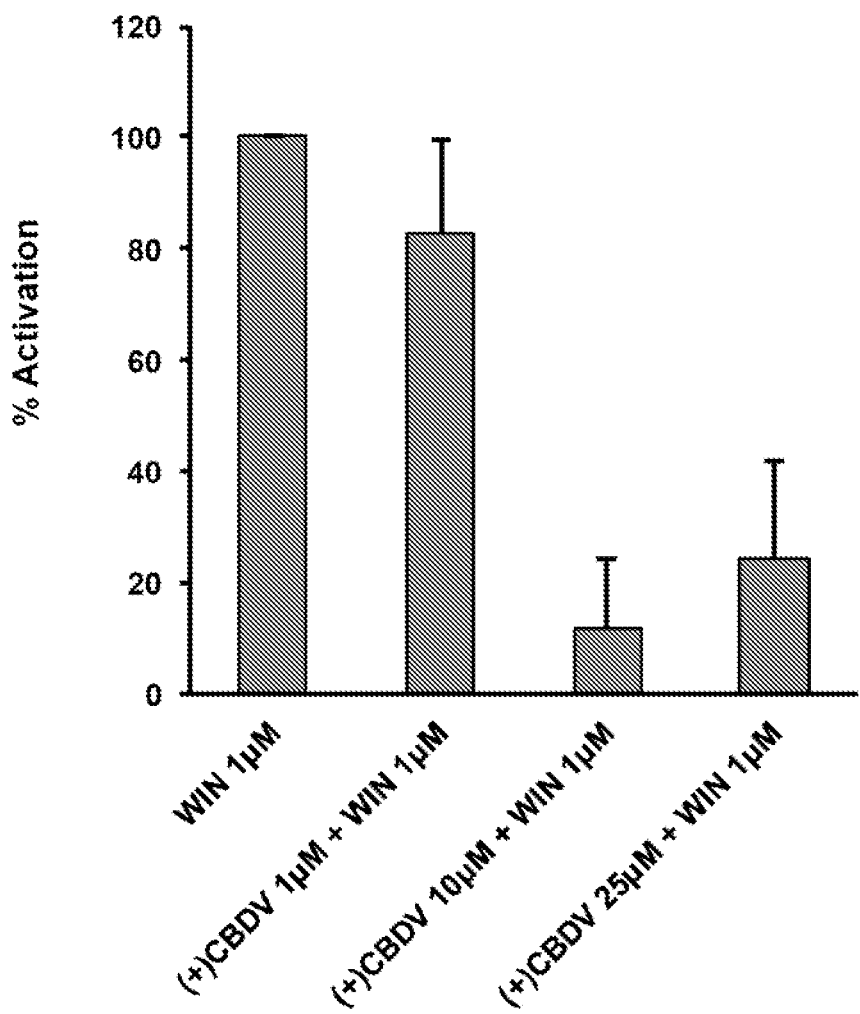
FIG. 12 shows the effect of (+)-CBDV on $CB_1$ functional activity (antagonistic activity) as evaluated in example 5.
Figure 13:
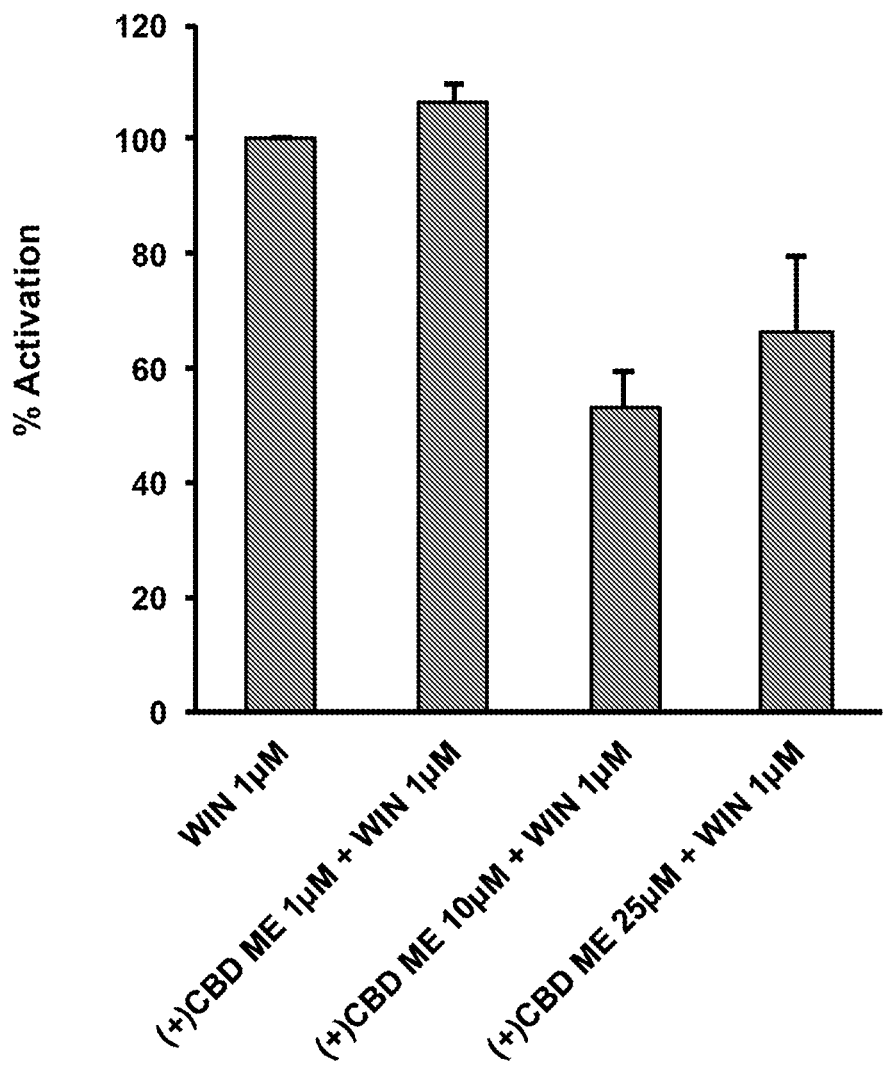
FIG. 13 shows the effect of (+)-CBD-ME on $CB_1$ functional activity (antagonistic activity) as evaluated in example 5.
Figure 14:
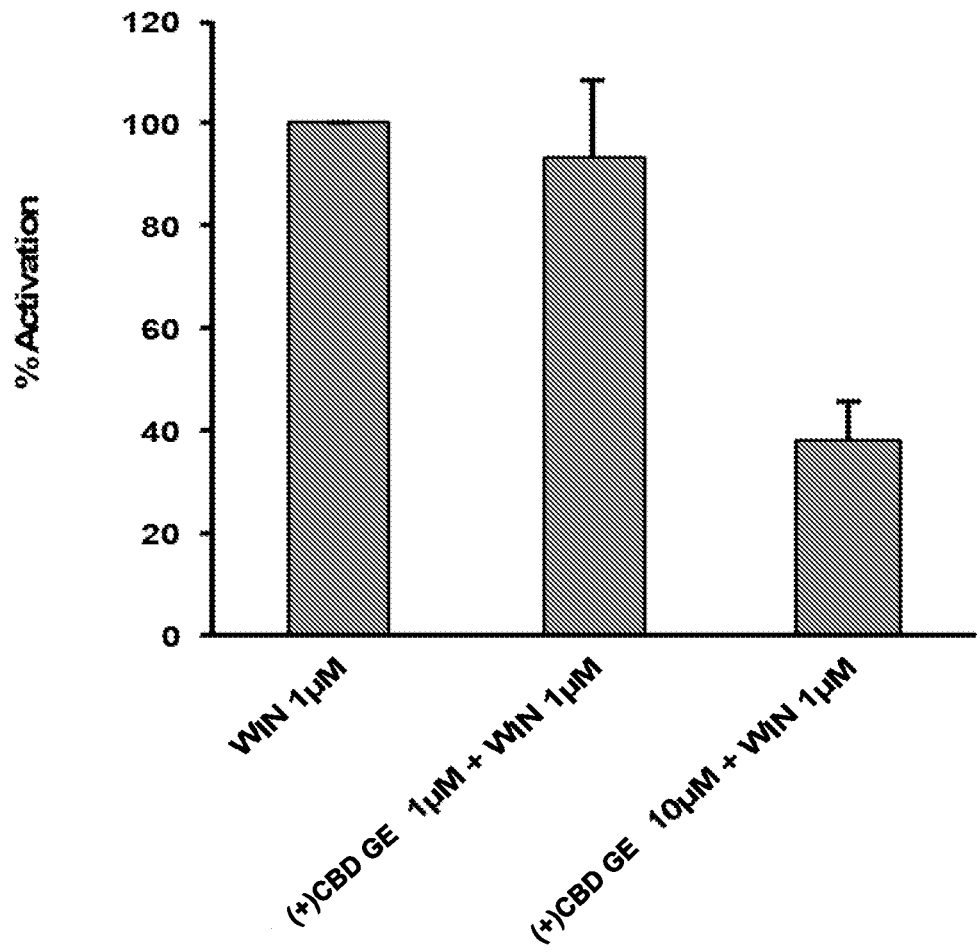
FIG. 14 shows the effect of (+)-CBD-GE on $CB_1$ functional activity (antagonistic activity) as evaluated in example 5. CBD-GE shows cytotoxicity at 25 µM.

The invention will be explained in more detail on the basis of the examples below.

EXAMPLE 1

Synthesis of (+)-CBD (3)

Scheme 4: Synthesis of (+)-CBD-ME (1)

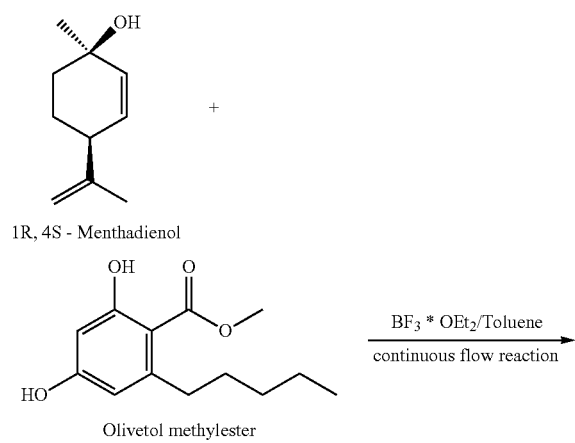

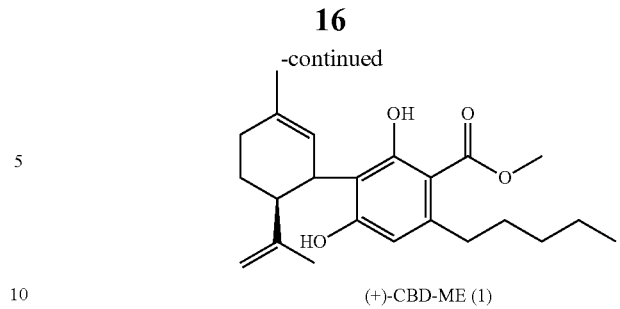

(+)-CBD-ME (1)

71.4 g (300 mMol) olivetol methylester and 50 g (330 mMol) 1R,4S-menthadienol were dissolved together with toluene to reach a combined volume of 400 ml→Solution A. 21.3 g (150 mMol) $BF_3$ etherate was dissolved with toluene to reach a volume of 300 ml→Solution B. Both reaction solutions were then put through two separate pump systems and the continuous flow reactor (rotation: 1200 U/min, solution A: 24 ml/min, solution B: 12 ml/min). Solution B started before and ended after solution A to guarantee that catalyst is always present in the reaction chamber. The reaction mixture was continuously collected in a 2 liter lab reactor (30° C. mantel temperature, 300 rpm) filled with 700 ml saturated $NaHCO_3$ solution. The aqueous solution was discarded; the organic solution was washed at 45 degrees 4 times with 250 mL of 1% NaOH solution. After washing, the organic solution was evaporated to dryness to give 94.58 g of raw (+)-CBD methylester (purity=78%, yield 68%). The raw compound can be used further without purification.

Exemplary Purification of (+)-CBD ME (1):

The crude product was purified by flash chromatography (eluent system cyclohexane/ethyl acetate=40/1 v/v). GC purity: 99.1%. Chiral GC analysis: enantiomeric excess 99% (for enantiomeric pure starting material). $^1$H NMR (400 MHz, $CDCl_3$) δ 11.98 (s, 1H), 6.50 (s, 1H), 6.21 (s, 1H), 5.55 (s, 1H), 4.52 (p, J=2.4, 1.4 Hz, 1H), 4.41-4.36 (m, 1H), 4.16-4.06 (m, 1H), 3.90 (s, 3H), 2.89-2.79 (m, 1H), 2.78-2.69 (m, 1H), 2.44-2.33 (m, 1H), 2.29-2.15 (m, 1H), 2.09 (dq, J=17.9, 4.0, 2.5 Hz, 1H), 1.84-1.76 (m, 2H), 1.80-1.77 (m, 3H), 1.72-1.68 (m, 3H), 1.57-1.46 (m, 2H), 1.38-1.28 (m, 4H), 0.89 (t, J=6.8 Hz, 3H). $^{13}$C NMR (101 MHz, $CDCl_3$) δ 172.62, 163.11, 159.91, 147.23, 145.94, 140.19, 124.06, 114.38, 111.49, 111.23, 103.91, 51.73, 46.66, 36.83, 35.40, 32.10, 31.14, 30.24, 27.84, 26.92, 23.71, 22.55, 18.83, 14.10.

Scheme 5: Synthesis of (+)-CBD (3) via (+)-CBD GE (2)

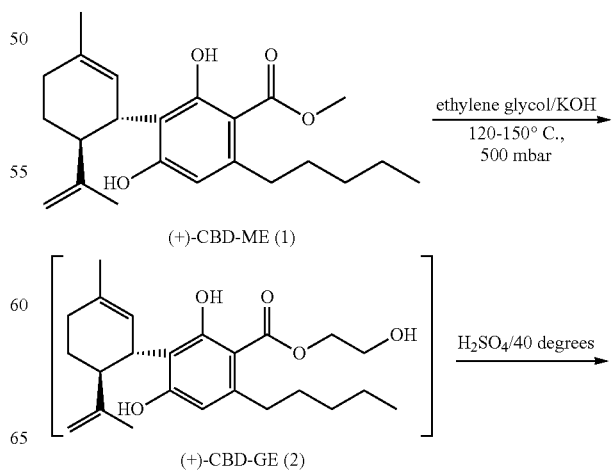

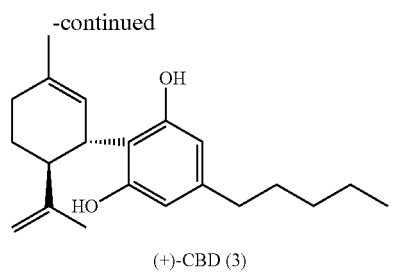

(+)-CBD (3)

49.2 g (103 mMol) (+)-CBD-ME (1) was dissolved at 60 degrees in 250 mL ethylene glycol and poured in a 1 L lab reactor. 5.7 g potassium hydroxide was added and the reaction mixture was started to heat under stirring to 120 degrees and a vacuum of 500 mbar. Accumulated volatile side products were distilled off. After 2 hours the reaction temperature was increased to 150 degrees and the temperature was kept for additional 3 hours. The reaction mixture was cooled to 80 degrees, following addition of 400 mL water and 130 mL n-heptane. The temperature was further decreased to 40 degrees, following the slow addition of 1.2 mL of sulfuric acid (50%) until a pH of approx. 6. The layers were separated, the organic layer was washed once with 250 mL of water and once with 250 ml of sodium hydroxide solution (0.05%). The organic layer was dried over Na$_2$SO$_4$ and then evaporated to dryness. Yield: 30.3 g, GC purity: 53%.

Exemplary Isolation and Purification of (+)-CBD GE (2):

A sample of the reaction mixture was taken after 2 hours at 120 degrees, quenched with n-heptane and water and neutralized with sulfuric acid (10% w/w). The layers were separated and the organic layer was evaporated to dryness. The crude (+)-CBD-GE (2) was purified by flash chromatography (eluent system n-heptane/ethyl acetate=4/1 v/v). GC purity: 97.8%. Chiral GC analysis: enantiomeric excess 99% (for enantiomeric pure starting material). $^1$H NMR (400 MHz, CDCl$_3$) δ 11.88 (s, 1H), 6.53 (s, 1H), 6.23 (s, 1H), 5.55 (s, 1H), 4.54-4.50 (m, 1H), 4.50-4.44 (m, 2H), 4.40-4.36 (m, 1H), 4.14-4.06 (m, 1H), 3.98-3.92 (m, 2H), 2.88 (ddd, J=13.1, 8.8, 6.7 Hz, 1H), 2.78 (ddd, J=13.1, 8.7, 6.8 Hz, 1H), 2.39 (q, J=8.1 Hz, 1H), 2.29-2.16 (m, 1H), 2.10 (dq, J=17.9, 3.6 Hz, 1H), 1.84-1.76 (m, 2H), 1.80-1.77 (m, 3H), 1.71 (s, 3H), 1.60-1.49 (m, 2H), 1.36-1.29 (m, 4H), 0.89 (t, J=6.8 Hz, 3H). $^{13}$C NMR (101 MHz, CDCl$_3$) δ 172.39, 163.27, 160.12, 147.20, 145.86, 140.31, 123.97, 114.52, 111.68, 111.28, 103.71, 66.73, 61.19, 46.65, 46.01, 36.98, 35.39, 32.06, 31.48, 30.24, 27.83, 23.72, 22.68, 18.82, 14.09.

Purification of (+)-CBD (3):

The crude (+)-CBD was purified in this instance by flash chromatography (eluent system cyclohexane/ethyl acetate=20/1 v/v). Flash chromatography can be substituted with thin layer distillation, following crystallisation from n-heptane. GC purity: 99,8%. Chiral GC analysis: enantiomeric excess 99% (for enantiomeric pure starting material and for starting materials with up to 5% 4R-menthadienol enantiomer). $^1$H NMR (400 MHz, CDCl$_3$) δ 6.35-6.09 (m, 2H), 5.97 (s, 1H), 5.57 (dt, J=2.8, 1.6 Hz, 1H), 4.66 (p, J=1.6 Hz, 2H), 4.56 (d, J=2.0 Hz, 1H), 3.85 (ddp, J=10.7, 4.5, 2.3 Hz, 1H), 2.48-2.41 (m, 2H), 2.38 (ddd, J=10.6, 3.7 Hz, 1H), 2.30-2.17 (m, 1H), 2.09 (ddt, J=17.9, 5.1, 2.4 Hz, 1H), 1.88-1.81 (m, 1H), 1.79 (dt, J=2.6, 1.2 Hz, 3H), 1.78-1.72 (m, 1H), 1.65 (t, J=1.1 Hz, 3H), 1.62-1.50 (m, 2H), 1.37-1.22 (m, 4H), 0.88 (t, J=7.0 Hz, 3H). 13C NMR (101 MHz, CDCl$_3$) δ 156.07, 153.90, 149.41, 143.06, 140.07, 124.12, 113.76, 110.84, 109.84, 108.00, 7.35, 77.03, 76.71, 46.15, 37.28, 35.48, 31.50, 30.64, 30.41, 28.41, 23.69, 22.55, 20.54, 14.05.

EXAMPLE 2

Synthesis of (+)-CBD HPE (4)

Scheme 6: Synthesis of (+)-CBD HPE (4)

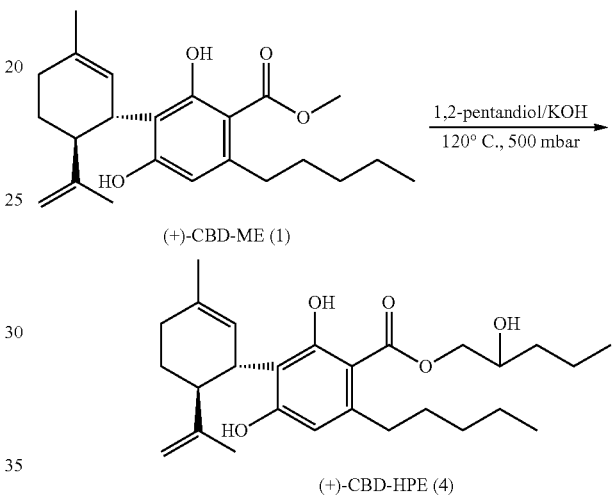

10 g (24 mMol) (+)-CBD-ME (1) was dissolved at 60 degrees in 250 mL 1,2-pentandiol and poured in a 1 L lab reactor. 1.1 g potassium hydroxide was added and the reaction mixture was started to heat under stirring to 120 degrees and a vacuum of 500 mbar. Accumulated volatile side products were distilled off. After 2 hours the reaction mixture was cooled to 80 degrees, following addition of 400 mL water and 130 mL n-heptane. The temperature was further decreased to room temperature and neutralized with sulfuric acid (10% w/w). The layers were separated, the organic layer was washed once with 250 mL of water, dried over Na$_2$SO$_4$ and evaporated to dryness. The crude product (+)-CBD-HPE (4) was purified by flash chromatography (eluent system cyclohexane/ethyl acetate=10/1 v/v). GC purity: 98%. Chiral GC analysis: enantiomeric excess 99% (for enantiomeric pure starting material). $^1$H NMR (400 MHz, DMSO-d$_6$) δ 11.61 (s, 1H), 9.89 (s, 1H), 6.20 (s,1H), 5.11-5.05 (m, 1H), 4.91-4.82 (m, 1H), 4.46 (d, J=2.7 Hz, 1H), 4.42 (dd, J=2.8, 1.5 Hz, 1H), 4.24-4.11 (m, 2H), 3.95-3.86 (m, 1H), 3.81-3.71 (m, 1H), 3.03 (td, J=11.4, 10.9, 3.0 Hz, 1H), 2.74 (s, 2H), 2.22-2.05 (m, 1H), 1.94 (dd, J=16.7, 4.1 Hz, 1H), 1.76-1.63 (m, 2H), 1.61 (t, J=1.8 Hz, 3H), 1.58 (s, 3H), 1.53-1.34 (m, 6H), 1.33-1.26 (m, 4H), 0.89 (t, J=7.0 Hz, 3H), 0.86 (t, J=6.7 Hz, 3H). $^{13}$C NMR (101 MHz, DMSO-d$_6$) δ 171.22, 162.07, 160.33, 148.61, 144.07, 130.72, 125.60, 114.82, 110.15, 109.84, 103.50, 68.95, 67.27, 43.32, 35.71, 35.61, 35.44, 31.36, 30.91, 30.13, 29.12, 23.13, 22.00, 18.88, 18.12, 13.86, 13.

EXAMPLE 3

Synthesis of (+)-CBDV (5)

Scheme 7: Synthesis of (+)-CBDV ME

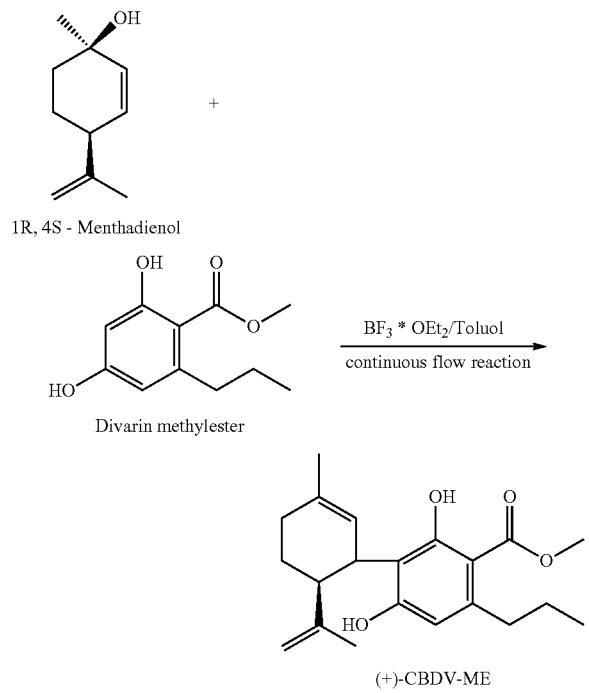

91 g (430 mMol) divarin methylester and 66 g (430 mMol) 4S-menthadienol were dissolved together with toluene to reach a combined volume of 610 ml→Solution A. 20 g (140 mMol) $BF_3$ etherate was dissolved with toluene to reach a volume of 177 ml→Solution B. Both reaction solutions were then put through two separate pump systems and the continuous flow reactor (rotation: 1200 U/min, solution A: 93 ml/min, solution B: 29 ml/min). The reaction mixture was continuously collected in a 2 liter lab reactor (30° C. mantel temperature, 300 rpm) filled with 750 ml saturated $NaHCO_3$ solution. The aqueous solution was discarded; the organic solution was washed at 40 degrees 7 times with 250 mL of 1% NaOH solution. After washing, the organic solution was evaporated to dryness to give 117 g of raw (+)-CBDV-ME (purity=81%, yield 70%). The raw compound was used further without purification.

Scheme 8: Synthesis of (+)-CBDV (5) via (+)-CBDV-GE

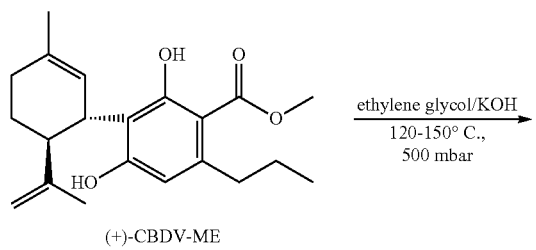

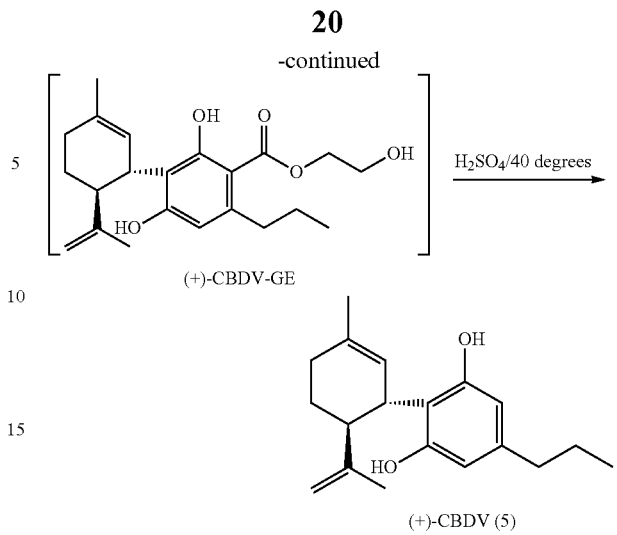

117 g (275 mMol) (+)-CBDV-ME was dissolved at 60 degrees in 150 mL ethylene glycol and poured in a 1 L lab reactor. 30.8 g (550 mMol) potassium hydroxide was dissolved in 100 ml ethylene glycol and added to the stirring solution. The reaction mixture was started to heat under stirring to 120 degrees and a vacuum of 500 mbar. Accumulated volatile side products were distilled off. After 2 hours the reaction temperature was increased to 150 degrees and the temperature was kept for additional 3 hours. The reaction mixture was cooled to 80 degrees, following addition of 550 mL water and 200 mL n-heptane. The temperature was further decreased to 40 degrees, following the slow addition of 45 g of sulfuric acid (50%) until a pH of approx. 6. The layers were separated, the aqueous layer was extracted once with 200 ml MTBE. Both organic layers were combined and evaporated to dryness to give 99 g of crude product. To the crude was added 23 g of Synalox oil and the resulting mixture was distilled over a thin layer distillation apparatus. The resulting distillate (62 g, according to GC analysis 83.4% product) was then crystallized from n-heptane. The resulting white crystals were recrystallized once more from n-heptane to give pure product. Yield: 27 g. GC purity: 99.6%. Chiral GC analysis: enantiomeric excess 99% (for enantiomeric pure starting material and for starting materials with up to 5% 4R-menthadienol enantiomer). $^1H$ NMR (400 MHz, $CDCl_3$) δ 6.37-6.08 (m, 2H), 5.98 (s, 1H), 5.57 (dt, J=2.8, 1.6 Hz, 1H), 4.71 (s, 1H), 4.66 (p, J=1.6 Hz, 1H), 4.55 (d, J=2.1 Hz, 1H), 3.85 (ddq, J=10.5, 4.5, 2.4 Hz, 1H), 2.46-2.38 (m, 2H), 2.45-2.34 (m, 1H), 2.30-2.17 (m, 1H), 2.09 (ddt, J=17.9, 5.1, 2.5 Hz, 1H), 1.87-1.81 (m, 1H), 1.79 (dd, J=2.8, 1.5 Hz, 3H), 1.77-1.72 (m, 1H), 1.65 (t, J=1.2 Hz, 3H), 1.64-1.52 (m, 2H), 0.90 (t, J=7.3 Hz, 3H). $^{13}C$ NMR (101 MHz, $CDCl_3$) δ 156.08, 153.82, 149.37, 142.78, 140.07, 124.13, 113.82, 110.85, 109.82, 108.11, 77.35, 77.04, 76.72, 46.17, 37.58, 37.25, 30.41, 28.41, 24.03, 23.69, 20.51, 13.81.

EXAMPLE 4

In Vitro Binding to $CB_1$ and $CB_2$ Receptors

Compounds with an expected profile as $CB_1$ and/or $CB_2$ receptor ligands were evaluated by competition studies that allow determining the affinity of these compounds (Ki values) for both receptors against a classical cannabinoid ligand. The competition studies were conducted with membranes transfected with either $CB_1$ or $CB_2$ receptors. For stock solutions the compounds were dissolved at concentrations of 50 and 100 mM and stored at −20° C.

Experimental Procedure

Membranes from human $CB_1$ or $CB_2$ receptor-transfected cells (RBHCB1M400UA and RBXCB2M400UA, respectively) were supplied by Perkin-Elmer Life and Analytical Sciences (Boston, Mass.). The values of $B_{max}$ and $K_d$ for the $CB_1$ or $CB_2$ receptor membranes are variable. The used batch showed the following $B_{max}$ and $K_d$ values, 1.9 pmol/mg membrane protein and 0.16 nM, respectively, for $CB_1$ receptor membranes, and 5.2 pmol/mg membrane protein and 0.18 nM, respectively, for $CB_2$ receptor membranes. The protein concentration for the $CB_1$ receptor membranes was 8.0 mg/ml, whereas for the $CB_2$ receptor membranes 4.0 mg/ml. The commercial membranes were diluted (1:20) with the binding buffer (50 mM TrisCl, 5 mM $MgCl_2.H_2O$, 2.5 mM EDTA, 0.5 mg/mL BSA and pH=7.4 for $CB_1$ binding buffer; 50 mM TrisCl, 5 mM $MgCl_2.H_2O$, 2.5 mM EGTA, 1 mg/mL BSA and pH=7.5 for $CB_2$ binding buffer). The radioligand was [$^3$H]-CP55940 (144 Ci/mmol; PerkinElmer) used at a concentration of 0.10 nM with a final volume of 200 μl for $CB_1$ binding and at a concentration of 0.15 nM with a final volume of 600 μl for $CB_2$ binding. 96-well plates and the tubes necessary for the experiment were siliconized with Sigmacote (Sigma). Membranes were resuspended in the corresponding buffer and were incubated with the radioligand and each compound for 90 min at 30° C. Non-specific binding was determined with 10 μM WIN55212-2 and 100% binding of the radioligand to the membrane was determined by its incubation with membrane and without any compound. Filtration was performed by a Harvester®filtermate (Perkin-Elmer) with Filtermat A GF/C filters pretreated with polyethylenimine 0.05%. After filtering, the filter was washed nine times with binding buffer, dried and a melt-on scintillation sheet (Meltilex™ A, Perkin Elmer) was melted onto it. Then, radioactivity was quantified by a liquid scintillation spectrophotometer (Wallac MicroBeta Trilux, Perkin-Elmer).

Results

Radioligand displacement assays were used to evaluate the affinity of the new compounds using membranes from cells (HEK293EBNA) transfected with the $CB_1$ or the $CB_2$ receptors and [$^3$H]-CP55940 as radioligand. The evaluation of the compounds was conducted in two phases. The first phase consisted in a simple screening with a unique and high concentration of each compound (40 μM). The data was collected from at least three experiments performed in triplicate. Only those compounds that are able to displace more than 50% the binding of [$^3$H]-CP55940 (0.10 nM for $CB_1$ and 0.15 nM for $CB_2$) were selected for the second phase. This consisted of a competition study with [$^3$H]CP55940 (0.10 nM for $CB_1$ and 0.15 nM for $CB_2$) and different concentrations of the selected compounds ($10^{-4}$-$10^{-11}$M). The data was analyzed, by using GraphPad Prism® version 5.01 (GraphPad Software Inc., San Diego, Calif., USA), for the calculation of Ki values expressed as mean±SEM of at least three experiments performed in triplicate for each point. The calculated Ki values are indicated in table 2. The binding profiles are shown in FIGS. 1-5.

TABLE 2

$CB_1$ and $CB_2$ binding activities of the compounds

| Compound | $CB_1$-Ki (nM) | $CB_2$-Ki (nM) | $CB_1$/$CB_2$ selectivity |
|---|---|---|---|
| (+)-CBD | 982 | 40.5 | 24.3 |
| (+)-CBDV | 294 | 33.1 | 8.9 |
| (+)-CBD-ME | 345 | 28.0 | 12.3 |
| (+)-CBD-GE | 359 | 12.9 | 27.8 |
| (+)-CBD-HPE | 3.1 | 0.8 | 3.9 |

EXAMPLE 5

Functional Assays on Transfected Cells

After it was established that the compounds expressed binding affinity towards the cannabinoid receptors, their function on these receptors (agonism, antagonism) was analyzed.

Experimental Procedure

HEK 293T-$CB_1$ and HEK 293T-$CB_2$ cells (stably transfected with $CB_1$ and $CB_2$ cDNAs) ($10^5$/ml) were incubated in 24-well plates and transiently transfected with 0.5 μg/ml of the plasmid CRE-Luc that contains six consensus cAMP responsive elements (CRE) linked to firefly luciferase. Transient transfections were performed with Rotifect (Carl Roth GmbH, Karlsruhe, Germany) according to the manufacturer's instructions and harvested 24 h after transfection.

For $CB_1$ agonistic activity the transfected cells were stimulated either with increasing concentrations of the test compounds or with WIN 55,212-2 (positive control for $CB_1$), during 6 h and then luciferase activity was measured in the cell lysates (1-2). Forskolin is an adenylate cyclase activator that is used at 10 μM as a positive control of cAMP signaling pathway activated by a $CB_1$ receptor-independent mechanism.

For $CB_1$ antagonistic activity the $CB_1$ cells were pre-incubated with the test compounds during 15 min and then stimulated with WIN 55,212-2 for 6 h.

To measure $CB_2$ agonistic activity, HEK293T-$CB_2$-CRE-luc cells were treated either with increasing concentrations of the test compounds or with WIN 55,212-2 (positive control for $CB_2$), for 15 min and then with Forskolin (10 μM) during 6 h.

For $CB_2$ antagonistic activity in cells the potential repression of Forskolin-induced CRE-luc inhibition induced by the compounds was analyzed. As positive controls AM630 or SR144588 were used, two known $CB_2$ antagonists.

After six hours of stimulation the cells were lysed (in 25 mM Tris-phosphate pH 7.8, 8 mM $MgCl_2$, 1 mM DTT, 1% Triton X-100, and 7% glycerol) and luciferase activity was measured using an Autolumat LB 9501 (Berthold Technologies, Bad Wildbad, Germany) following the instructions of the luciferase assay kit (Promega, Madison, Wis.). The background obtained with the lysis buffer was subtracted in each experimental value, and the specific transactivation expressed as fold induction over basal levels (CRE-Luc).

Results $CB_1$ Agonistic Activity

HEK 293T-$CB_1$ cells were transfected with the CRE-Luc plasmid and 24 h later stimulated with either Win-55,212-2 (1 μM, positive control) or the test compounds for six hours. The negative control (untreated cells, 0% activation) is not listed. It was found that none of the 5 compounds tested showed $CB_1$ agonistic activity (FIGS. 6-10).

CB$_1$ Antagonistic Activity

Figure 15:
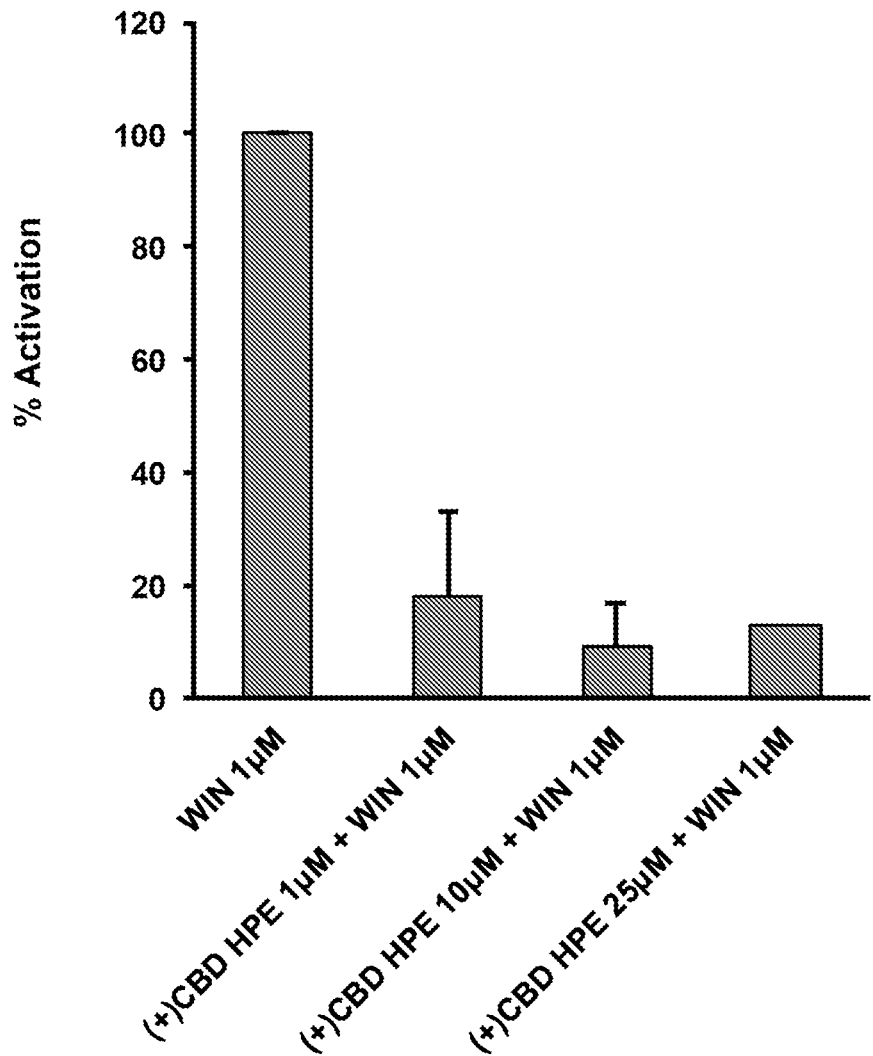
FIG. 15 shows the effect of (+)-CBD-HPE on $CB_1$ functional activity (antagonistic activity) as evaluated in example 5.

HEK 293T-CB$_1$ cells were transfected with the CRE-Luc plasmid and 24 h later stimulated with either Win 55,212-2 (1 µM positive control) in the presence or the absence of the test compounds for six hours. The negative control (untreated cells, 0% activation) is not listed. It was found that all the compounds tested showed CB$_1$ antagonistic activity (FIGS. 11-15), with (+)-CBD-HPE as the most potent CB$_1$ antagonist (FIG. 15).

CB$_2$ Agonistic Activity

Figure 16:
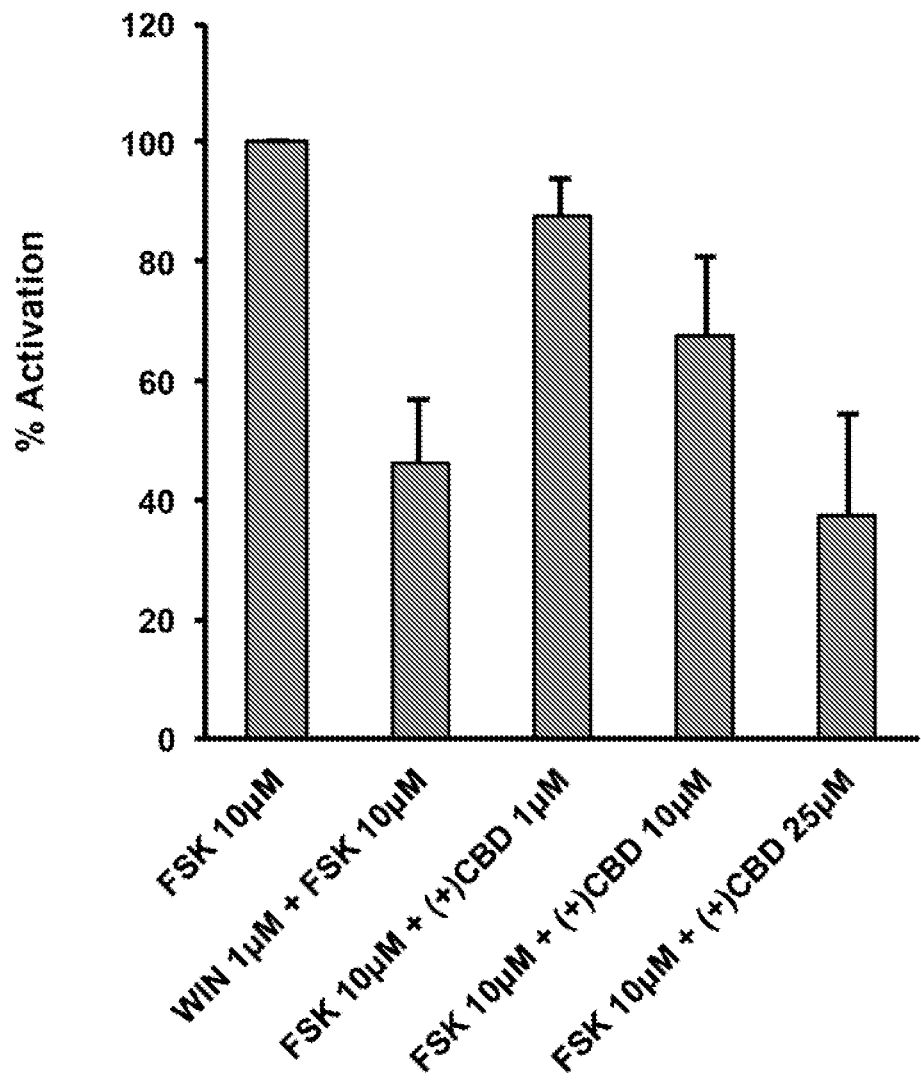
FIG. 16 shows the effect of (+)-CBD on $CB_2$ functional activity (agonistic activity) as evaluated in example 5.
Figure 17:
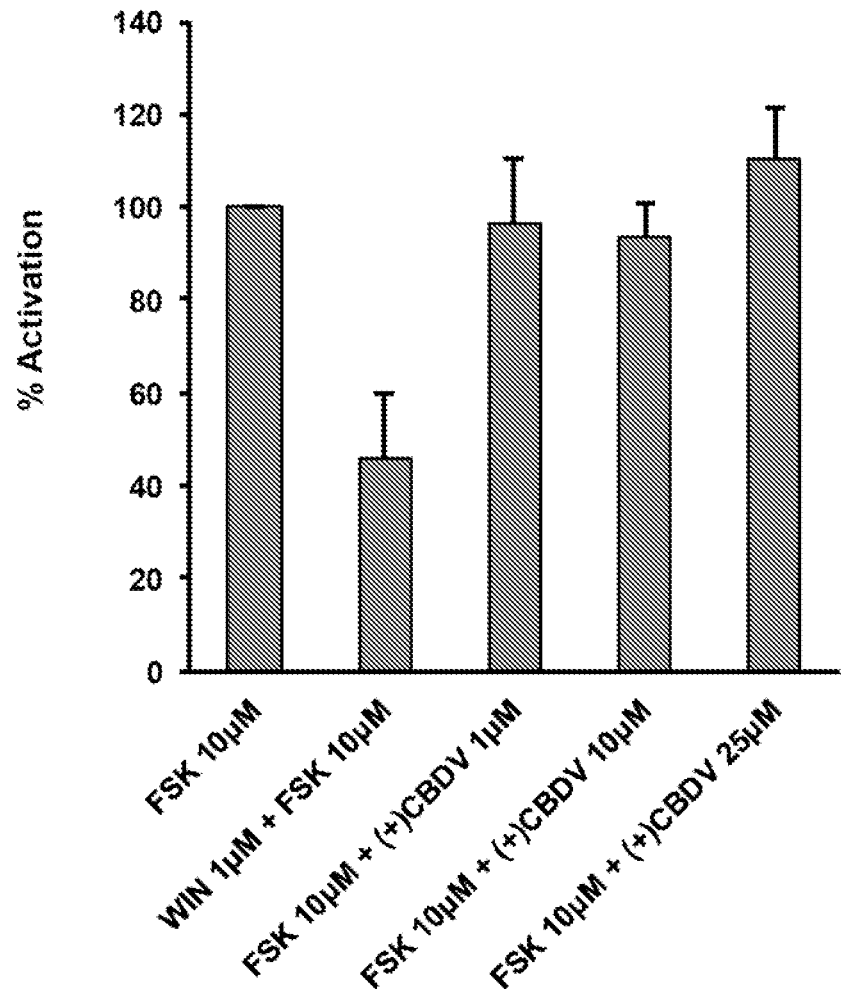
FIG. 17 shows the effect of (+)-CBDV on $CB_2$ functional activity (agonistic activity) as evaluated in example 5.
Figure 18:
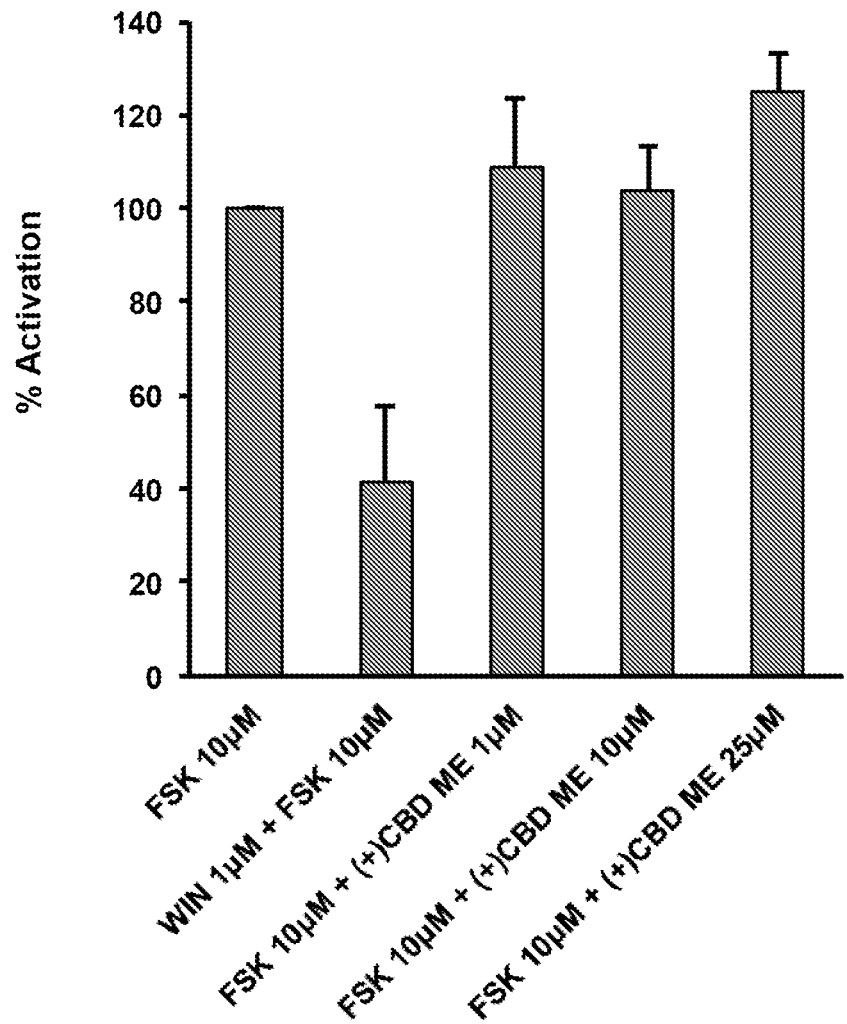
FIG. 18 shows the effect of (+)-CBD-ME on $CB_2$ functional activity (agonistic activity) as evaluated in example 5.
Figure 19:
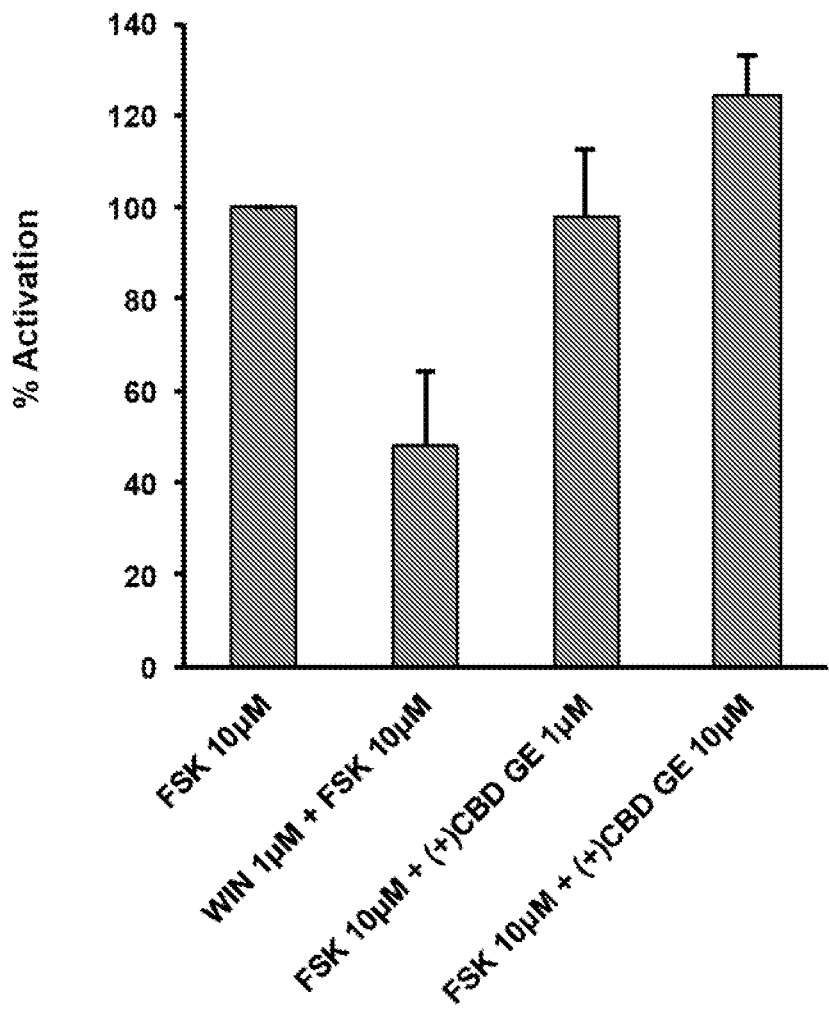
FIG. 19 shows the effect of (+)-CBD-GE on $CB_2$ functional activity (agonistic activity) as evaluated in example 5.
Figure 20:
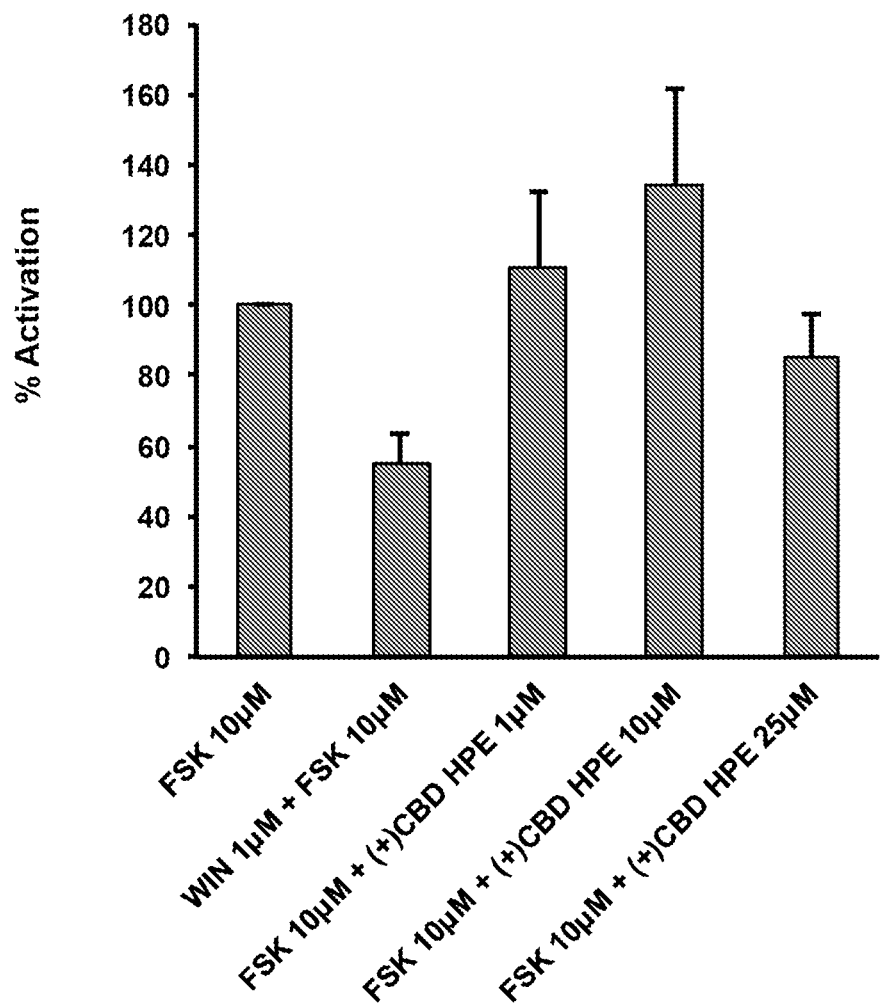
FIG. 20 shows the effect of (+)-CBD-HPE on $CB_2$ functional activity (agonistic activity) as evaluated in example 5.
Figure 21:
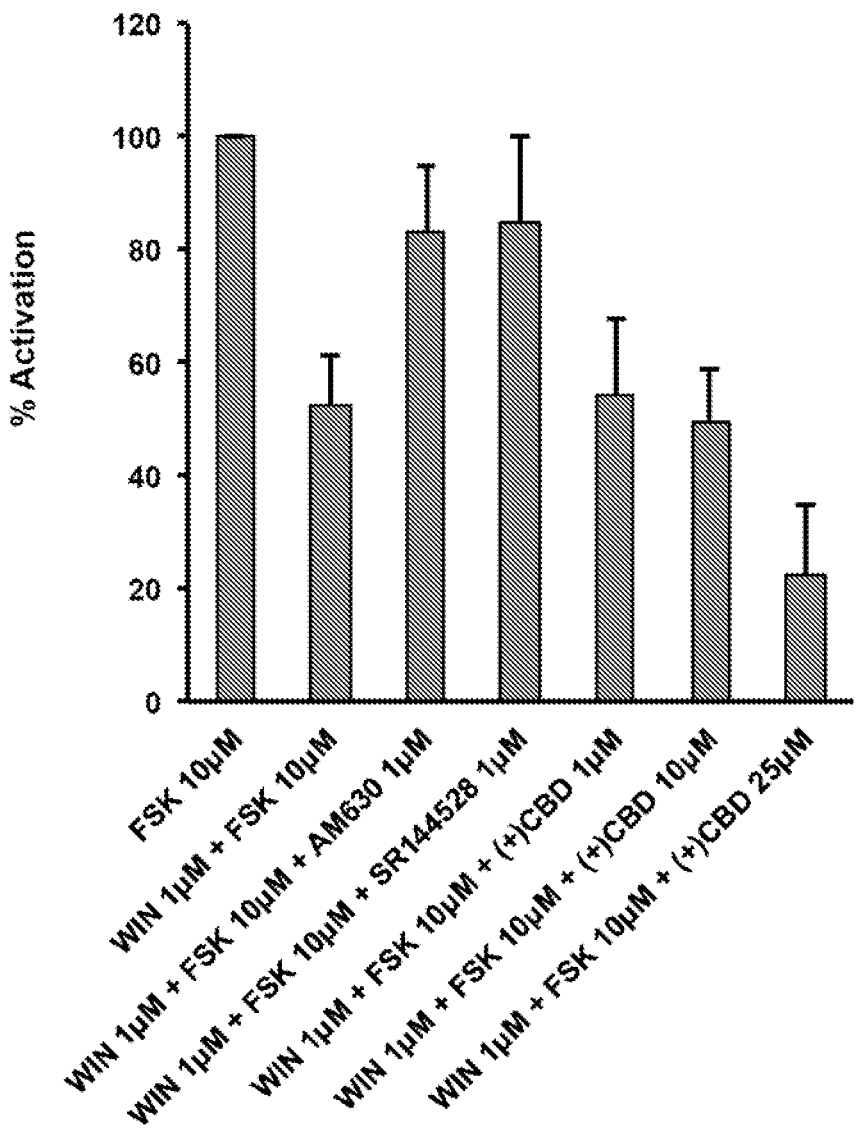
FIG. 21 shows the effect of (+)-CBD on $CB_2$ functional activity (antagonistic activity) as evaluated in example 5.
Figure 22:
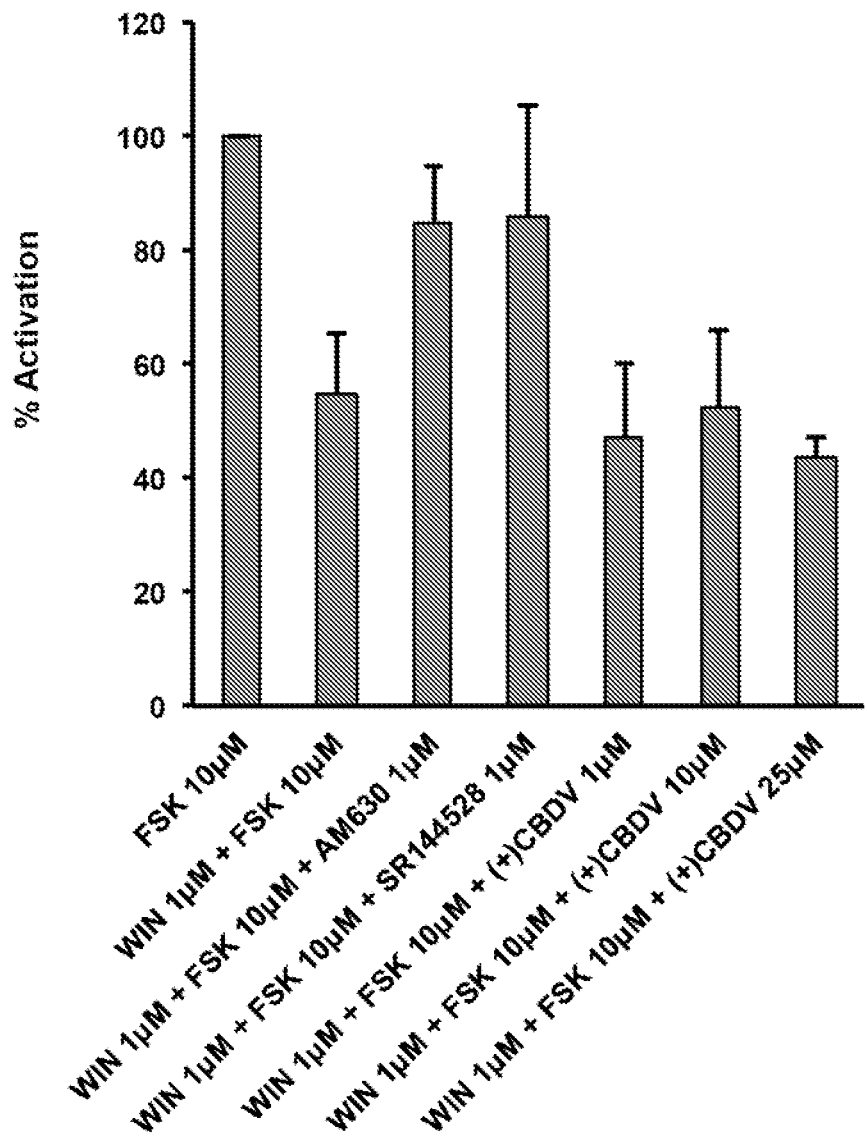
FIG. 22 shows the effect of (+)-CBDV on $CB_2$ functional activity (antagonistic activity) as evaluated in example 5.
Figure 23:
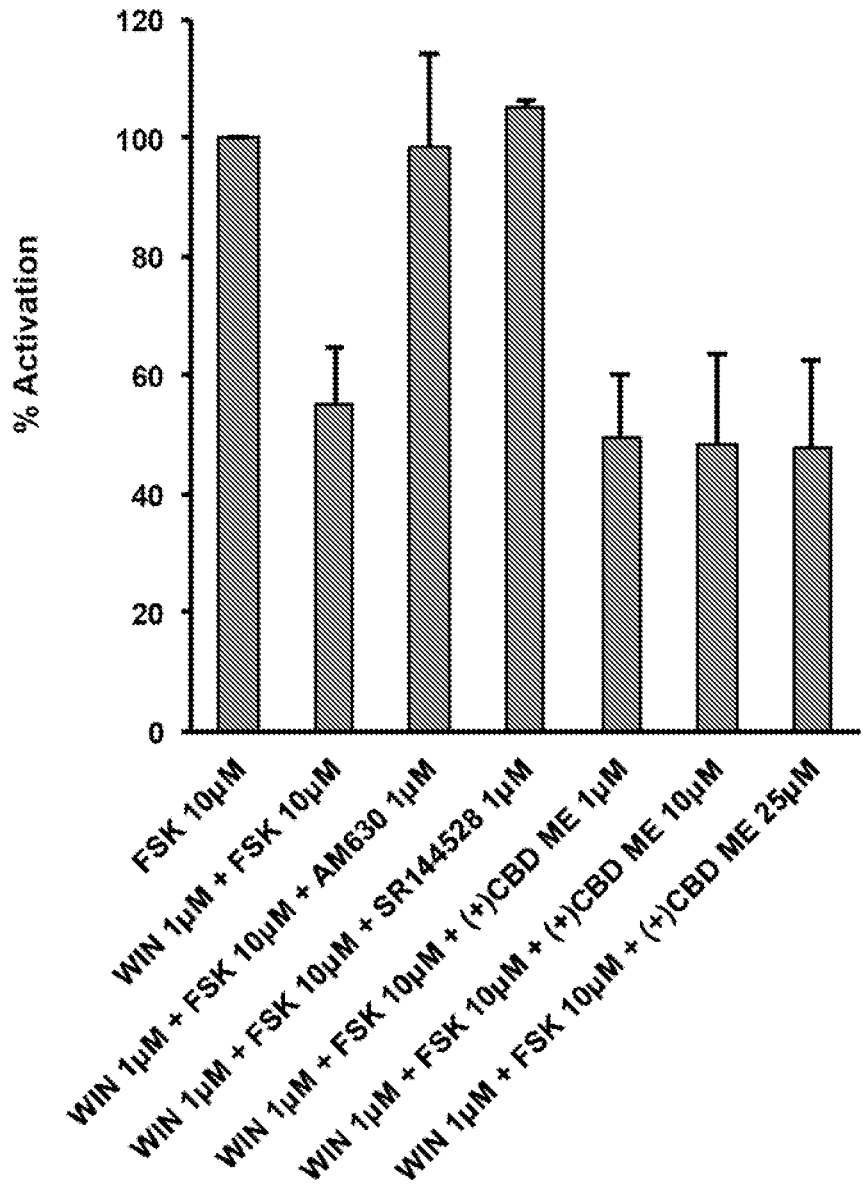
FIG. 23 shows the effect of (+)-CBD-ME on $CB_2$ functional activity (antagonistic activity) as evaluated in example 5.
Figure 24:
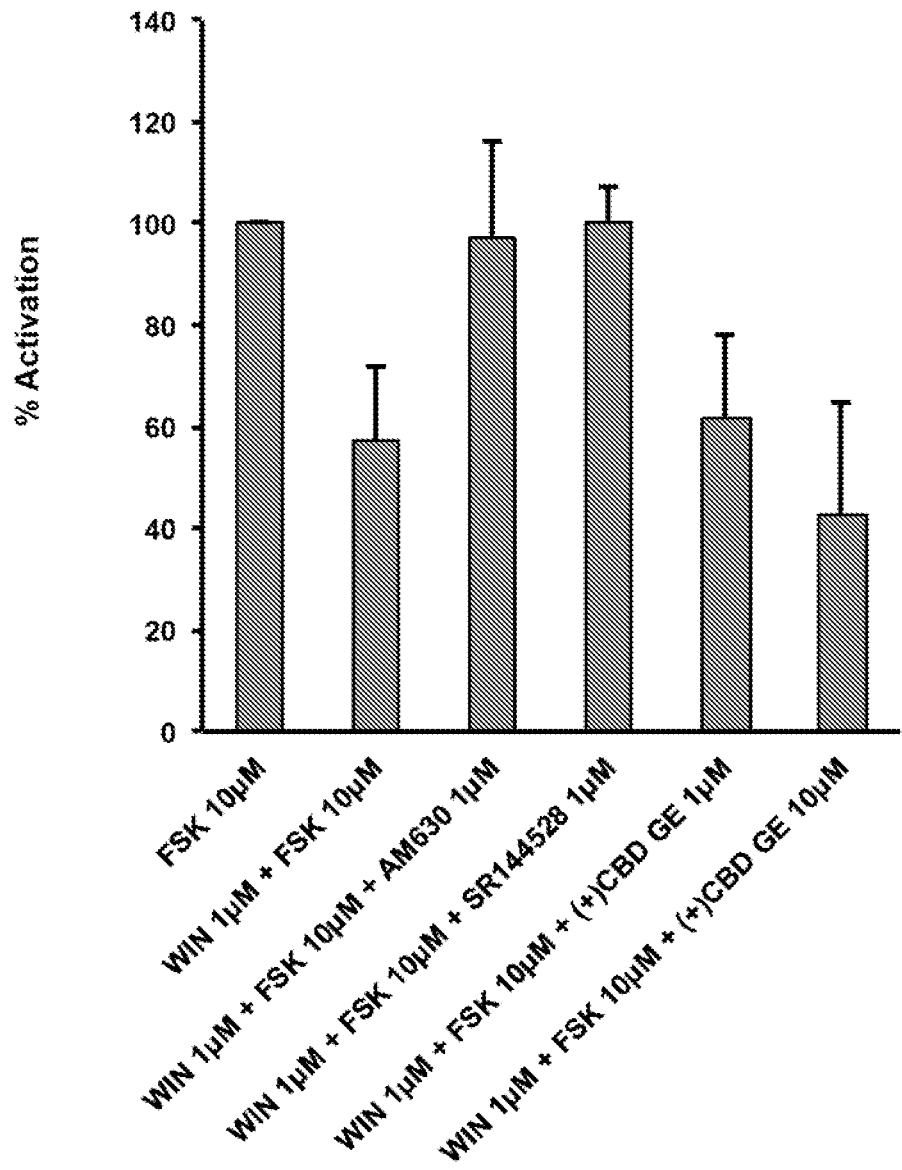
FIG. 24 shows the effect of (+)-CBD-GE on $CB_2$ functional activity (antagonistic activity) as evaluated in example 5.
Figure 25:
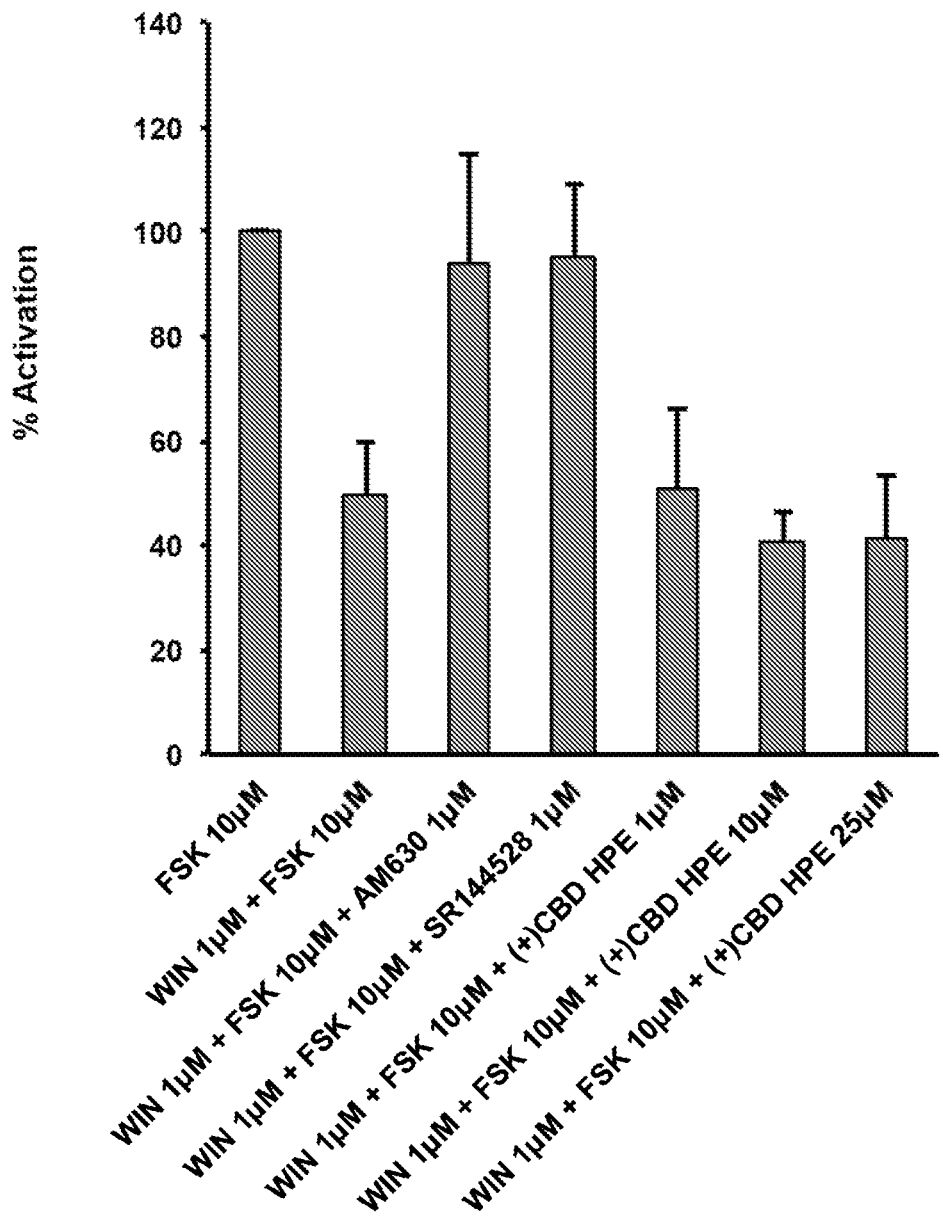
FIG. 25 shows the effect of (+)-CBD-HPE on $CB_2$ functional activity (antagonistic activity) as evaluated in example 5.

HEK 293T-CB2 cells were transfected with the CRE-Luc plasmid and 24 h later stimulated with either forskolin (10 µM, positive control) in the absence or the presence of WIN 55,212-2 or the test compounds for six hours. The negative control (untreated cells, 0% activation) is not listed. (+)-CBD (FIG. 16) and (+)-CBD-HPE (FIG. 20) showed some CB$_2$ agonistic activity at higher concentrations. The other compounds tested were negative for this activity (FIGS. 17-19).

CB$_2$ Antagonistic Activity

The potential antagonistic activities of the compounds on the CB$_2$ receptor were studied in the following. WIN 55,212-2 repression in Forskolin-induced CRE-Luc inhibition was prevented in the presence of either AM630 or SR144588, two known CB$_2$ antagonists. The negative control (untreated cells, 0% activation) is not listed. None of the compound tested showed CB$_2$ antagonistic activity (FIGS. 21-25).

supplemented with 10% human serum (Hexcell, Berlin, Germany, SP2080). After counting the number of cells in a particle counter (Euro Diagnostics, Krefeld, Germany), cells were seeded in 24-well plates for enzyme linked immunosorbent assay (ELISA) (2.2 mio. cells/well) or 96-well plates at a density of 2×104 cells/well for cell viability testing, and incubated at 37° C. with 5% CO$_2$. The medium and the non-adherent cells (lymphocytes) were removed and fresh RPMI-1640 medium containing 1% human serum added. Enriched monocytes were then ready to be used for the experiments. Primary human fibroblasts and HaCat keratinocytes were obtained from the Uniklinik Freiburg. All cells were maintained in supplemented DMEM (Invitrogen, Life-Technologies, Darmstadt, Germany) medium containing 10% FBS (Bio&Sell, Feucht, Germany) and 1% antibiotics penicillin/streptomycin (from Invitrogen, DMEM complete medium) at 37° C. in a humidified atmosphere of 5% CO$_2$.

Cell viability: Cells were incubated with the cannabinoids (3 doses, n=4) for 24 h. Cytotoxicity was analyzed by Alamar Blue staining (formazan). Then cells were washed once with 100 µl PBS, and 100 µl of medium-Alamar Blue-Mix (90% medium, 10% Alamar Blue, DAL1025, Thermo Fisher) was then added to each well. The plate was then incubated at 37° C. for 2 h in a humidified 5% CO$_2$ atmosphere, and the color reaction determined using a 96-well plate reader (Berthold, Offenburg, Germany, excitation 544 nm, emission 590 nm).

TABLE 3

CB$_1$ and CB$_2$ agonism/antagonism of the tested compounds

| COMPOUND | MOLECULAR WEIGHT (MW) | CB1 (agonism) | CB1 (antagonism) | CB2 (agonism) | CB2 (antagonism) |
|---|---|---|---|---|---|
| (+)-CBD | 314.5 | — | + | + | — |
| (+)-CBDV | 286.4 | — | + | — | — |
| (+)-CBD-ME | 372.5 | — | + | — | — |
| (+)-CBD-GE | 402.5 | — | + | — | — |
| (+)-CBD-HPE | 444.6 | — | + | (+) | — |

EXAMPLE 6

Bioactivity Study

The test compounds were dissolved in DMSO (10 mg/ml stock solution) and diluted in media for the in the following described experiments.

Experimental Procedure

Cell cultures: Human primary monocytes were extracted from the whole blood of medically healthy volunteers, who provided written informed consent at the local blood bank (University Hospital of Freiburg, Germany), following a standardized protocol (gradient preparation, Lymphocytes separation medium, PAN Biotech, P04-60125, Aidenbach, Germany) using completely endotoxin-free cultivation. Using 50 ml tubes, 25 ml Pancoll was loaded with 25 ml of blood (buffy coats). The gradient was established by centrifugation at 1800 rpm, 20° C. for 40 min with slow acceleration and deceleration. Peripheral blood mononuclear cells in the interphase were carefully removed and re-suspended in 50 ml pre-warmed phosphate-buffered saline (PBS) (Pan Biotech, P04-36500), followed by centrifugation for 10 min at 1600 rpm and 20° C. The supernatant was discarded and the pellet washed in 50 ml PBS and centrifuged as described above. The pellet was then re-suspended in 50 ml RPMI-1640 low-endotoxin medium Determination of inflammatory molecules in fibroblasts: Primary human fibroblasts were cultivated as described above and seeded (500000 cells/well) in 24-well plates. Cells were incubated with IL-1beta (Roche, Mannheim, Germany, 10 U/ml) in absence and presence of the cannabinoids (5 doses, n=3) for 24 h. Unstimulated cells served as a negative control. 24 h after cell stimulation, supernatants were removed, centrifuged and investigated for IL-6, PGE2, and IL-8 concentrations by ELISAs according to the manufacturer's protocol (PGE2 from Cayman/Biomol, Hamburg, Germany; IL-6, and IL-8 from Immuno-tools, Frisoythe, Germany). The respective extinction is determined using a 96-well plate reader (Berthold, Offenburg, Germany).

Determination of MMPs and TIMPs in keratinocytes: Keratinocytes (HaCat) were cultivated as described above. Cells were seeded in 24-well plates incubated with Poly I:C (InvivoGen, San Diego, Calif.; USA, 10 µg/ml) in absence and presence of the cannabinoids (5 doses, n=3) for 24 h. Unstimulated cells served as a negative control. 24 h after cell stimulation, supernatants were removed, centrifuged and investigated for MMP1, MMP9 and TIMP1 concentrations by ELISAs according to the manufacturer's protocol (from Biotechne, Wiesbaden, Germany). The respective extinction was determined using a 96-well plate reader (Berthold, Offenburg, Germany).

Measurement of cytokines and PGE2 in primary human monocytes: Cells were incubated with LPS (Sigma-Aldrich, Taufkirchen, Germany, 10 ng/ml) for 24 h. The cannabinoids (5 doses) were added 30 min before LPS treatment. After 24 h, supernatants were removed, centrifuged and investigated for IL-1beta, IL-8, IL-6, TNFalpha, MMP9, isoprostane, and PGE2 concentrations in EIAs (PGE2 and isoprostane, from Cayman/Biomol, Hamburg, Germany) or ELISAs (IL-1beta, Hiss, Freiburg, Germany; TNFalpha, IL-6 and IL-8, ImmunoTools, Frysoithe, Germany, MMP9, Biotechne, Wiesbaden, Germany) using manufacturer's protocol. The respective extinction was determined using a 96-well plate reader (Berthold, Offenburg, Germany). Each dose was analyzed 4 times in two buffy coats from 2 different donors (2 buffy coats used from 2 different healthy blood donors with final n=4 values).

Results

Effects on Cell Viability in Human Monocytes

Figure 26:
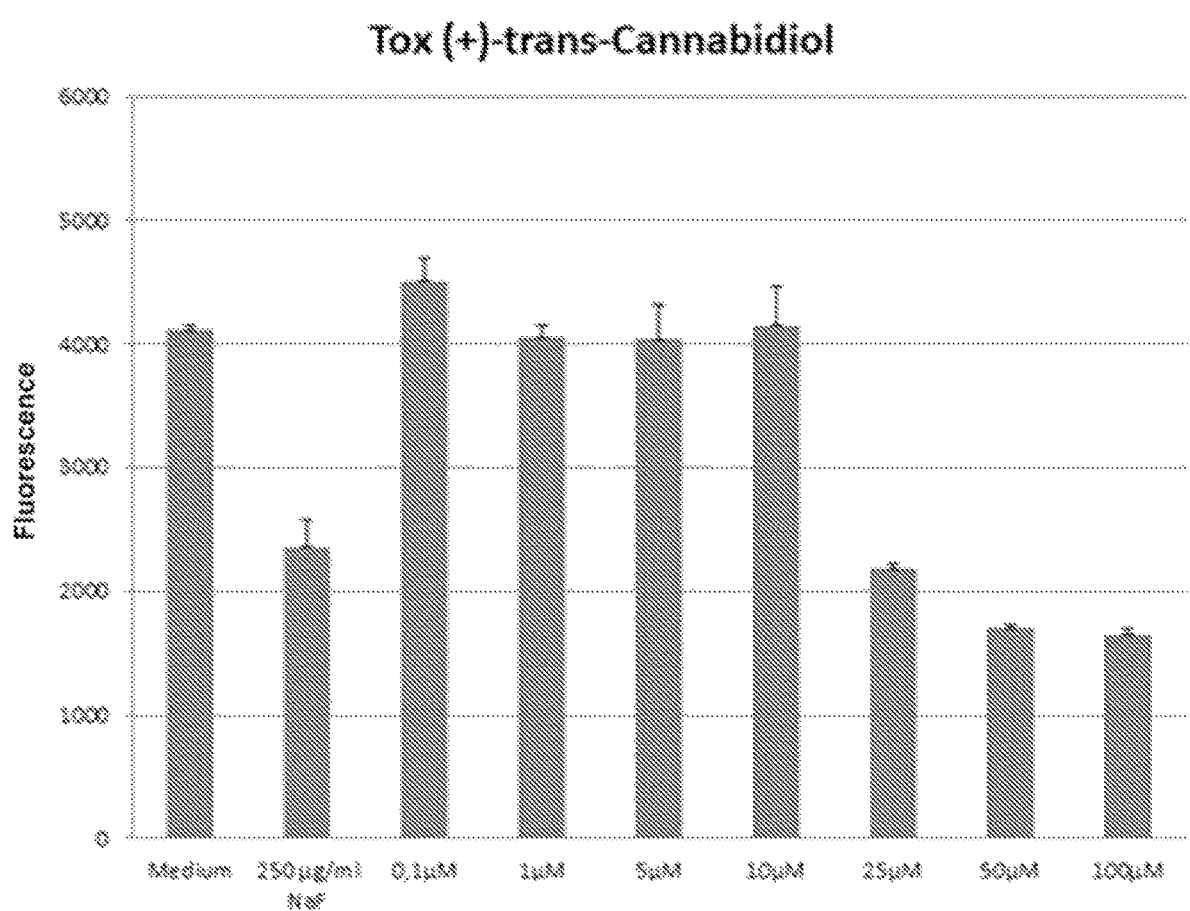
FIG. 26 shows the effects of (+)-CBD on cell viability in human monocytes as evaluated in example 6.
Figure 27:
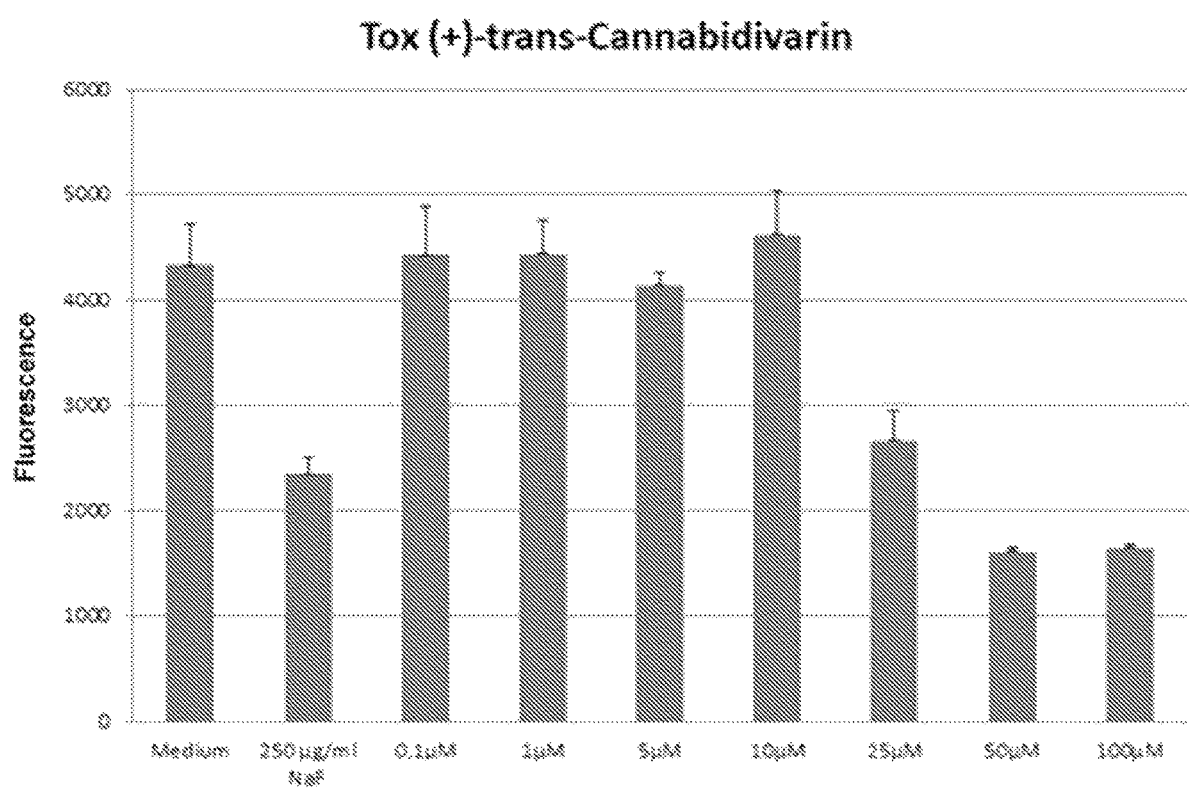
FIG. 27 shows the effects of (+)-CBDV on cell viability in human monocytes as evaluated in example 6.
Figure 28:
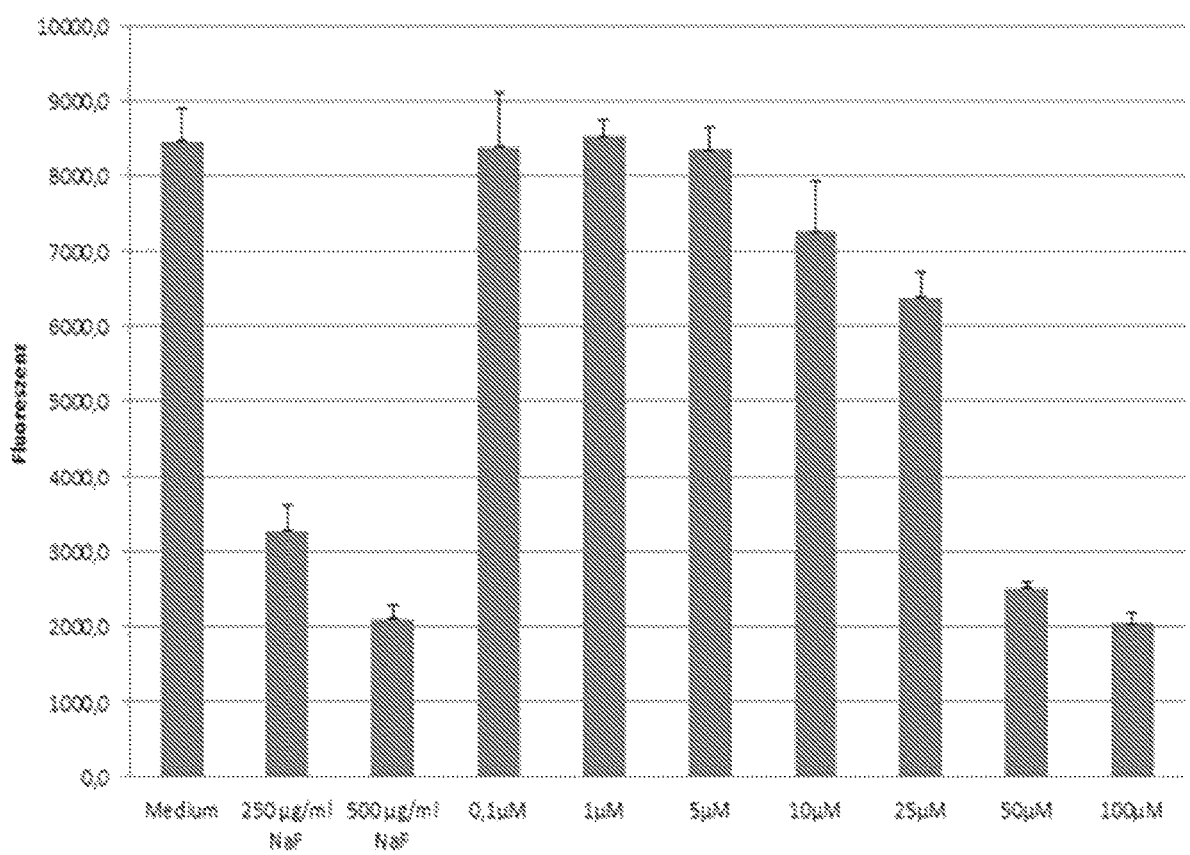
FIG. 28 shows the effects of (+)-CBD-ME on cell viability in human monocytes as evaluated in example 6.
Figure 29:
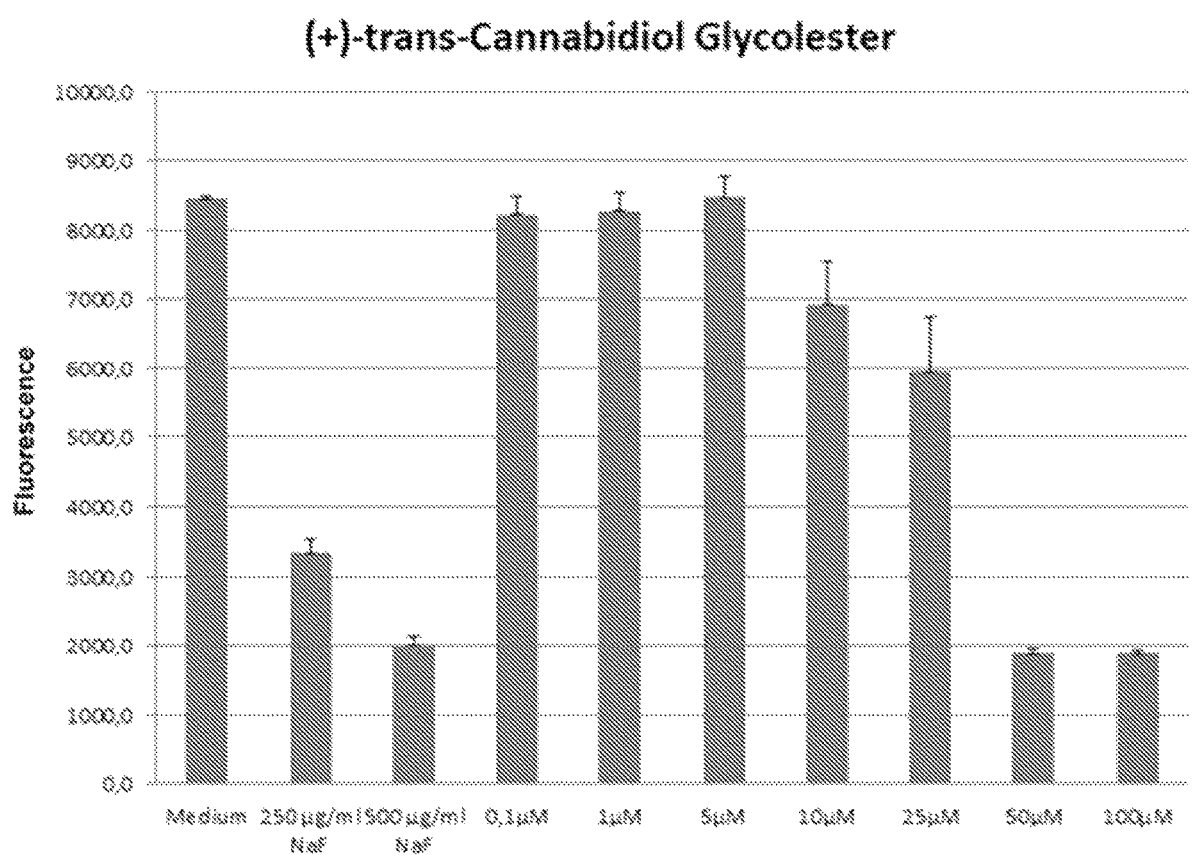
FIG. 29 shows the effects of (+)-CBD-GE on cell viability in human monocytes as evaluated in example 6.
Figure 30:
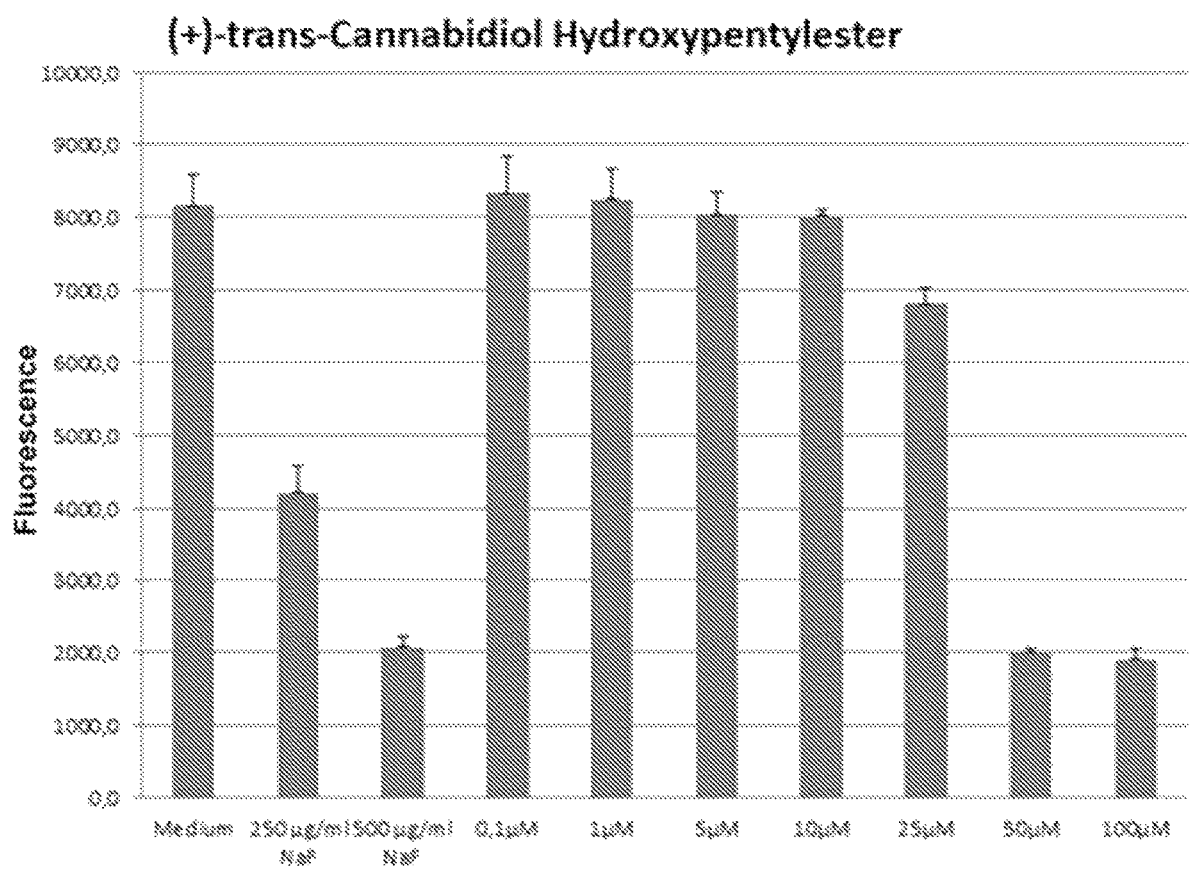
FIG. 30 shows the effects of (+)-CBD-HPE on cell viability in human monocytes as evaluated in example 6.

Cytotoxicity assays were performed in primary human monocytes. (+)-CBD and (+)-CBDV affected cell viability starting in the doses of 25 µM and higher (FIGS. 26+27), the other three cannabinoids starting with 50 µM (FIGS. 28-30). To be able to compare the activity of the five cannabinoids, 25 µM were used as highest dose.

Effects on LPS-Induced Inflammatory Parameters in Human Monocytes

Figure 31:
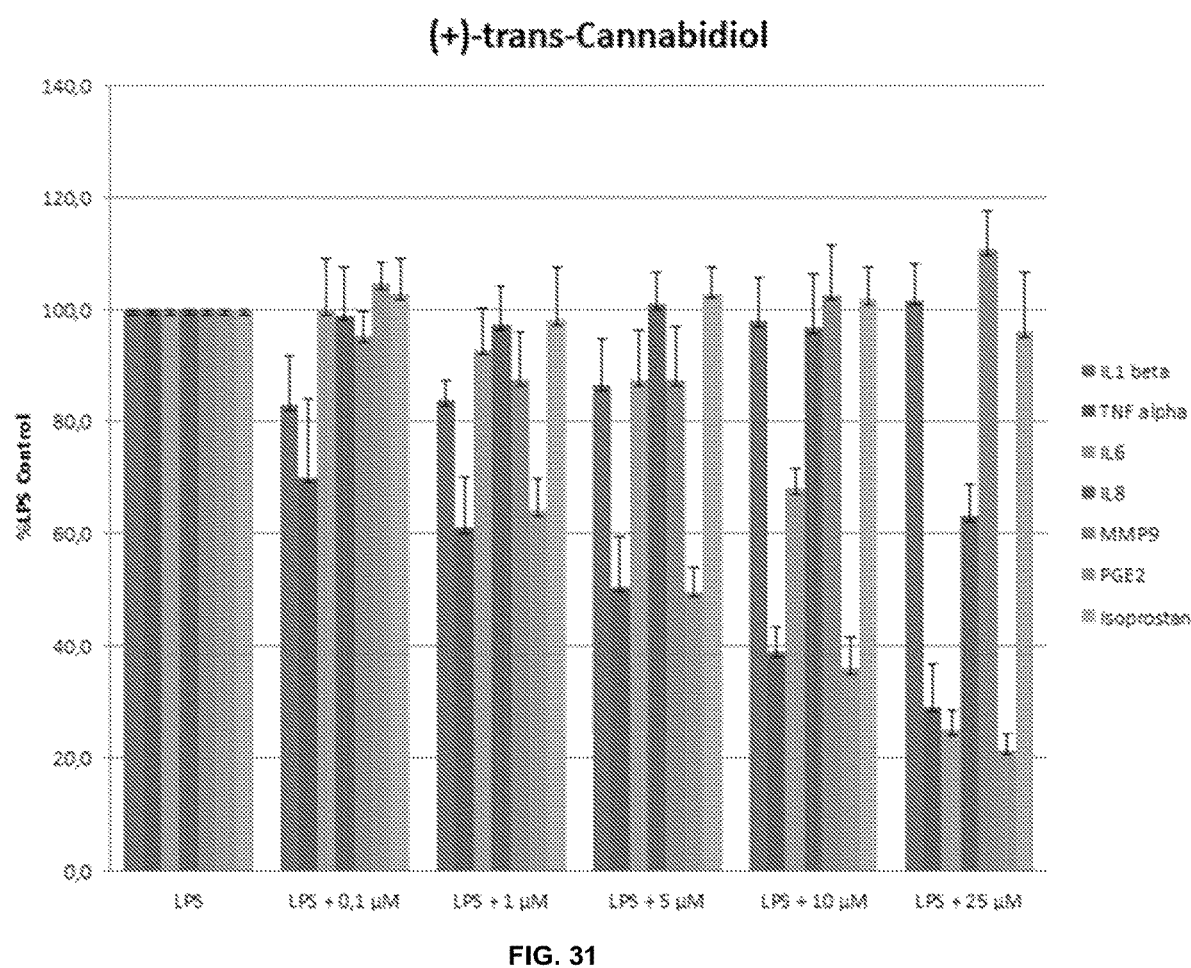
FIG. 31 shows the effects of (+)-CBD on inflammatory parameters in LPS-treated human monocytes as evaluated in example 6. The columns for each concentration indicate from left to right: IL1 beta, TNF alpha, IL6, IL8, MMP9, PGE2 and Isoprostan.

As shown in FIG. 31, (+)-CBD potently inhibited LPS-stimulated TNFalpha and PGE2 release starting at 0.1 µM (TNFalpha) and 1 µM (PGE2) with maximal effects using 25 µM, which showed an inhibition of around 80%. LPS-induced IL-6 was inhibited in the doses of 5 to 25 µM, IL-8 only in the dose of 25 µM, whereas LPS-mediated IL-1beta, MMP9 and isoprostane were not affected by (+)-CBD. The non-inhibiting effects on these 3 parameters suggest that the use of 25 µM is not killing the cells and thus affecting the other parameters.

Figure 32:
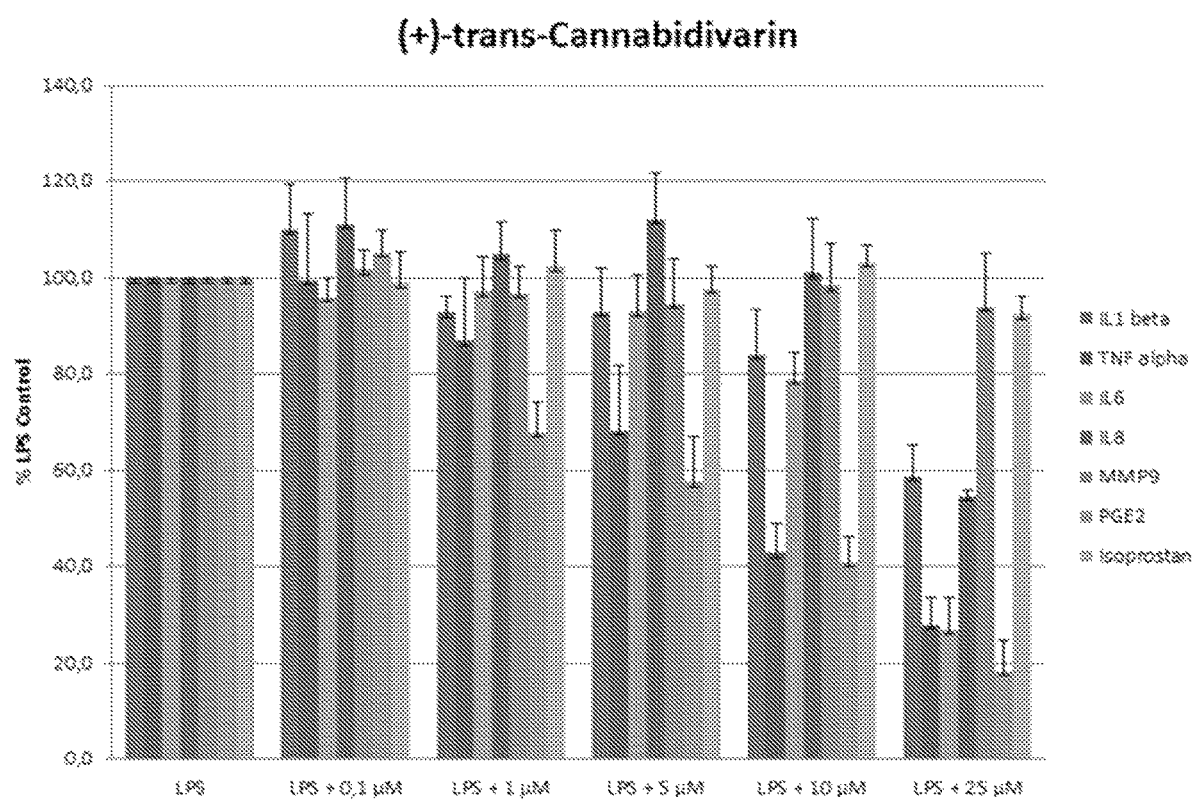
FIG. 32 shows the effects of (+)-CBDV on inflammatory parameters in LPS-treated human monocytes as evaluated in example 6. The columns for each concentration indicate from left to right: IL1 beta, TNF alpha, IL6, IL8, MMP9, PGE2 and Isoprostan.

(+)-CBDV showed comparable effects to (+)-CBD besides a weaker effect on TNFalpha and a slight effect on IL-1beta in the highest dose (FIG. 32).

Figure 33:
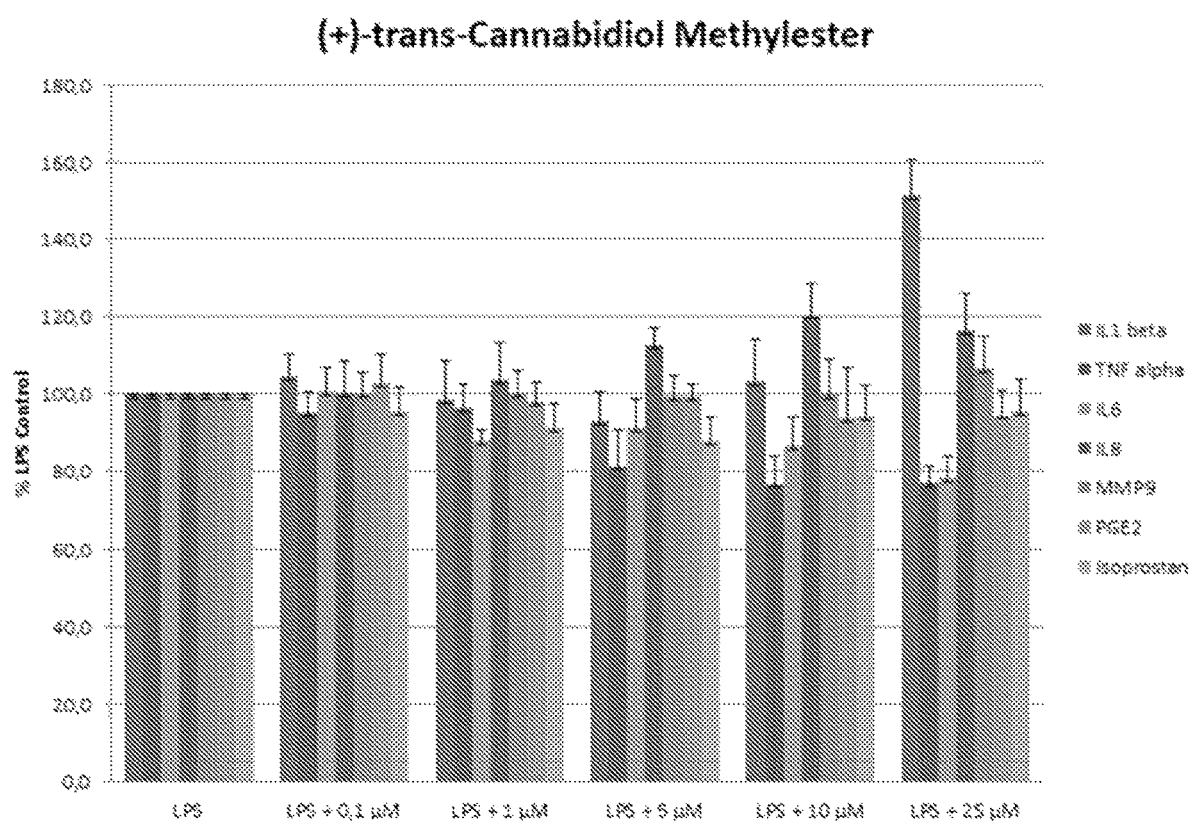
FIG. 33 shows the effects of (+)-CBD-ME on inflammatory parameters in LPS-treated human monocytes as evaluated in example 6. The columns for each concentration indicate from left to right: IL1 beta, TNF alpha, IL6, IL8, MMP9, PGE2 and Isoprostan.

(+)-CBD-ME only slightly inhibited LPS-induced IL-6 and TNFalpha with around 20%, but increased the chemokine IL-8 in the doses of 5-25 µM and IL-1beta in the dose of 25 µM (FIG. 33).

Figure 34:
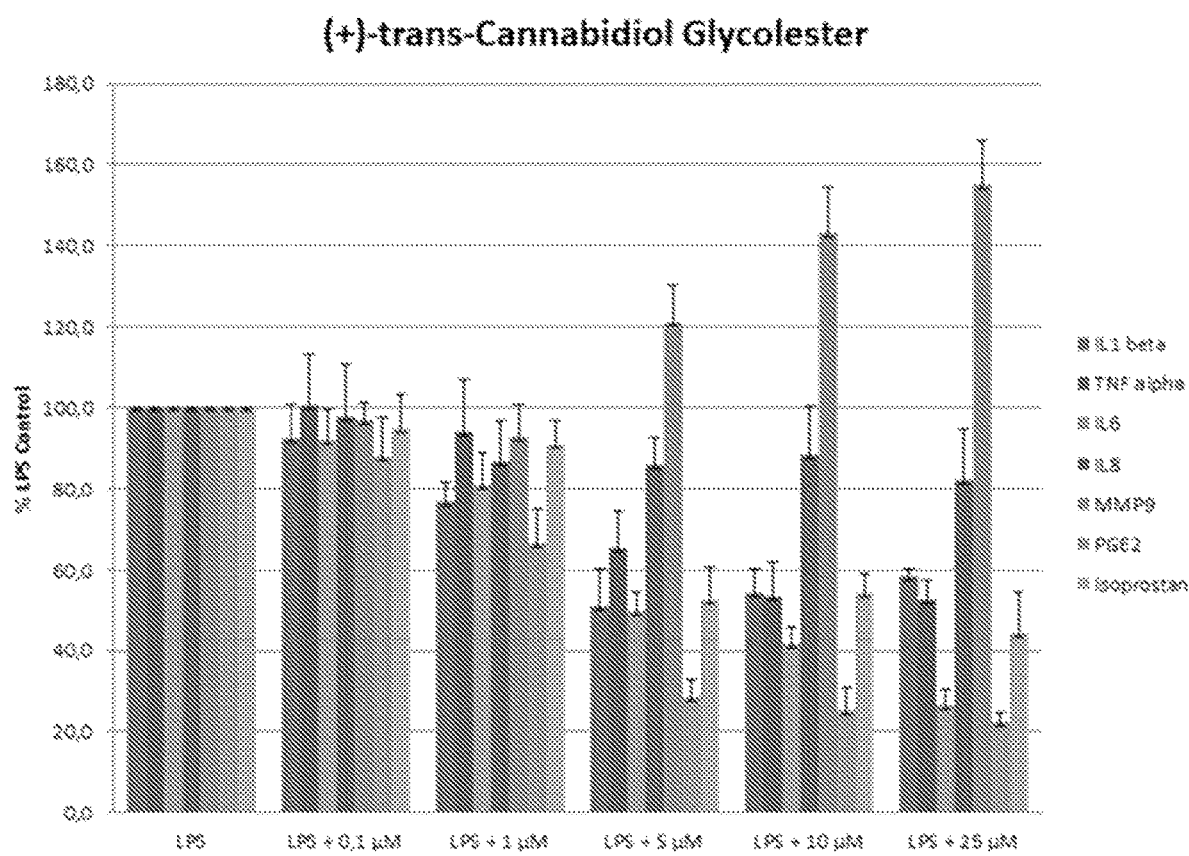
FIG. 34 shows the effects of (+)-CBD-GE on inflammatory parameters in LPS-treated human monocytes as evaluated in example 6. The columns for each concentration indicate from left to right: IL1 beta, TNF alpha, IL6, IL8, MMP9, PGE2 and Isoprostan.

As shown in FIG. 34, (+)-CBD-GE dose-dependently inhibited LPS-stimulated TNFalpha, IL-6, IL-1, isoprostane, and PGE2 release starting at 0.1 µM and maximal effects using 25 µM, which showed an inhibition of around 80% for IL-6 and PGE2 and approx. 40% for the other three parameters. LPS-induced IL-8 was not affected, whereas LPS-mediated MMP9 was strongly enhanced (20-60% more than LPS values) in the doses of 5-25 µM.

Figure 35:
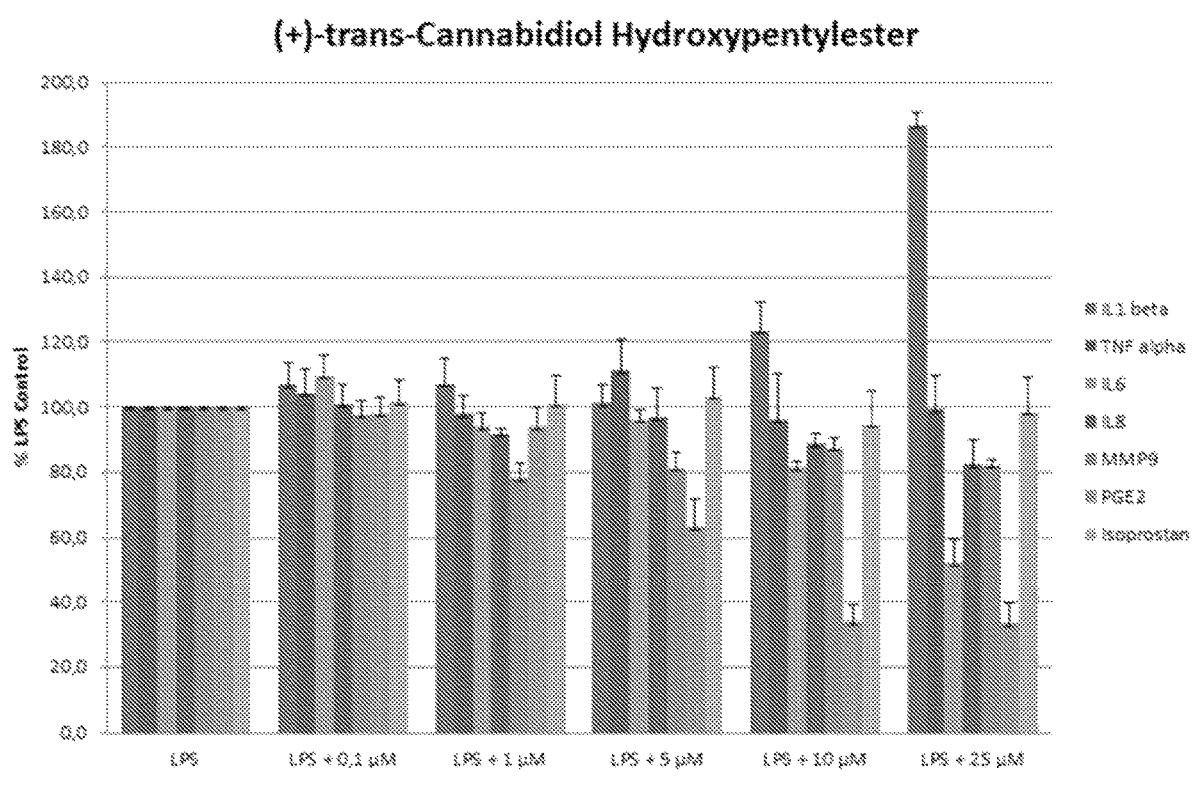
FIG. 35 shows the effects of (+)-CBD-HPE on inflammatory parameters in LPS-treated human monocytes as evaluated in example 6. The columns for each concentration indicate from left to right: IL1 beta, TNF alpha, IL6, IL8, MMP9, PGE2 and Isoprostan.

(+)-CBD-HPE only slightly inhibited LPS-induced PGE2 in the doses of 5 to 25 µM and IL-6 in the doses of 10 and 25 µM. LPS-stimulated IL-8 and MMP9 were only slightly prevented in the dose of 25 µM, whereas LPS-mediated IL-1beta was potently increased (almost doubling the LPS effect) in the dose of 25 µM, whereas TNFalpha induced by LPS was not affected (FIG. 35).

Effects on IL-1-Induced Inflammatory Parameters in Human Dermal Fibroblasts

Figure 36:
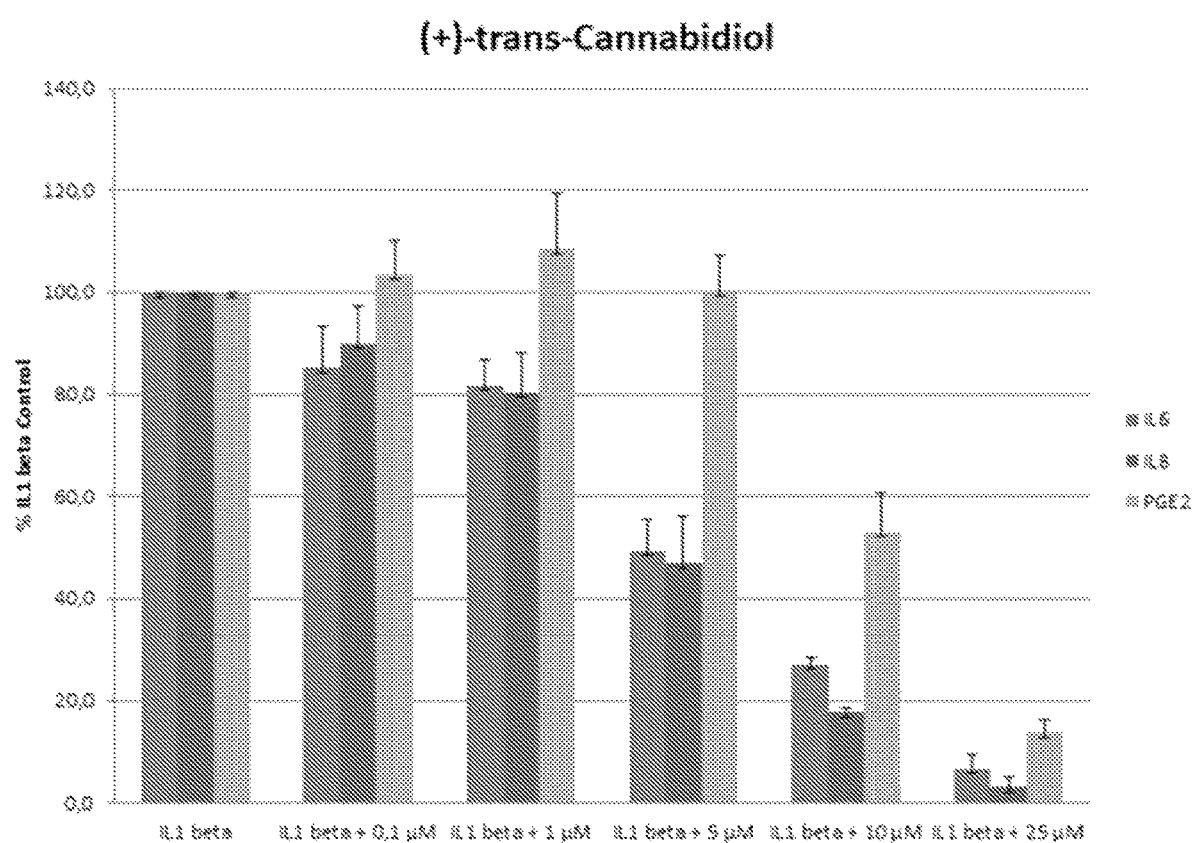
FIG. 36 shows the effects of (+)-CBD on inflammatory parameters in IL-1-treated human dermal fibroblasts as evaluated in example 6. The columns for each concentration indicate from left to right: IL6, IL8 and PGE2.

As shown in FIG. 36, (+)-CBD potently and dose-dependently inhibited IL-1-stimulated IL-6 and IL-8 release starting at 0.1 µM with maximal effects using 25 µM, showing an inhibition of more than 90%. IL-1-induced PGE2 was strongly inhibited in the doses of 10 to 25 µM (more than 80% inhibition).

Figure 37:
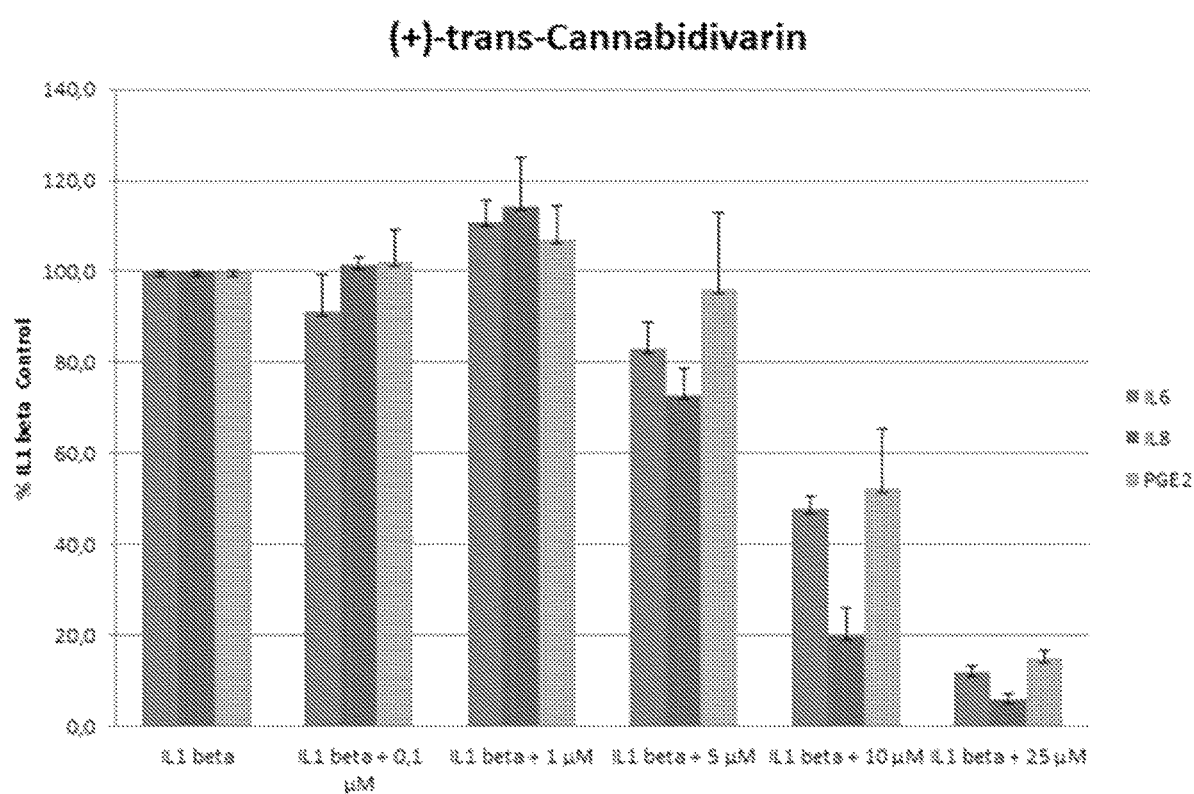
FIG. 37 shows the effects of (+)-CBDV on inflammatory parameters in IL-1-treated human dermal fibroblasts as evaluated in example 6. The columns for each concentration indicate from left to right: IL6, IL8 and PGE2.

(+)-CBDV showed a comparable profile to (+)-CBD, but with a weaker activity on IL-6 and IL-8 which started using 5 µM. IL-1-induced PGE2 was strongly inhibited in the doses of 10 to 25 µM (more than 80% inhibition) (FIG. 37).

Figure 38:
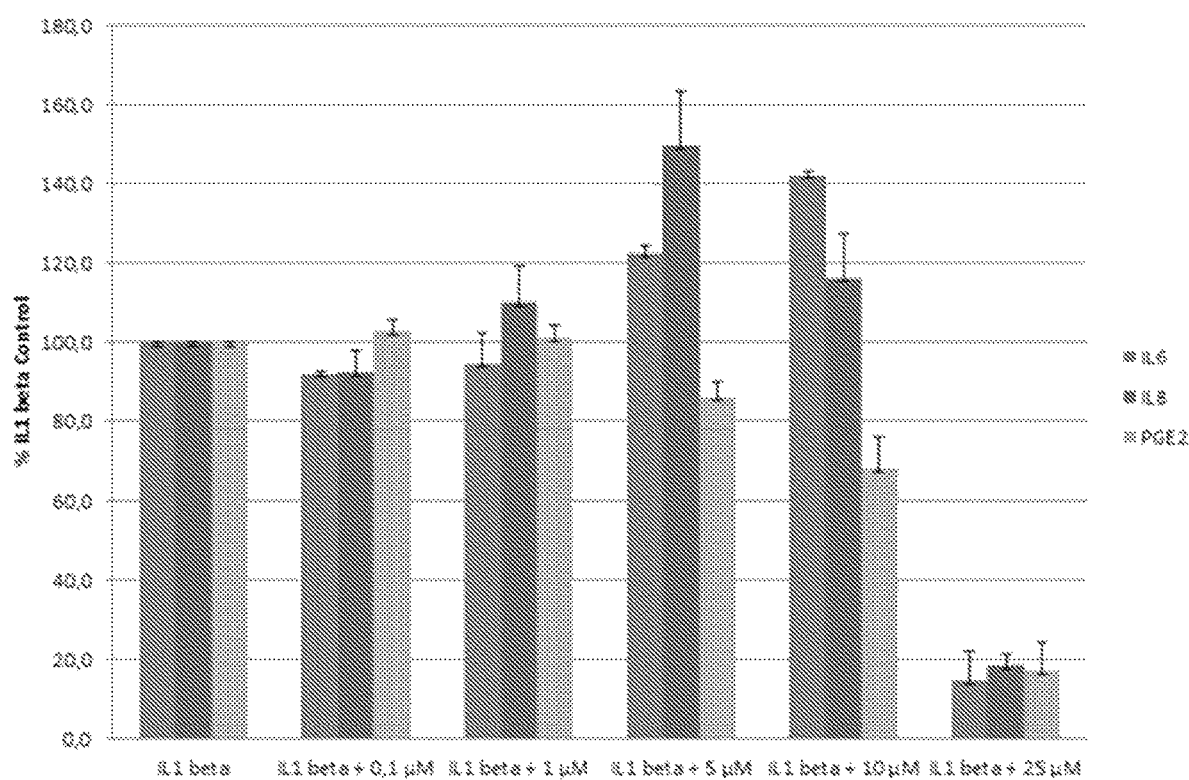
FIG. 38 shows the effects of (+)-CBD-ME on inflammatory parameters in IL-1-treated human dermal fibroblasts as evaluated in example 6. The columns for each concentration indicate from left to right: IL6, IL8 and PGE2.

(+)-CBD-ME slightly increased LPS-induced IL-6 and IL-8 and slightly decreased IL-1-mediated PGE2. The dose of 25 µM seems to be toxic in fibroblasts (FIG. 38).

Figure 39:
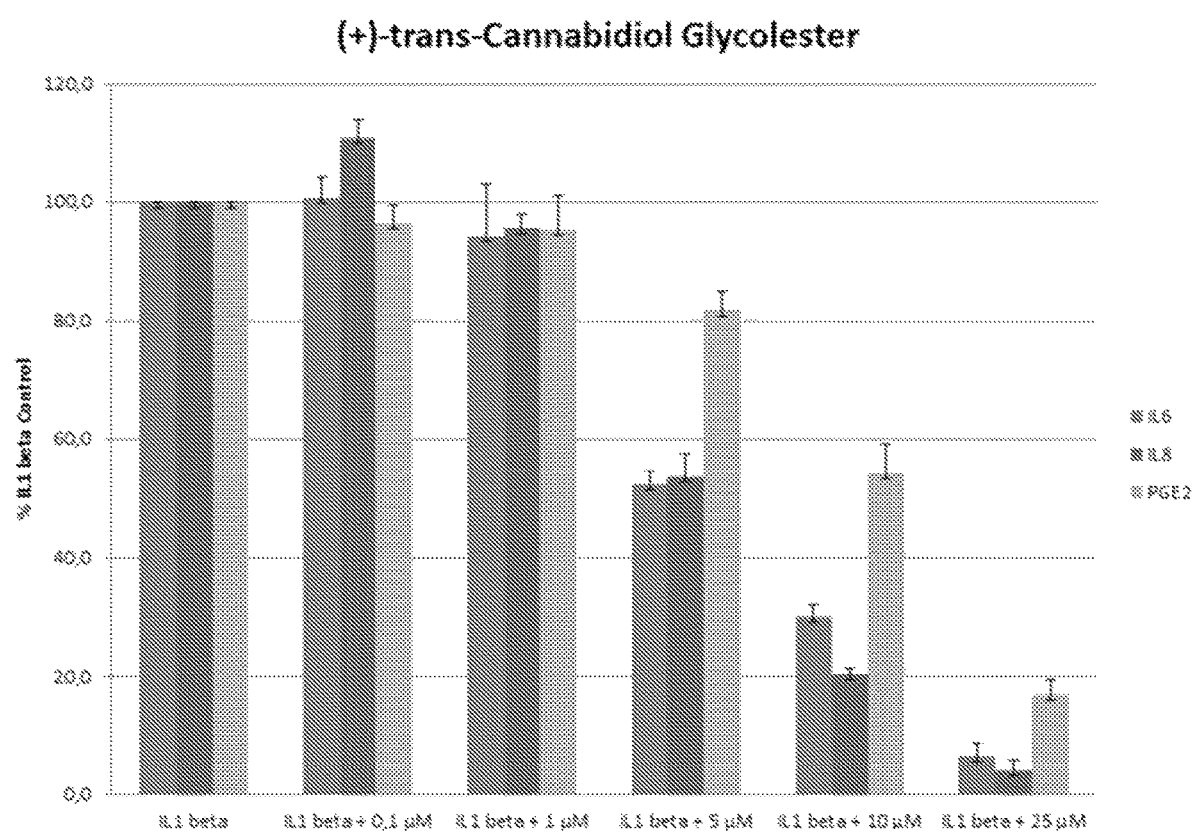
FIG. 39 shows the effects of (+)-CBD-GE on inflammatory parameters in IL-1-treated human dermal fibroblasts as evaluated in example 6. The columns for each concentration indicate from left to right: IL6, IL8 and PGE2.

As shown in FIG. 39, (+)-CBD-GE dose-dependently inhibited all IL-1-stimulated parameters starting at 5 µM and maximal effects using 25 µM, which showed an inhibition of around 95% for IL-6 and IL-8 and approx. 80% for PGE2.

Figure 40:
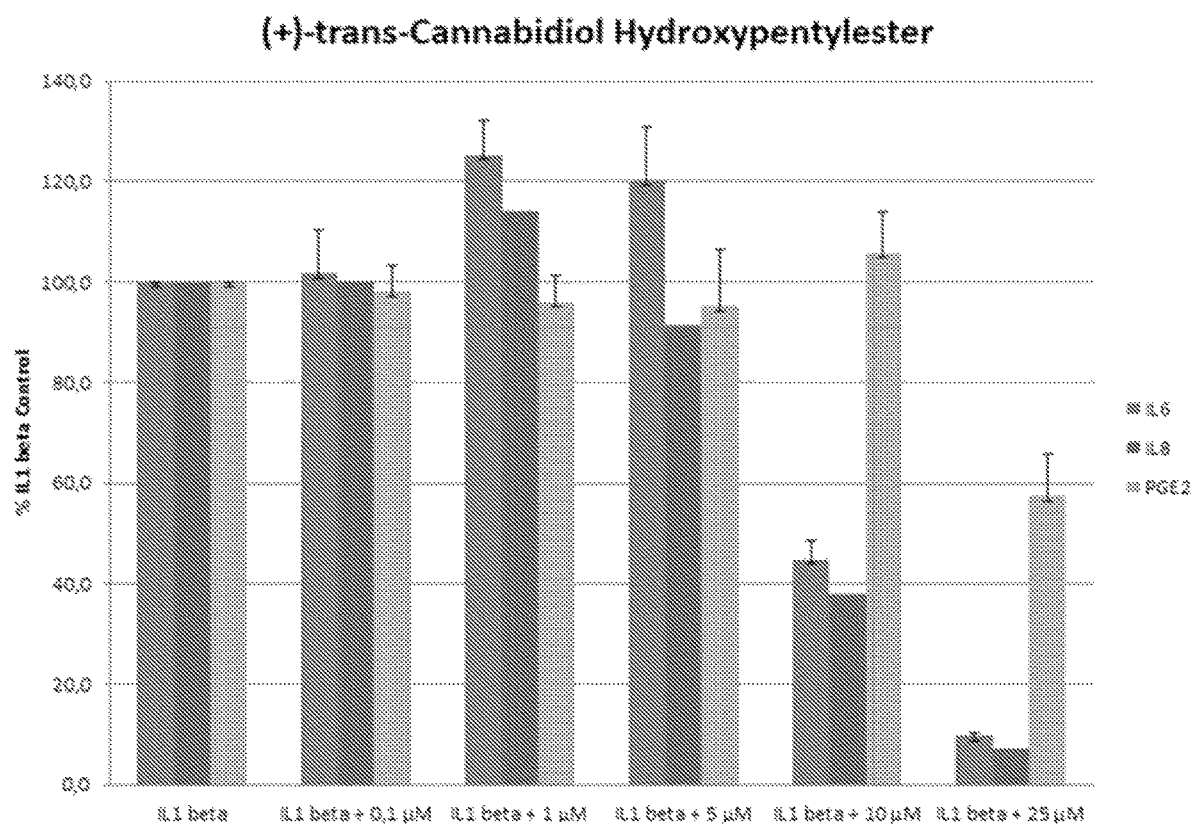
FIG. 40 shows the effects of (+)-CBD-HPE on inflammatory parameters in IL-1-treated human dermal fibroblasts as evaluated in example 6. The columns for each concentration indicate from left to right: IL6, IL8 and PGE2.

(+)-CBD-HPE inhibited IL-1-induced IL-6 and IL-8 in the doses of 10 and 25 µM (95% inhibition) and PGE2 only in the dose of 25 µM (50% inhibition) (FIG. 40).

Effects on Poly I:C-Induced Proteases in Human HaCat Keratinocytes

Figure 41:
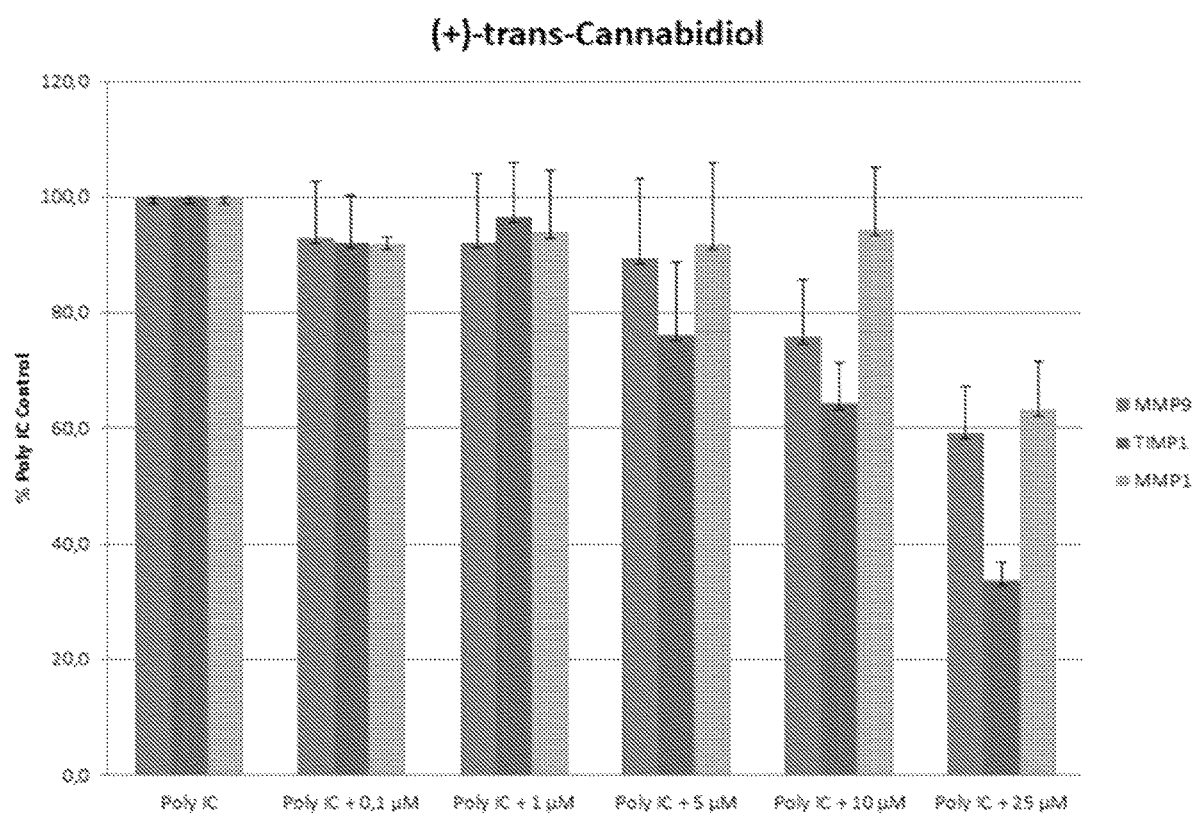
FIG. 41 shows the effects of (+)-CBD on MMP1, MMP9 and TIMP1 in PolyIC-treated human keratinocytes (HaCat) as evaluated in example 6. The columns for each concentration indicate from left to right: MMP9, TIMP1 and MMP1.

As shown in FIG. 41, (+)-CBD slightly inhibited Poly I:C-stimulated MMP9 and TIMP1 starting at 5 µM with maximal effects using 25 µM, showing an inhibition of around 40% for MMP9 and 70% for TIMP1. Poly I:C-induced MMP1 was only slightly inhibited in the doses of 25 µM (more approx. 40% inhibition).

Figure 42:
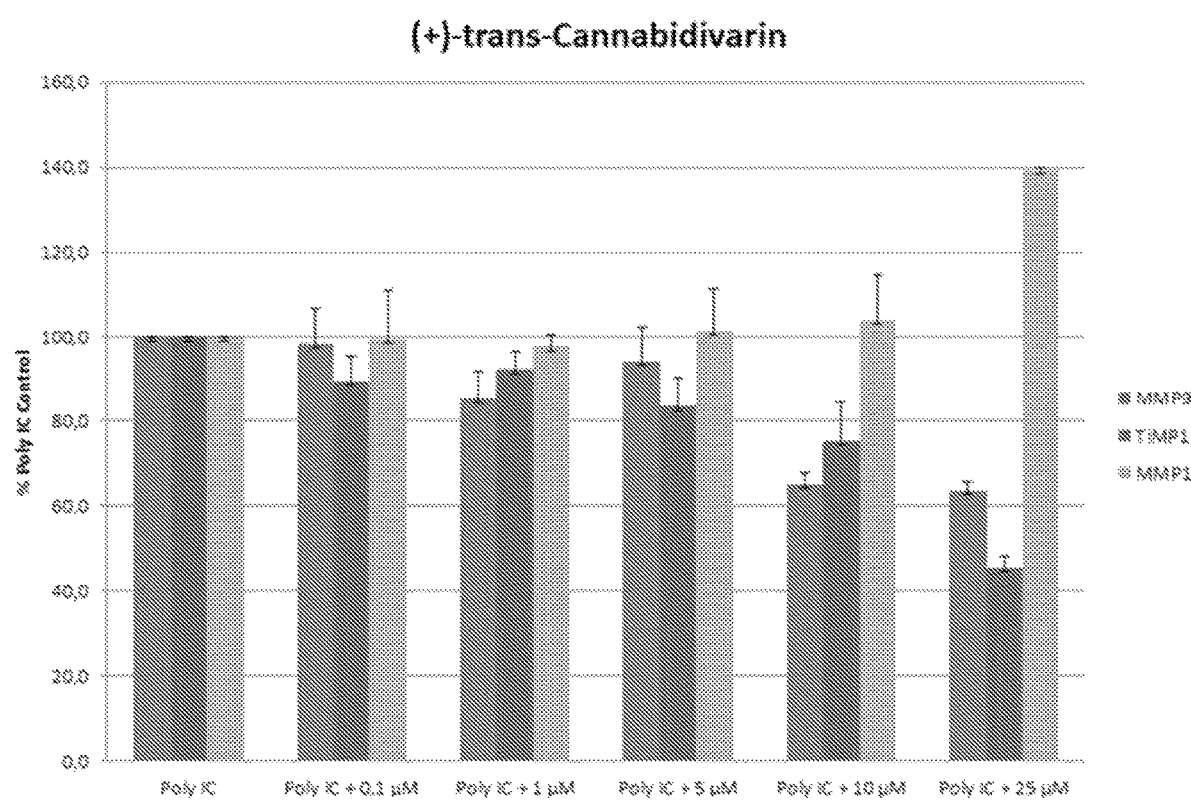
FIG. 42 shows the effects of (+)-CBDV on MMP1, MMP9 and TIMP1 in PolyIC-treated human keratinocytes (HaCat) as evaluated in example 6. The columns for each concentration indicate from left to right: MMP9, TIMP1 and MMP1.

(+)-CBDV showed slight inhibitory effects on Poly I:C-stimulated MMP9 and TIMP1 but enhanced Poly I:C-stimulated MMP1 in the dose of 25 µM (FIG. 42).

Figure 43:
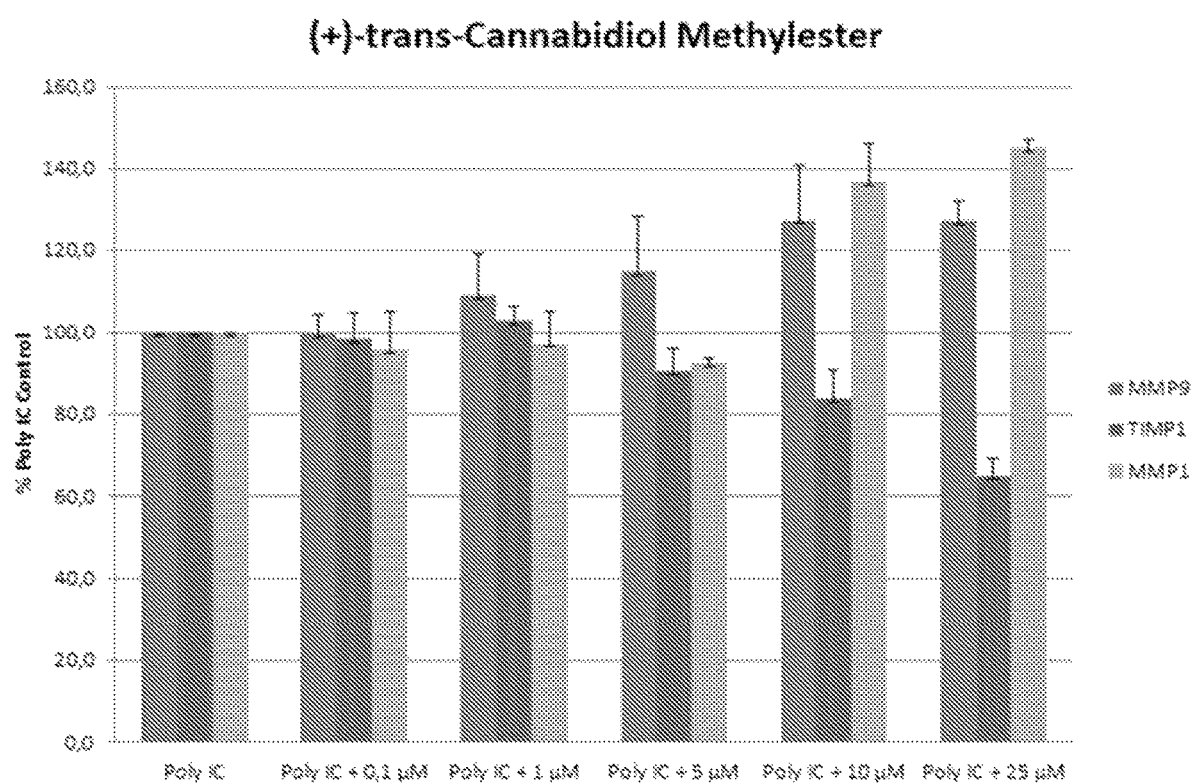
FIG. 43 shows the effects of (+)-CBD-ME on MMP1, MMP9 and TIMP1 in PolyIC-treated human keratinocytes (HaCat) as evaluated in example 6. The columns for each concentration indicate from left to right: MMP9, TIMP1 and MMP1.

(+)-CBD-ME decreased dose-dependently slightly Poly I:C-induced TIMP1 in the doses of 5 to 25 µM (40% inhibition) but enhanced Poly I:C-stimulated MMP9 and MMP1 (FIG. 43).

Figure 44:
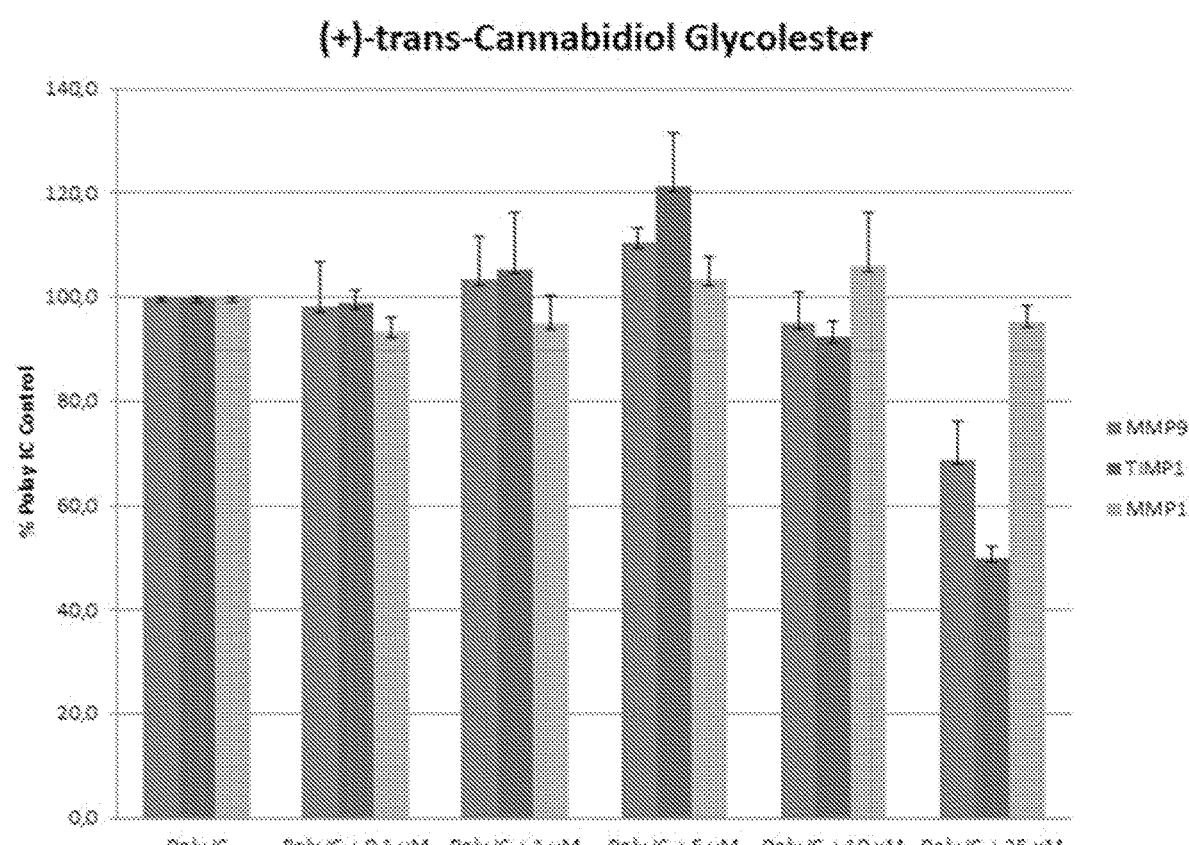
FIG. 44 shows the effects of (+)-CBD-GE on MMP1, MMP9 and TIMP1 in PolyIC-treated human keratinocytes (HaCat) as evaluated in example 6. The columns for each concentration indicate from left to right: MMP9, TIMP1 and MMP1.

As shown in FIG. 44, (+)-CBD-GE (25 µM) showed slight inhibitory effect on Poly I:C-stimulated MMP9 and TIMP1 (30-50% inhibition) but did not affect MMP1 induced by Poly 1:0.

Figure 45:
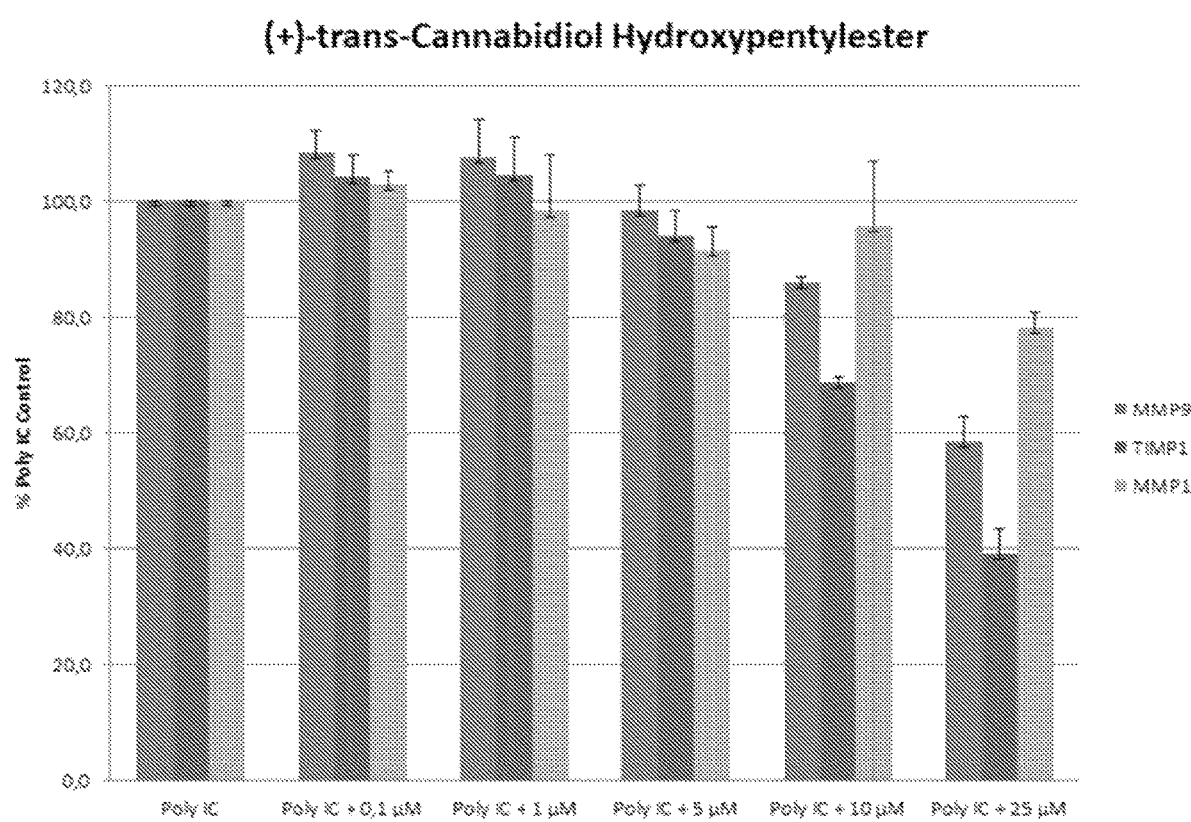
FIG. 45 shows the effects of (+)-CBD-HPE on MMP1, MMP9 and TIMP1 in PolyIC-treated human keratinocytes (HaCat) as evaluated in example 6. The columns for each concentration indicate from left to right: MMP9, TIMP1 and MMP1.

(+)-CBD-HPE showed inhibitory effects on all Poly I:C induced parameters with an inhibition of 40% for MMP9, 60% for TIMP1, and 20% of MMP1 at the dose of 25 µM (FIG. 45).

REFERENCES

Adam L., Salois D., Rihakova L., Lapointe S., St-Onge S., Labrecque J., Payza K., Positive allosteric modulators of CB1 receptors. International Cannabinoid Research Society, Burlington, Vt. 2007, June 26-July 1.

Aso E., Ferrer I., CB2 Cannabinoid Receptor As Potential Target against Alzheimer's Disease. Front. Neurosci., 2016, 10, article 243.

Badal S., Smith K. N., Rajnarayanan R., Analysis of natural product regulation of cannabinoid receptors in the treatment of human disease. Pharmacology & Therapeutics, 2017, 180, 24-48.

Barutta F., Piscitelli F., Pinach S., Bruno G., Gambino, R., Rastaldi, M. P., Salvidio, G., Di Marzo V., Cavallo Perin P., Gruden G., Protective role of cannabinoid receptor type 2 in a mouse model of diabetic nephropathy. Diabetes, 2011, 60 (9), 2386-2396.

Basu S., Ray A., Dittel B N., Cannabinoid receptor 2 is critical for the homing and retention of marginal zone B lineage cells and for efficient T-independent immune responses. J. of Immun., 2011, 187 (11), 5720-5732.

Bátkai S., Osei-Hyiaman D., Pan H., El-Assal O., Rajesh M., Mukhopadhyay P., Hong F., Harvey-White J., Jafri A., Haskó G., Huffman J. W., Gao B., Kunos G., Pacher P., Cannabinoid-2 receptor mediates protection against hepatic ischemia/reperfusion injury. The FASEB Journal, 2007, 21 (8), 1788-1800.

Benito C., Nunez E., Tolón R. M., Carrier E. J., Rábano A., Hillard C. J., Romero J., Cannabinoid CB2 receptors and fatty acid amide hydrolase are selectively overexpressed in neuritic plaque-associated glia in Alzheimer's disease brains. J. of Neurosc., 2003, 23 (35), 11136-11141.

Brotchie J. M., CB1 cannabinoid receptor signalling in Parkinson's disease. Curr. Opin. Pharmacol., 2003, 3(1), 54-61.

Cerri S., Levandis G., Ambrosi G., Montepeloso E., Antoninetti G. F., Franco R., Lanciego J. L., Baqi Y., Müller C. E., Pinna A., Blandini F., Armentero M. T., Neuroprotective potential of adenosine A2A and cannabinoid CB1 receptor antagonists in an animal model of Parkinson disease. J. Neuropathol. Exp. Neurol., 2014, 73 (5), 414-424.

Chandler M. A., Rennard S. I., Chapter 47—Smoking Cessation-Asthma and COPD, 2009, 599-607.

Chen D. J., Gao M., Gao F. F., Su Q. X., Wu J., Brain cannabinoid receptor 2: expression, function and modulation. Acta Pharmacol Sin., 2017, 38(3): 312-316.

Concannon R., Finn D. P., Dowd E., Chapter 3—Cannabinoids in Parkinson's disease. Cannabinoids in Neurologic and Mental Disease, 2015, 35-59.

De Petrocellis L, Cascio M. G., Di Marzo V., The endocannabinoid system: a general view and latest additions. Br. J. Pharmacol., 2004, 141(5). 765-774.

Dittel B. N., Direct suppression of autoreactive lymphocytes in the central nervous system via the CB(2) receptor. British Journal of Pharmacology, 2008, 153 (2), 271-276.

Dourish C. T., Wilding J. P. H., Halford J. C. G., Anti-obesity Drugs: From Animal Models to Clinical Efficacy. Animal and Translational Models for CNS Drug Discovery, 2008, 8, 272-315.

Elphick M. R., Egertová M., The neurobiology and evolution of cannabinoid signalling. Biol. Sc., 2001, 356 (1407): 381-408.

Guzman M., Cannabinoids: potential anticancer agents. Nature Reviews. Cancer, 2003, 3 (10), 745-755.

Han K. H., Lim S., Ryu J., Lee C. W., Kim Y., Kang J. H., Kang S. S., Ahn Y. K., Park C. S., Kim J. J., CB1 and CB2 cannabinoid receptors differentially regulate the production of reactive oxygen species by macrophages. Cardiovascular Research, 2009, 84, 378-386.

Horswill J. G., Bali U., Shaaban S., Keily J. F., Jeevaratnam P., Babbs A. J., Reynet C., Wong Kai In P., PSNCBAM-1, a novel allosteric antagonist at cannabinoid CB1 receptors with hypophagic effects in rats. Br. J. Pharmacol., 2007, 152, 805-814.

Izzo A., Camilleri M., Emerging role of cannabinoids in gastrointestinal and liver diseases: basic and clinical aspects. Gut, 2008, 57 (8), 1140-1155.

Klein T. W., Newton C., Larsen K., Lu L., Perkins I., Nong L., Friedman H., The cannabinoid system and immune modulation. J Leukoc Biol., 2003, 74, 486-496.

Koob G. F., Arends M. A., Le Moal M., Chapter 8—Cannabinoids. Drugs, Addiction, and the Brain, 2014, 261-308.

Le Boisselier R., Alexandre J., Lelong-Boulouard V., Debruyne D., Focus on cannabinoids and synthetic cannabinoids. Clinical Pharmacology & Therapeutics, 2017, 101 (2), 220-229.

Li S. S., Wang L. L., Liu M., Jiang S-H., Zhank M., Tian Z-L., Wang M., Li J-Y., Zhao L., Guan D-W., Cannabinoid CB2 receptors are involved in the regulation of fibrogenesis during skin wound repair in mice. Mol. Med. Rep., 2016, 13(4), 3441-3450.

Likar R., Köstenberger M., Neuwersch S., Clinical use of cannabinoids. Pharmakon 2017, 5 (2), 137-141.

Lotersztajn S., Teixeira-Clerc F., Julien B., Deveaux V., Ichigotani Y., Manin S., Tran-Van-Nhieu J., Karsak M., Zimmer A., Mallat A., CB2 receptors as new therapeutic targets for liver diseases. British Journal of Pharmacology, 2008, 153 (2), 286-289.

Mach F., Montecucco F., Steffens S., Cannabinoid receptors in acute and chronic complications of atherosclerosis. British Journal of Pharmacology, 2008, 153 (2), 290-98.

Mallat A., Teixeira-Clerc F., Deveaux V., Lotersztajn S., Cannabinoid receptors as new targets of antifibrosing strategies during chronic liver diseases. Expert Opinion on Therapeutic Targets, 2007, 11 (3), 403-409.

Marquart S., Zerr P., Akhmetshina A., Palumbo K., Reich N.,Tomcik M., Horn A., Dees C., Engel M., Zwerina J., Distler O., Schett G., Inactivation of the Cannabinoid Receptor CB1 Prevents Leukocyte Infiltration and Experimental Fibrosis. Arthritis & Rheumatism, 2010, 62 (11), 3467-3476.

Navarro H. A., Howard J. L., Pollard G. T., Carroll F. I., Positive allosteric modulation of the human cannabinoid (CB1) receptor by RTI-371, a selective inhibitor of the dopamine transporter. Br. J. Pharmacol., 2009, 156, 1178-1184.

Ofek O., Karsak M., Leclerc N., Fogel M., Frenkel B., Wright K., Tam J., Attar-Namdar M., Kram V., Shohami E., Mechoulam R., Zimmer A., Bab I., Peripheral cannabinoid receptor, CB2, regulates bone mass. Proceedings of the National Academy of Sciences of the United States of America, 2006, 103 (3), 696-701.

Pacher P., Bátkai S., Kunos G., The endocannabinoid system as an emerging target of pharmacotherapy. Pharmacol. Rev., 2006, 58(3), 389-462.

Pertwee R. G., Cannabinoids and Multiple Sclerosis. Molecular Neurobiology, 2007, 36 (1), 45-59.

Pertwee R. G., Howlett A. C., Abood M. E., Alexander S. P., Di Marzo V., Elphick M. R., Greasley P. J., Hansen H. S., Kunos G., Mackie K., Mechoulam R., Ross R. A., International Union of Basic and Clinical Pharmacology. LXXIX. Cannabinoid receptors and their ligands: beyond $CB_1$ and $CB_2$. Pharmacol. Rev., 2010; 62(4), 588-631.

Pertwee R. G., The diverse CB1 and CB2 receptor pharmacology of three plant cannabinoids: Δ9-tetrahydrocannabinol, cannabidiol and Δ9-tetrahydrocannabivarin. Br. J. Pharmacol., 2008, 153, 199-215.

Price M. R., Baillie G. L., Thomas A., Stevenson L. A., Easson M., Goodwin R., McLean A., McIntosh L., Goodwin G., Walker G., Allosteric modulation of the cannabinoid CB1 receptor. Mol. Pharmacol., 2005, 68.1484-1495.

Ravan S., Martinez D., Slifstein M., Abi-Dargham A., Chapter 18—Molecular imaging in alcohol dependence. Handbook of Clinical Neurology, 2014, 125, 293-311.

Sagredo O., Pazos M. R., Valdeolivas S., Fernandez-Ruiz J., Cannabinoids: novel medicines for the treatment of Huntington's disease. Recent Patents on CNS Drug Discovery, 2012, 7 (1), 41-48.

Servettaz A., Kavian N., Nicco C., Deveaux V., Chéereau C., Wang A., Zimmer A., Lotersztajn S., Weill B., Batteux F., Targeting the Cannabinoid Pathway Limits the Development of Fibrosis and Autoimmunity in a Mouse Model of Systemic Sclerosis. Am. J. Pathol., 2010, 177(1), 187-196.

Sharma A., Marcil W., Petty F., xPharm: The Comprehensive Pharmacology Reference. Biomed. Sc., 2007, 1-6.

Teixeira-Clerc F., Julien B., Grenard P., Tran Van Nhieu J., Deveaux V., Li L., Serriere-Lanneau V., Ledent C., Mallat A., Lotersztajn S., CB1 cannabinoid receptor antagonism: a new strategy for the treatment of liver fibrosis. Nat. Med., 2006, 12, 671-676.

Wagner J. D., Cann J. A., Zhang L., Harwood Jr. H. J., Chapter 14—Diabetes and Obesity Research using Nonhuman Primates. Nonhuman Primates in Biomedical Research, 2012, 699-732.

Wilkinson J. D., Williamson E. M., Cannabinoids inhibit human keratinocyte proliferation through a non-CB1/CB2 mechanism and have a potential therapeutic value in the treatment of psoriasis. Journal of dermatological science, 2007, 45, 87-92.

Wright K. L., Duncan M., Sharkey K. A., Cannabinoid CB2 receptors in the gastrointestinal tract: a regulatory system in states of inflammation. British Journal of Pharmacology, 2008, 153 (2), 263-270.

Zhang M., Martin B. R., Adler M. W., Razdan R. K., Jallo J. I., Tuma R. F., Cannabinoid CB(2) receptor activation decreases cerebral infarction in a mouse focal ischemia/reperfusion model. Journal of Cerebral Blood Flow and Metabolism, 2007, 27 (7), 1387-1396.

Zheng J. L., Yu T. S., Li X. N., Fan Y. Y., Ma W. X., Du Y., Zhao R., Guan D. W., Cannabinoid receptor type 2 is time-dependently expressed during skin wound healing in mice. Int. J. Legal Med., 2012, 126, 807-814.

The invention claimed is:

1. A method for producing a compound of formula (I), or a salt thereof, (I)

wherein

X=H or —COOY,

Y=a saturated or unsaturated, branched or unbranched alkyl group, an aryl group, or a heteroaryl group, having 1 to 12 carbon atoms, respectively, and optionally substituted with one or more amino group(s), hydroxyl group(s) and/or halogen(s), and n=2 or 4, the method comprising:

i) reacting 4S-menthadienol in a halogen free solvent with a compound of formula (II) in a continuous flow reaction process,

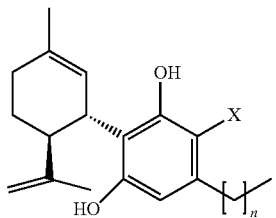

(II)

wherein n=2 or 4, to obtain a compound of formula (III)

(III)

wherein n=2 or 4;

ii) optionally, transesterification of the compound of formula (III); and iii) optionally, decarboxylation of the compound of formula (III) and/or the transesterified product of formula (III) with an acid.

2. The method according to claim 1, wherein the compound of formula (I) is selected from the group consisting of compounds (1) to (5) and/or salts thereof:

(1)

(2)

(3)

(4)

-continued

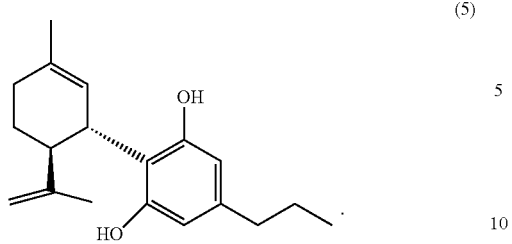

(5)

3. The method according to claim 1, wherein pure 1S,4S-menthadienol or pure 1R,4S-menthadienol or a mixture thereof is used in step i).

4. The method according to claim 1, wherein in step i) a solution of a Lewis acid catalyst is provided and brought into contact with a solution of a compound of formula (II) and 4S-menthadienol.

5. The method according to claim 4, wherein the Lewis acid catalyst is boron trifluoride diethyl etherate.

6. The method according to claim 1, wherein in step ii) a transesterification with ethylene glycol and/or 1,2-pentanediol is conducted.

7. The method claim 1, wherein the halogen-free solvent is toluene.

* * * * *